United States Patent
Numata

(10) Patent No.: US 9,923,151 B2
(45) Date of Patent: Mar. 20, 2018

(54) MATERIAL FOR ORGANIC ELECTROLUMINESCENT ELEMENTS, AND ORGANIC ELECTROLUMINESCENT ELEMENT USING SAME

(75) Inventor: Masaki Numata, Chiba (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 832 days.

(21) Appl. No.: 13/976,246

(22) PCT Filed: Dec. 26, 2011

(86) PCT No.: PCT/JP2011/080133
§ 371 (c)(1),
(2), (4) Date: Jun. 26, 2013

(87) PCT Pub. No.: WO2012/090967
PCT Pub. Date: Jul. 5, 2012

(65) Prior Publication Data
US 2013/0270540 A1    Oct. 17, 2013

(30) Foreign Application Priority Data
Dec. 28, 2010 (JP) .................. 2010-293899

(51) Int. Cl.
| | | |
|---|---|---|
| *H01L 51/50* | (2006.01) |
| *H01L 51/00* | (2006.01) |
| *C09K 11/06* | (2006.01) |
| *C07D 471/04* | (2006.01) |
| *C07D 491/044* | (2006.01) |
| *C07D 495/04* | (2006.01) |
| *C07D 519/00* | (2006.01) |
| *C07F 7/08* | (2006.01) |

(52) U.S. Cl.
CPC ........ *H01L 51/0072* (2013.01); *C07D 471/04* (2013.01); *C07D 491/044* (2013.01); *C07D 495/04* (2013.01); *C07D 519/00* (2013.01); *C07F 7/0814* (2013.01); *C09K 11/06* (2013.01); *H01L 51/0071* (2013.01); *H01L 51/0073* (2013.01); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *H01L 51/0085* (2013.01); *H01L 51/5016* (2013.01); *H01L 51/5056* (2013.01); *H01L 51/5072* (2013.01)

(58) Field of Classification Search
None
See application file for complete search history.

(56) References Cited

U.S. PATENT DOCUMENTS

| | | | |
|---|---|---|---|
| 6,589,673 B1 | 7/2003 | Kido et al. | |
| 2009/0134784 A1* | 5/2009 | Lin | C07D 209/88 313/504 |
| 2009/0153034 A1 | 6/2009 | Lin et al. | |
| 2011/0006670 A1 | 1/2011 | Katakura et al. | |
| 2011/0260138 A1* | 10/2011 | Xia | C07D 405/14 257/40 |
| 2013/0119360 A1 | 5/2013 | Katakura et al. | |

FOREIGN PATENT DOCUMENTS

| | | | |
|---|---|---|---|
| JP | 2001 102175 | 4/2001 | |
| JP | 2008 74939 | 4/2008 | |
| JP | 2008 135498 | 6/2008 | |
| JP | 2008 294161 | 12/2008 | |
| JP | 2011-084531 * | 4/2011 | ............. H01L 51/50 |
| JP | 2011 84531 | 4/2011 | |
| KR | 10-2010-0032888 | 3/2010 | |
| WO | 2009 060780 | 5/2009 | |
| WO | WO 2009/060780 A1 * | 5/2009 | ............. H01L 51/50 |
| WO | WO 2009/090780 A1 * | 5/2009 | ............. H01L 51/50 |
| WO | 2009 086028 | 7/2009 | |

OTHER PUBLICATIONS

International Search Report dated Feb. 21, 2012 in PCT/JP11/80133 Filed Dec. 26, 2011.
Office Action dated Aug. 14, 2017 in Korean Patent Application No. 10-2013-7016797.

* cited by examiner

*Primary Examiner* — Gregory D Clark
(74) *Attorney, Agent, or Firm* — Oblon, McClelland, Maier & Neustadt, L.L.P.

(57) ABSTRACT

A material for organic electroluminescence device having a specific structure, in which an aromatic ring of a dibenzofuran skeleton, a carbazole skeleton, or a dibenzothiophene skeleton has a nitrogen atom as a heteroatom, and an organic electroluminescence device including an organic thin film layer which includes one or more layers between a cathode and an anode. The organic thin film layer includes a light emitting layer which includes a phosphorescent emitting material. At least one layer of the organic thin film layer includes the material for organic electroluminescence device. The organic EL device employing the material for organic EL device has a high external quantum efficiency even when driving the device at low voltage and also has a long lifetime.

31 Claims, No Drawings

MATERIAL FOR ORGANIC ELECTROLUMINESCENT ELEMENTS, AND ORGANIC ELECTROLUMINESCENT ELEMENT USING SAME

TECHNICAL FIELD

The present invention relates to materials for organic electroluminescence devices and organic electroluminescence devices employing the materials.

BACKGROUND ART

Organic electroluminescence devices (also referred to as "organic EL devices") is a spontaneous light emitting devices which utilize the phenomenon that a fluorescent or phosphorescent substance emits light by energy of recombination of holes injected from an anode and electrons injected from a cathode when an electric field is applied. Since an organic EL device of laminate type which can be driven under low electric voltage was reported, many studies have been made on organic EL devices which are made of organic materials. In the reported laminate devices, tris(8-quinolinolato)aluminum was used in the light emitting layer and a triphenyldiamine derivative was used in the hole transporting layer. Advantages of the laminate structure are that the efficiency of hole injection into the light emitting layer can be increased, that the efficiency of forming excitons by recombination can be increased, because the electrons injected from the cathode are blocked, and that the excitons formed in the light emitting layer can be confined. As the structure of the organic EL device, a two-layered structure having a hole transporting (injecting) layer and an electron transporting, light emitting layer as employed in the reported device and a three-layered structure having a hole transporting (injecting) layer, a light emitting layer and an electron transporting (injecting) layer are well known. To increase the efficiency of recombination of injected holes and electrons in the devices of the laminate type, the structure of the device and the process for forming the device have been studied.

As the emitting material of organic EL devices, for examples, chelate complexes, such as tris(8-quinolinolato) aluminum, coumarin derivatives, tetraphenylbutadiene derivatives, distylylarylene derivatives, and oxadiazole derivatives have been known. It has been reported that these emitting materials emit blue to red visible lights and color devices are expected to be developed.

The fluorescent emitting material which causes the emission from singlet excitons has been hitherto used as the emitting material of organic EL devices. Recently, in addition to the fluorescent emitting material, it has been proposed to use the phosphorescent emitting material which causes emission from triplet excitons. The singlet excitons and the triplet excitons may generate in a ratio of 1:3 in organic EL device by the recombination of electros and hole in accordance with their difference in the spin multiplicity. Therefore, an organic EL device employing the phosphorescent emitting material achieves an emission efficiency three to four times higher than that of an organic EL device employing only the fluorescent emitting material.

However, a high efficient and long lifetime blue-phosphorescent emission is difficult to achieve. Therefore, the host material, the hole transporting material, and the electron transporting material which are to be exist around the phosphorescent dopant are required to have a high triplet excited energy for achieving a high internal quantum efficiency of emission, to have a wide gap for energetically confining the excitons of the emitting dopant, to have a high carrier injecting ability and transporting ability for achieving a high efficiency of power conversion, to allow a driving at low voltage, and to have a high chemical and heat stability for a long lifetime. The device performance may be optimized by optimizing the chemical structure of material. If the performance (mainly carrier balance) is simply changed according to the structural modification of the material, the study on the material can be significantly facilitated.

Patent Documents 1 and 2 disclose a compound having a carbazole ring. However, a compound having an unsaturated nitrogen atom in the ring is not disclosed.

Patent Documents 3 to 5 disclose a dibenzofuran ring and a dibenzothiophene ring each having an unsaturated nitrogen atom in the ring and a combined structure of carbazole rings wherein the nitrogen atom at 9-position of one ring is bonded to the carbon atom at 3-position of another ring. It is reported that a compound having such structure reduces the oxidation-reduction potential and improves the electrochemical stability. However, these patent documents are silent about the properties of a compound which has a dibenzofuran ring or dibenzothiophene ring each having an unsaturated nitrogen atom in the ring and the performance of a device employing such a compound.

Patent Documents 6 discloses a compound which has a dibenzofuran ring or a dibenzothiophene ring each having an unsaturated nitrogen atom in the ring, wherein these rings are bonded to each other by carbon atoms through a linking group.

PRIOR ART DOCUMENTS

Patent Documents

Patent Document 1: JP 2008-135498A
Patent Document 2: JP 2008-294161A
Patent Document 3: WO 2009/086028
Patent Document 4: US 2009/153034
Patent Document 5: US 2009/134784
Patent Document 6: JP 2008-074939A

SUMMARY OF THE INVENTION

Problems to be Solved by the Invention

The present invention has been made to solve the above problems. An object of the present invention is to provide an organic EL device with a long lifetime which has high external quantum efficiency even when driving the device at low voltage and also provide a material for organic EL device realizing such a device.

Means for Solving the Problems

As a result of extensive research for achieving the above objects, the inventor has found that an organic EL device employing a compound represented by the following formula (1) emits phosphorescent light with high efficiency even when driving the device at low voltage and prolongs the lifetime of the device. The present invention has been made on the basis of this finding.

The present invention provides a material for organic electroluminescence device represented by formula (1):

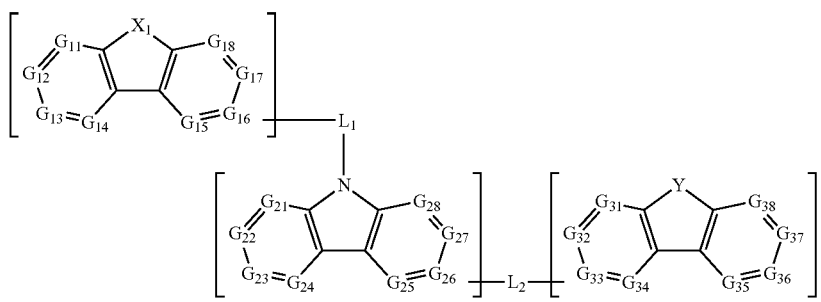

wherein:
at least one of $G_{11}$ to $G_{18}$ represents a nitrogen atom, another of $G_{11}$ to $G_{18}$ represents a carbon atom bonded to $L_1$, and the other or others of $G_{11}$ to $G_{18}$ represent $C(R_1)$;
one of $G_{21}$ to $G_{28}$ represents a carbon atom bonded to $L_2$ and the others represent $C(R_2)$ or a nitrogen atom;
one of $G_{31}$ to $G_{38}$ represents a carbon atom bonded to $L_2$ and the others represent $C(R_3)$ or a nitrogen atom;
each of $R_1$ to $R_3$ independently represents a hydrogen atom, a substituted or unsubstituted alkyl group including 1 to 20 carbon atoms, a substituted or unsubstituted cycloalkyl group including 3 to 20 ring carbon atoms, a substituted or unsubstituted cycloalkoxy group including 3 to 20 ring carbon atoms, a substituted or unsubstituted alkoxy group including 1 to 20 carbon atoms, a substituted or unsubstituted aryl group including 6 to 18 ring carbon atoms, a substituted or unsubstituted heteroaryl group including 5 to 18 ring atoms, a substituted or unsubstituted aryloxy group including 6 to 18 ring carbon atoms, a substituted or unsubstituted amino group including 0 to 20 carbon atoms, a substituted or unsubstituted silyl group including 0 to 30 carbon atoms, a fluorine atom, or a cyano group, provided that $R_1$ groups, $R_2$ groups, and $R_3$ groups may be the same or different;
a substituent of $R_1$ to $R_3$ independently represents an alkyl group including 1 to 20 carbon atoms, a cycloalkyl group including 3 to 20 ring carbon atoms, an alkoxy group including 1 to 20 carbon atoms, a cycloalkoxy group including 3 to 20 ring carbon atoms, an aryl group including 6 to 18 ring carbon atoms, a heteroaryl group including 5 to 18 ring atoms, an aryloxy group including 6 to 18 ring carbon atoms; an amino group including 0 to 20 carbon atoms, a silyl group including 0 to 30 carbon atoms, a fluorine atom, or a cyano group;
$X_1$ represents an oxygen atom, a sulfur atom or —N($R_4$)—;
$R_4$ represents a hydrogen atom, an alkyl group including 1 to 20 carbon atoms, a cycloalkyl group including 3 to 20 ring carbon atoms, an aryl group including 6 to 18 ring carbon atoms, or a heteroaryl group including 5 to 18 ring atoms;
$L_1$ represents a single bond, an alkylene group including 1 to 20 carbon atoms, a cycloalkylene group including 3 to 20 ring carbon atoms, an arylene group including 6 to 18 ring carbon atoms, or a heteroarylene group including 5 to 18 ring atoms, provided that divalent residues of dibenzofuran and dibenzothiophene are excluded;
$L_2$ represents a single bond, an alkylene group including 1 to 20 carbon atoms, a cycloalkylene group including 3 to 20 ring carbon atoms, an arylene group including 6 to 18 ring carbon atoms, a heteroarylene group including 5 to 18 ring atoms, a nitrogen-containing divalent linking group, an oxygen-containing divalent linking group, a silicon-containing divalent linking group, a phosphorus-containing divalent linking group, or a sulfur-containing divalent linking group;
Y represents an oxygen atom, a sulfur atom or —N(-$L_3$-$R_5$)—;
$L_3$ represents a single bond, an alkylene group including 1 to 20 carbon atoms, a cycloalkylene group including 3 to 20 ring carbon atoms, an arylene group including 6 to 18 ring carbon atoms, or a heteroarylene group including 5 to 18 ring atoms;
$R_5$ represents a hydrogen atom, an alkyl group including 1 to 20 carbon atoms, a cycloalkyl group including 3 to 20 ring carbon atoms, an aryl group including 6 to 18 ring carbon atoms, or a heteroaryl group including 5 to 18 ring atoms, with an alkyl group including 1 to 6 carbon atoms, a cycloalkyl group including 5 to 6 ring carbon atoms, a phenyl group, and a heteroaryl group including 6 to 14 ring atoms being preferred;
provided that when $X_1$ represents an oxygen atom or a sulfur atom, only one of $G_{11}$ to $G_{18}$ represents a nitrogen atom, and when $X_1$ represents —N($R_4$)—, Y represents —N(-$L_3$-$R_5$)— and simultaneously each of $R_2$ and $R_3$ represents a hydrogen atom.

The present invention further provides an organic electroluminescence device comprising an organic thin film layer comprising one or more layers between a cathode and an anode, wherein the organic thin film layer comprises a light emitting layer comprising a phosphorescent emitting material and at least one layer of the organic thin film layer comprises the material for organic electroluminescence device.

EFFECT OF THE INVENTION

The present invention provides an organic EL device having high external quantum efficiency even when driving the device at low voltage and a long lifetime, and further provides a material for organic EL device realizing such an organic EL device.

MODE FOR CARRYING OUT THE INVENTION

The material for organic electroluminescence device of the invention is represented by formula (1);

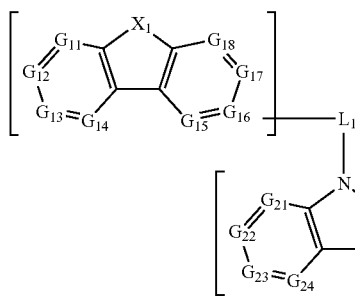

(1)

wherein:

at least one of $G_{11}$ to $G_{18}$ represents a nitrogen atom, another of $G_{11}$ to $G_{18}$ represents a carbon atom bonded to $L_1$, and the other or others of $G_{11}$ to $G_{18}$ represent $C(R_1)$;

one of $G_{21}$ to $G_{28}$ represents a carbon atom bonded to $L_2$ and the others represent $C(R_2)$ or a nitrogen atom;

one of $G_{31}$ to $G_{38}$ represents a carbon atom bonded to $L_2$ and the others represent $C(R_3)$ or a nitrogen atom;

each of $R_1$ to $R_3$ independently represents a hydrogen atom, a substituted or unsubstituted alkyl group having 1 to 20 carbon atoms, a substituted or unsubstituted cycloalkyl group having 3 to 20 ring carbon atoms, a substituted or unsubstituted cycloalkoxy group having 3 to 20 ring carbon atoms, a substituted or unsubstituted alkoxy group having 1 to 20 carbon atoms, a substituted or unsubstituted aryl group having 6 to 18 ring carbon atoms, a substituted or unsubstituted heteroaryl group having 5 to 18 ring atoms, a substituted or unsubstituted aryloxy group having 6 to 18 ring carbon atoms, a substituted or unsubstituted amino group having 0 to 20 carbon atoms, a substituted or unsubstituted silyl group having 0 to 30 carbon atoms, a fluorine atom, or a cyano group, provided that $R_1$ groups, $R_2$ groups, and $R_3$ groups may be the same or different, respectively;

a substituent of $R_1$ to $R_3$ independently represents an alkyl group having 1 to 20 carbon atoms, a cycloalkyl group having 3 to 20 ring carbon atoms, an alkoxy group having 1 to 20 carbon atoms, a cycloalkoxy group having 3 to 20 ring carbon atoms, an aryl group having 6 to 18 ring carbon atoms, a heteroaryl group having 5 to 18 ring atoms, an aryloxy group having 6 to 18 ring carbon atoms, an amino group having 0 to 20 carbon atoms, a silyl group having 0 to 30 carbon atoms, a fluorine atom, or a cyano group;

$X_1$ represents an oxygen atom, a sulfur atom or $—N(R_4)—$;

$R_4$ represents a hydrogen atom, an alkyl group having 1 to 20 carbon atoms, a cycloalkyl group having 3 to 20 ring carbon atoms, an aryl group having 6 to 18 ring carbon atoms, or a heteroaryl group having 5 to 18 ring atoms;

$L_1$ represents a single bond, an alkylene group having 1 to 20 carbon atoms, a cycloalkylene group having 3 to 20 ring carbon atoms, an arylene group having 6 to 18 ring carbon atoms, or a heteroarylene group having 5 to 18 ring atoms, provided that divalent residues of dibenzofuran and dibenzothiophene are excluded;

$L_2$ represents a single bond, an alkylene group having 1 to 20 carbon atoms, a cycloalkylene group having 3 to 20 ring carbon atoms, an arylene group having 6 to 18 ring carbon atoms, a heteroarylene group having 5 to 18 ring atoms, a nitrogen-containing divalent linking group, an oxygen-containing divalent linking group, a silicon-containing divalent linking group, a phosphorus-containing divalent linking group, or a sulfur-containing divalent linking group;

Y represents an oxygen atom, a sulfur atom or $—N(-L_3-R_5)—$;

$L_3$ represents a single bond, an alkylene group having 1 to 20 carbon atoms, a cycloalkylene group having 3 to 20 ring carbon atoms, an arylene group having 6 to 18 ring carbon atoms, or a heteroarylene group having 5 to 18 ring atoms;

$R_5$ represents a hydrogen atom, an alkyl group having 1 to 20 carbon atoms, a cycloalkyl group having 3 to 20 ring carbon atoms, an aryl group having 6 to 18 ring carbon atoms, or a heteroaryl group having 5 to 18 ring atoms;

provided that when $X_1$ represents an oxygen atom or a sulfur atom, only one of $G_{11}$ to $G_{18}$ represents a nitrogen atom, and when $X_1$ represents $—N(R_4)—$, Y represents $—N(-L_3-R_5)—$ and simultaneously each of $R_2$ and $R_3$ represents a hydrogen atom.

As shown in formula (1), an aza-substituted carbazolyl group, an aza-substituted dibenzofuranyl group, or an aza-substituted dibenzothiophenyl group is bonded to an (aza-substituted) carbazolyl group at its N-position (9-position) directly or via a linking group. By this structure, the LUMO level of the aza-substituted carbazole skeleton, the aza-substituted dibenzofuran skeleton or the aza-substituted dibenzothiophene skeleton is made deep, this making the electron injection into the light emitting layer, etc. of an organic EL device employing the material for organic electroluminescence device of the invention. Therefore, the control of the carrier balance is easy, thereby making the present invention more effective.

In a preferred formula (1), Y represents $—N(-L_3-R_5)—$ and $R_5$ represents a heteroaryl group having 6 to 14 ring atoms. In a particularly preferred formula (1), Y represents $—N(-L_3-R_5)—$ and $R_5$ represents a heteroaryl represented by formula (A):

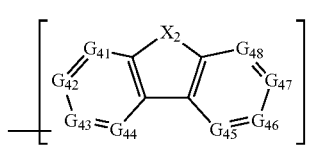

(A)

wherein:

one of $G_{41}$ to $G_{48}$ represents a carbon atom bonded to $L_3$ and the others represent a nitrogen atom or $C(R_6)$;

$R_6$ represents a hydrogen atom, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted cycloalkoxy group having 3 to 20 ring carbon atoms, a substituted or unsubstituted aryl group having 6 to 18 ring carbon atoms, a substituted or unsubstituted heteroaryl group having 5 to 18 ring atoms, a substituted or unsubstituted aryloxy group having 6 to 18 ring carbon atoms, a substituted or unsubstituted amino group having 0 to 20 carbon atoms, a substituted or unsubstituted silyl group having 0 to 30 carbon atoms, a fluorine atom, or a cyano group, provided that $R_6$ groups may be the same or different;

a substituent of $R_6$ independently represents an alkyl group having 1 to 20 carbon atoms, a cycloalkyl group having 3 to 20 ring carbon atoms, an alkoxy group having 1 to 20 carbon atoms, a cycloalkoxy group having 3 to 20 ring carbon atoms, an aryl group having 6 to 18 ring carbon atoms, a heteroaryl group having 5 to 18 ring atoms, an aryloxy group having 6 to 18 ring carbon atoms, an amino group having 0 to 20 carbon atoms, a silyl group having 0 to 30 carbon atoms, a fluorine atom, or a cyano group;

preferably 0 to 4, particularly preferably 0 to 2 of $R_6$ groups represent the substituted or unsubstituted group described above other than the hydrogen atom, provided that when any one or more of $R_6$ groups represent the substituted group described above, 1 to 2 of $R_6$ groups preferably represent the substituted group;

a substituent of $R_6$ independently represents an alkyl group having 1 to 20 carbon atoms, a cycloalkyl group having 3 to 20 ring carbon atoms, an alkoxy group having 1 to 20 carbon atoms, a cycloalkoxy group having 3 to 20 ring carbon atoms, an aryl group having 6 to 18 ring carbon atoms, a heteroaryl group having 5 to 18 ring atoms, an aryloxy group having 6 to 18 ring carbon atoms, an amino group having 0 to 30 carbon atoms, a silyl group having 0 to 30 carbon atoms, a fluorine atom, or a cyano group;

$X_2$ represents an oxygen atom, a sulfur atom or —N($R_7$)—; and $R_7$ represents a hydrogen atom, an alkyl group having 1 to 20 carbon atoms, a cycloalkyl group having 3 to 20 ring carbon atoms, an aryl group having 6 to 18 ring carbon atoms, or a heteroaryl group having 5 to 18 ring atoms.

When Y of formula (1) represents an oxygen atom or a sulfur atom, the molecular weight can be reduced without adversely affecting the effect of the invention, as compared with a compound wherein Y represents —N($R_4$)—. Therefore, the vapor deposition temperature for the production of devices can be reduced, thereby reducing the thermal decomposition of materials.

$X_1$ of formula (1) preferably represents —N($R_4$)—, because the ionization potential is shallow as compared with a compound wherein $X_1$ represents an oxygen atom or a sulfur atom, thereby enhancing the hole injecting ability and the hole transporting ability without adversely affecting the effect of the invention.

Preferably one to four of $G_{11}$ to $G_{18}$ represent nitrogen atoms and particularly preferably one or two of $G_{11}$ to $G_{18}$ represent nitrogen atoms. Further, $G_{14}$ preferably represents a nitrogen atom, and each of $G_{11}$ to $G_{13}$ more preferably represents C($R_1$).

Preferably zero to two of $G_{21}$ to $G_{28}$ represent nitrogen atoms and particularly preferably zero or one of $G_{21}$ to $G_{28}$ represents a nitrogen atom.

Preferably zero to two of $G_{31}$ to $G_{38}$ represent nitrogen atoms and particularly preferably zero or one of $G_{31}$ to $G_{38}$ represents a nitrogen atom.

At least one of $G_{41}$ to $G_{48}$ preferably represents a nitrogen atom, zero to four of $G_{41}$ to $G_{48}$ more preferably represent nitrogen atoms, and zero to two of $G_{41}$ to $G_{48}$ particularly preferably represent nitrogen atoms.

Examples of the alkyl group for $R_1$ to $R_7$ include methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, and 3-methylpentyl group. Of the above, the alkyl groups having 1 to 6 carbon atoms are preferred.

Examples of the cycloalkyl group for $R_1$ to $R_7$ include cyclopropyl group, cyclobutyl group, cyclopentyl group, cyclohexyl group, cycloheptyl group, norbornyl group, and adamantyl group. Of the above, the cycloalkyl groups having 5 or 6 ring carbon atoms are preferred.

Examples of the alkoxy group for $R_1$ to $R_7$ include methoxy group, ethoxy group, propoxy group, butoxy group, pentyloxy group, and hexyloxy group. The alkoxy groups having 3 or more carbon atoms may be linear, cyclic, or branched. Of the above, the alkoxy groups having 1 to 6 carbon atoms are preferred.

Examples of the cycloalkoxy group for $R_1$ to $R_7$ include cyclopentoxy group and cyclohexyloxy group. Of the above, the cycloalkoxy groups having 5 or 6 ring carbon atoms are preferred.

Examples of the aryl group for $R_1$ to $R_7$ include phenyl group, tolyl group, xylyl group, mesityl group, o-biphenyl group, m-biphenyl group, p-biphenyl group, o-terphenyl group, m-terphenyl group, p-terphenyl group, naphthyl group, phenanthryl group, and triphenylenyl group, with phenyl group being preferred.

Examples of the aryloxy group for $R_1$ to $R_7$ include phenoxy group and biphenyloxy group, with phenoxy group being preferred.

Examples of the heteroaryl group for $R_1$ to $R_7$ include carbazolyl group, carbolinyl group, dibenzofuranyl group, dibenzothiophenyl group, pyrrolyl group, furyl group, thienyl group, silolyl group, pyridyl group, quinolyl group, isoquinolyl group, indolyl group, benzofuryl group, benzothiophenyl group, imidazolyl group, benzimidazolyl group, pyrimidyl group, selenophenyl group, oxadiazolyl group, triazolyl group, azaphenanthryl group, and phenanthrolinyl group. Of the above, the heteroaryl groups having 6 to 14 ring atoms are preferred.

The amino group and silyl group for $R_1$ to $R_7$ may be substituted as mentioned above. A trimethylsilyl group is preferred for the substituted silyl group.

Examples of the alkylene group, the cycloalkylene group having 3 to 20 ring carbon atoms, the arylene group having 6 to 18 ring carbon atoms, and the heteroarylene group having 5 to 18 ring atoms for $L_1$ to $L_3$ include residues obtained by removing one hydrogen atom from the corresponding groups mentioned above with respect to $R_1$ to $R_7$. The arylene group referred to herein includes a 9,9-fluorenylidene group.

In addition to those described below, the arylene group is preferably p-phenylene group, m-phenylene group, and biphenylene group. In addition to those described below, the amino group is preferably biphenylamino group Examples of the nitrogen-containing divalent linking group, the oxygen-containing divalent linking group, the silicon-containing divalent linking group, the phosphorus-containing divalent linking group, and the sulfur-containing divalent linking group for $L_2$ include the following groups:

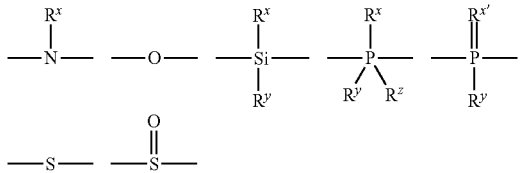

wherein each of $R^x$, $R^y$ and $R^z$ independently represents a hydrogen atom or a group selected from those mentioned above with respect to R groups, and $R^{x'}$ represents an oxygen atom. Of the above, preferred are —S—, phosphoxide group, and ether group.

Each of $L_1$ and $L_3$ independently preferably represents a single bond, an arylene group having 6 to 18 ring carbon atoms, or a heteroarylene group having 5 to 18 ring atoms, and more preferably a single bond, phenylene group, or a heteroarylene group having 6 to 14 ring atoms. When $L_1$ represents an arylene group having 6 to 18 ring carbon atoms or a heteroarylene group having 5 to 18 ring atoms other than a divalent residue of dibenzofuran and a divalent residue of dibenzothiophene, the number of conformational isomers is increased to enhance the amorphous nature. Therefore, the crystallization which may cause device defect or shorten the lifetime of device is easily controlled without adversely affecting the effect of the invention.

$L_2$ preferably represents a single bond, a nitrogen-containing divalent linking group, an oxygen-containing divalent linking group, a silicon-containing divalent linking group, a phosphorus-containing divalent linking group, a sulfur-containing divalent linking group, an arylene group having 6 to 18 ring carbon atoms, or a heteroarylene group having 5 to 18 ring atoms, and more preferably a single bond, a nitrogen-containing divalent linking group, an oxygen-containing divalent linking group, a silicon-containing divalent linking group, a phosphorus-containing divalent linking group, a sulfur-containing divalent linking group, a phenylene group, or a heteroarylene group having 6 to 14 ring atoms. When $L_2$ represents an alkylene group having 1 to 20 carbon atoms, a cycloalkylene group having 3 to 20 ring carbon atoms, an oxygen-containing divalent linking group, a silicon-containing divalent linking group, a phosphorus-containing divalent linking group, or a sulfur-containing divalent linking group, since these linking groups are non-conjugative, the triplet energy has a wide gap to more effectively confine the triplet excitons of an emitting dopant, this being advantageous for achieving high efficiency. This wide-gap triplet energy is also preferred because it allows the use of an emitting dopant with an emission wavelength of higher energy (shorter wavelength).

The material for organic EL device of the invention is used preferably as a host material for use together with an phosphorescent emitting material, a hole transporting material, or an electron transporting material, and more preferably as the host material, the hole transporting material in a layer directly adjacent to the light emitting layer, or the electron transporting material in a layer directly adjacent to the light emitting layer. The triplet energy level of the material is preferably 2.5 eV or more and more preferably 2.8 eV or more.

The material for organic EL device of the invention is preferably represented by formula (2):

(2)

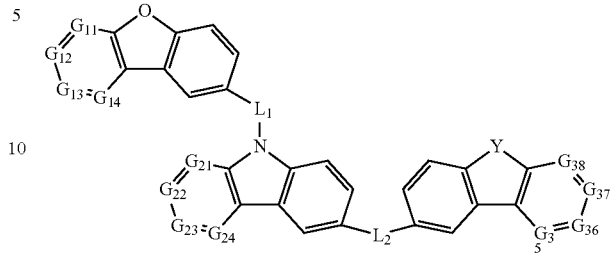

wherein:
one of $G_{11}$ to $G_{14}$ represents a nitrogen atom and the others represent $C(R_1)$;
each of $G_{21}$ to $G_{24}$ represents $C(R_2)$ or a nitrogen atom;
each of $G_{35}$ to $G_{38}$ represents $C(R_3)$ or a nitrogen atom;
each of $R_1$ to $R_3$ independently represents a hydrogen atom, an alkyl group having 1 to 20 carbon atoms, a cycloalkyl group having 3 to 20 ring carbon atoms, an aryl group having 6 to 18 ring carbon atoms, or a heteroaryl group having 5 to 18 ring atoms;
$L_1$ represents a single bond, an arylene group having 6 to 18 ring carbon atoms, or a heteroarylene group having 5 to 18 ring atoms, provided that divalent residues of dibenzofuran and dibenzothiophene are excluded;
$L_2$ represents a single bond, an arylene group having 6 to 18 ring carbon atoms, a heteroarylene group having 5 to 18 ring atoms, a nitrogen-containing divalent linking group, an oxygen-containing divalent linking group, a silicon-containing divalent linking group, a phosphorus-containing divalent linking group, or a sulfur-containing divalent linking group;
Y represents an oxygen atom, a sulfur atom, or —N(-$L_3$-$R_5$)—;
$L_3$ represents a single bond, an arylene group having 6 to 18 ring carbon atoms or a heteroarylene group having 5 to 18 ring atoms; and
$R_5$ represents a hydrogen atom, an alkyl group having 1 to 20 carbon atoms, a cycloalkyl group having 3 to 20 ring carbon atoms, an aryl group having 6 to 18 ring carbon atoms, or a heteroaryl group having 5 to 18 ring atoms.

In preferred embodiments of the material for organic EL device of the invention,
(1) $G_{16}$ represents a carbon atom bonded to $L_1$;
(2) $L_1$ represents a single bond, an arylene group having 6 to 18 ring carbon atoms, or a heteroarylene group having 5 to 18 ring atoms, provided that a divalent residue of dibenzofuran and a divalent residue of dibenzothiophene are excluded, particularly $L_1$ represents a phenylene group;
(3) $L_2$ represents a single bond, an oxygen atom, an arylene group having 6 to 18 ring carbon atoms, or a heteroarylene group having 5 to 18 ring atoms;
(4) $X_1$ represents a sulfur atom or a oxygen atom, particularly represents an oxygen atom;
(5) each of $G_{26}$ and $G_{33}$ represents a carbon atom bonded to $L_2$;
(6) at lease one of $G_{31}$ to $G_{38}$ and $G_{41}$ to $G_{48}$ represents a nitrogen atom;
(7) $L_2$ represents an alkylene group having 1 to 20 carbon atoms, a cycloalkylene group having 3 to 20 ring carbon atoms, an oxygen-containing divalent linking group, a silicon-containing divalent linking group, a phosphorus-containing divalent linking group, or a sulfur-containing divalent linking group.

Specific examples of the material for organic EL device represented by formula (1) are shown below, although not limited to thereto. The substituents in the following specific examples are incorporated into the preferred substituents of the material.

H-1
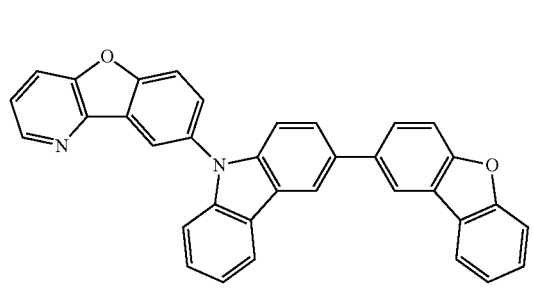
H-2
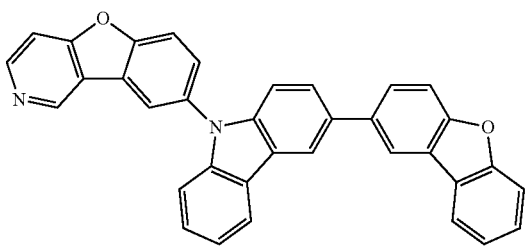
H-3
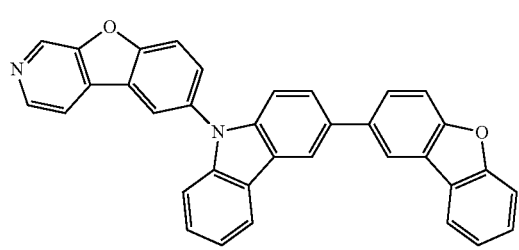
H-4
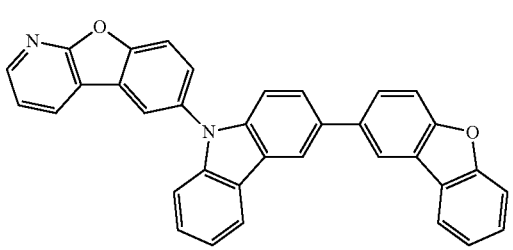
H-5
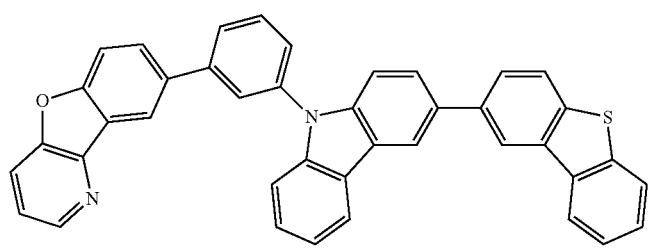
H-6
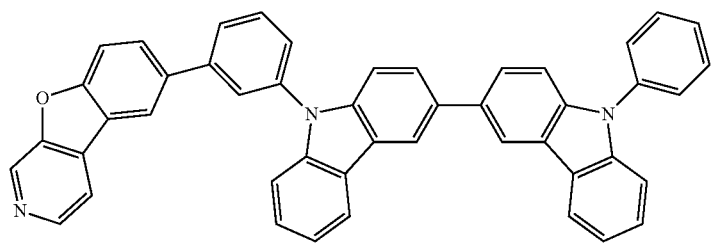
H-7
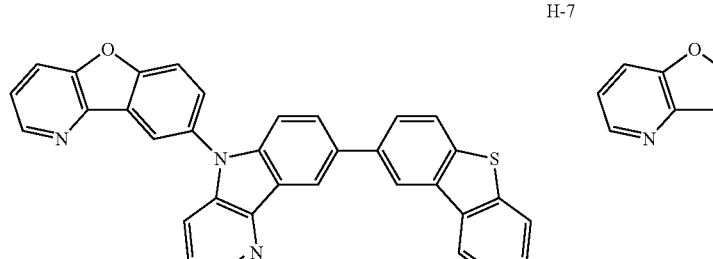
H-8
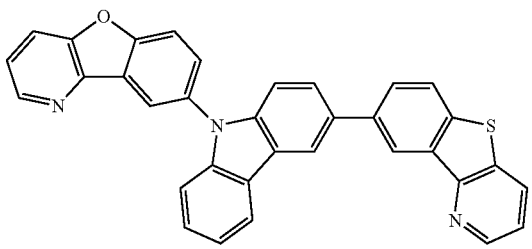
H-9
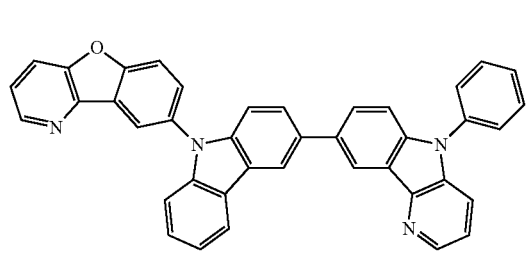
H-10
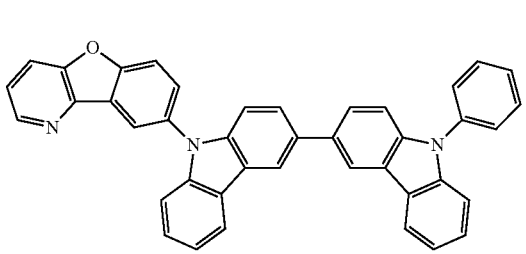

H-11
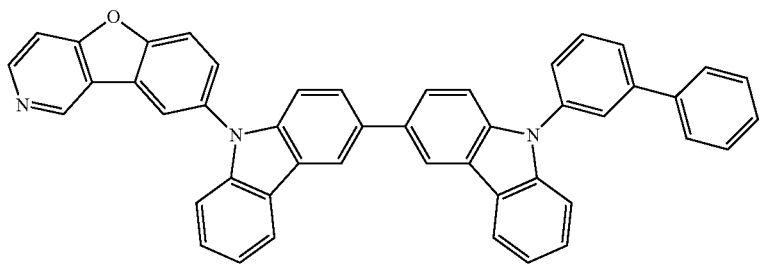
H-12
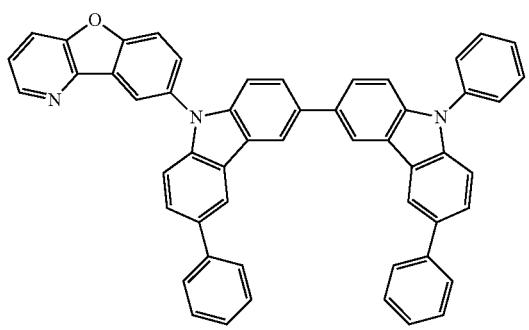
H-13
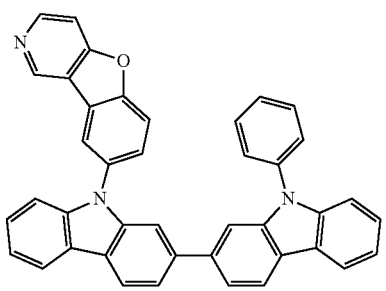
H-14
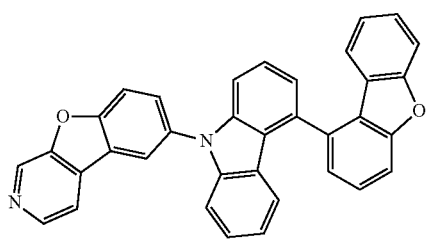
H-15
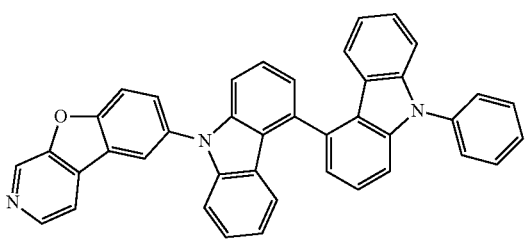
H-16
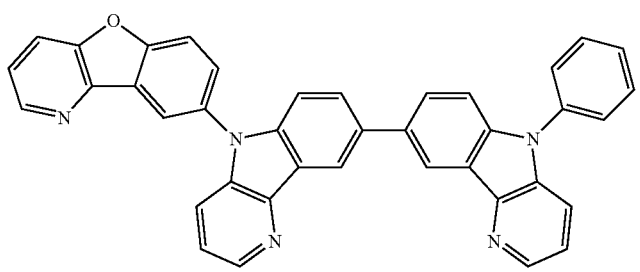
H-17
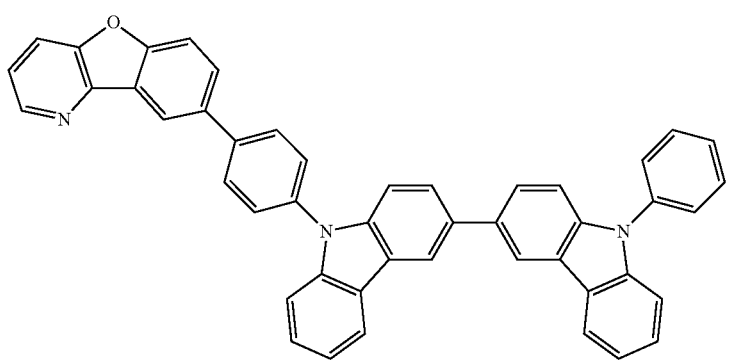

-continued
H-18
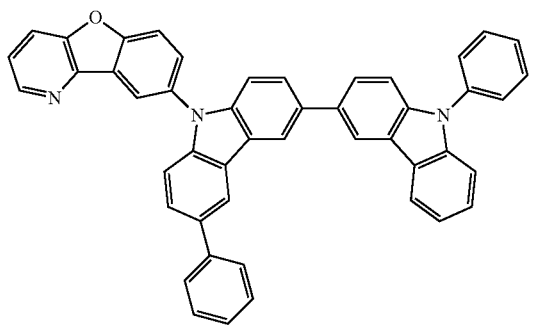
H-19
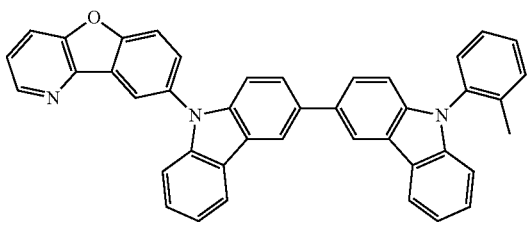
H-20
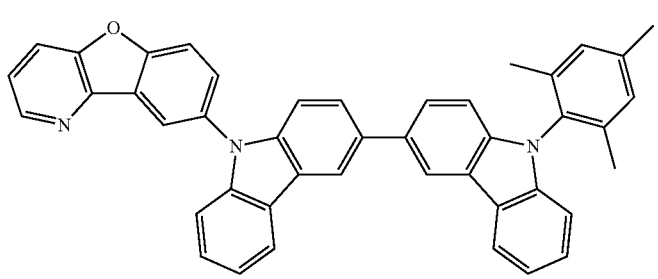
H-21
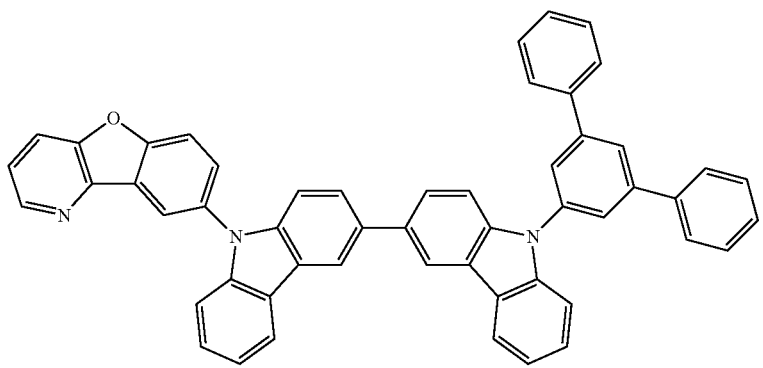
H-22
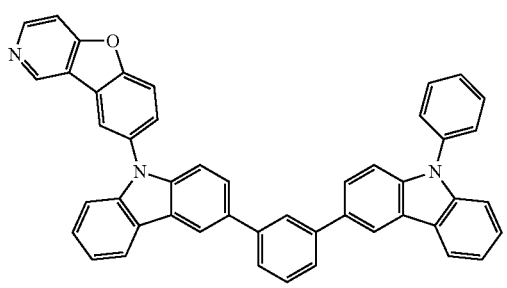
H-23
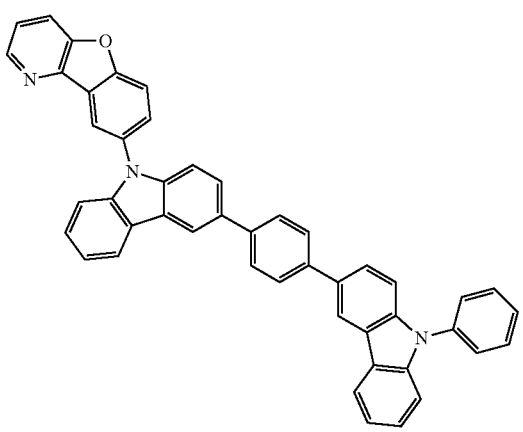

-continued
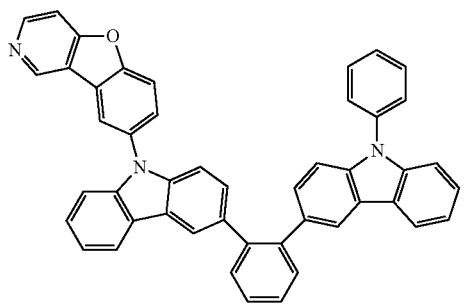
H-24
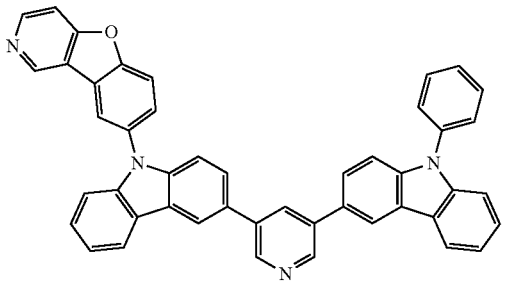
H-25
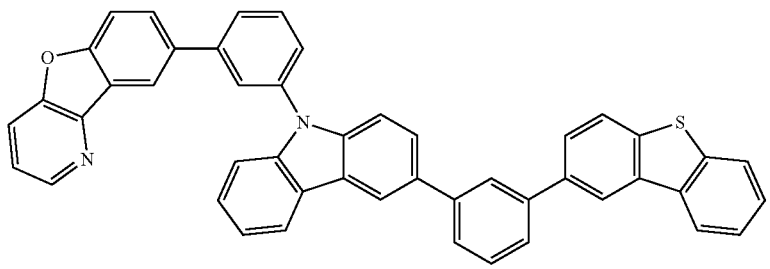
H-26
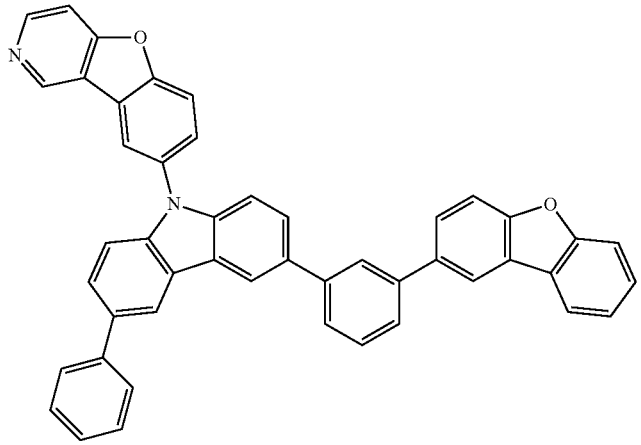
H-27
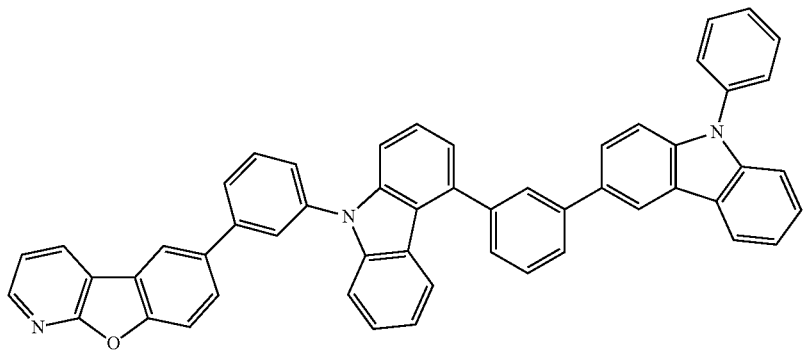
H-28

-continued
H-29
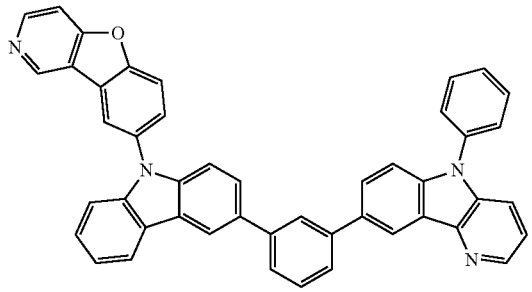
H-30
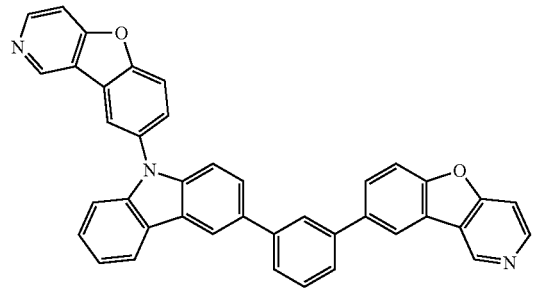
H-31
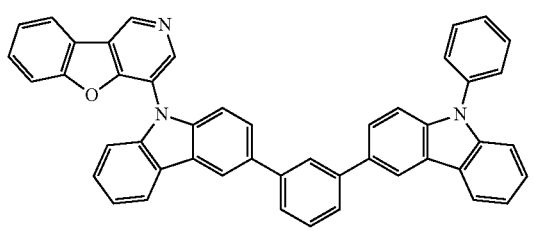
H-32
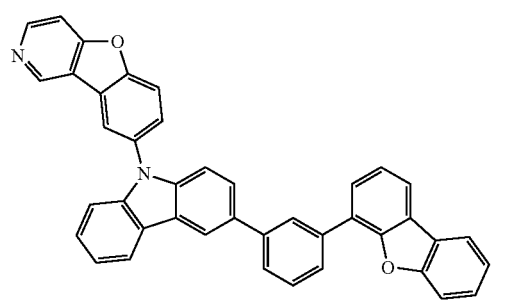
H-33
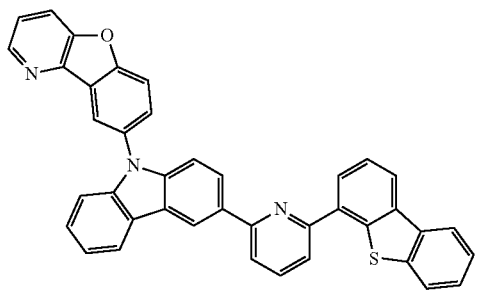
H-34
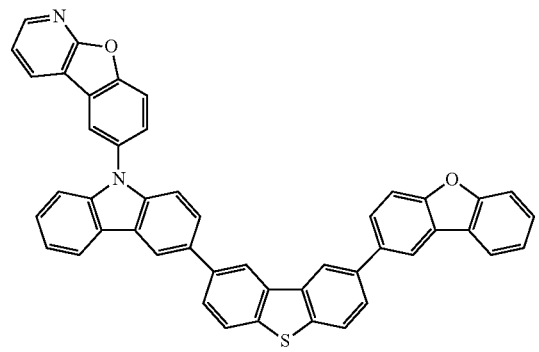
H-35
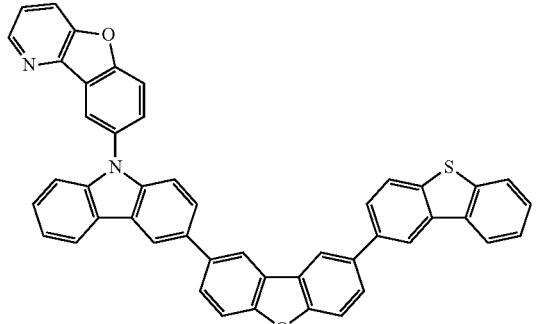
H-36
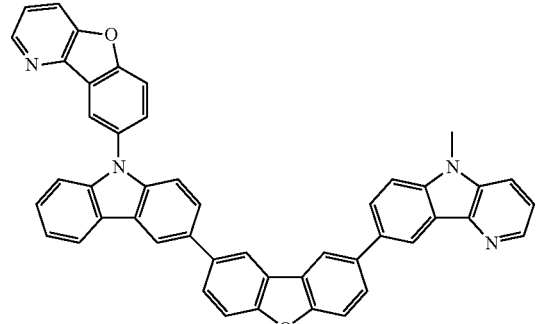
H-37
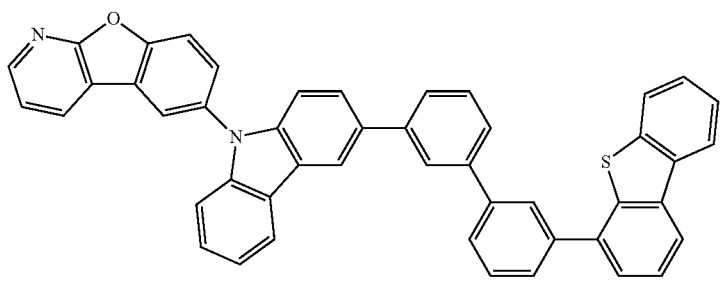

-continued
H-38
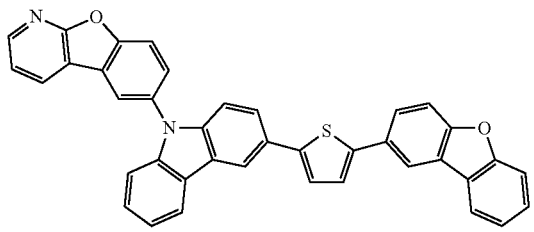
H-39
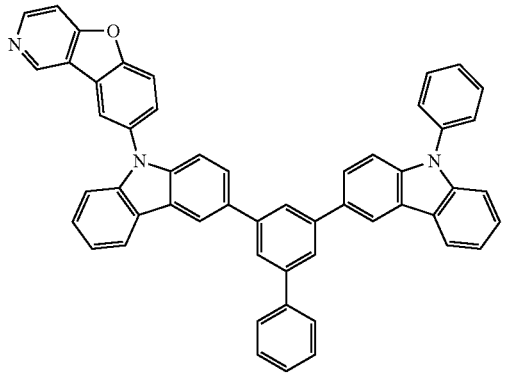
H-40
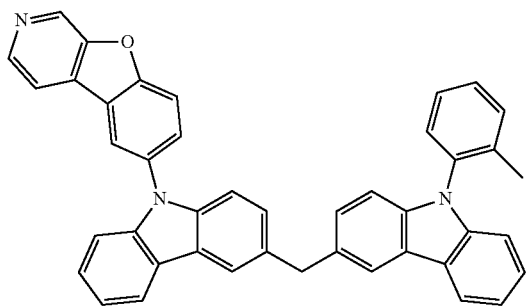
H-41
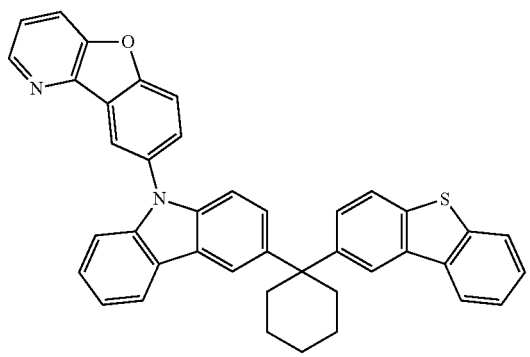
H-42
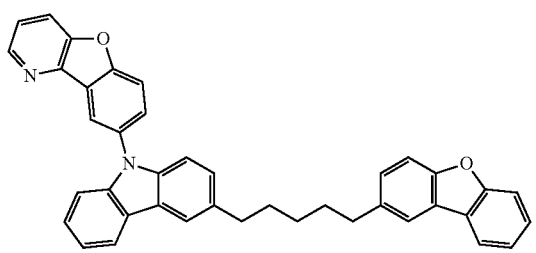
H-43
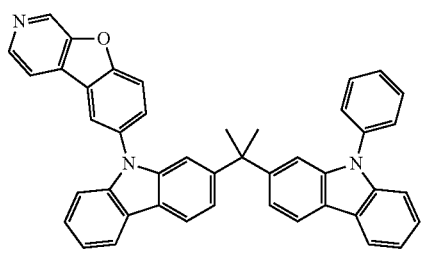
H-44
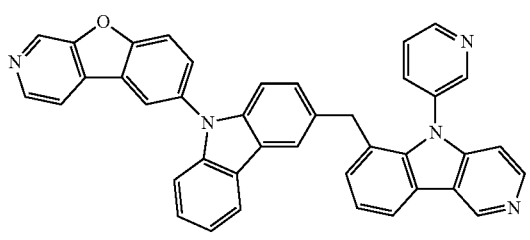
H-45
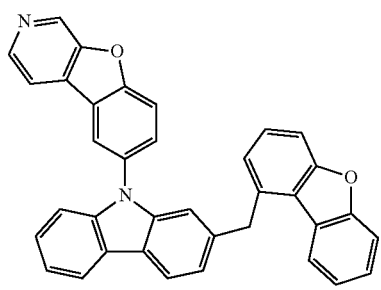

-continued
H-46
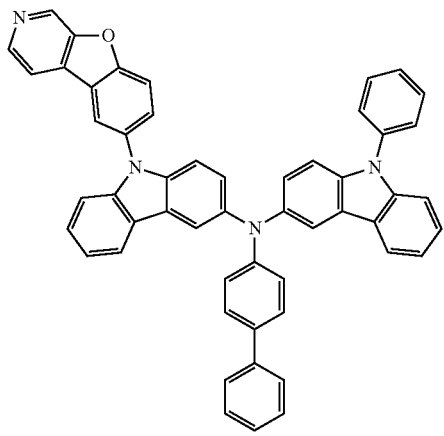
H-47
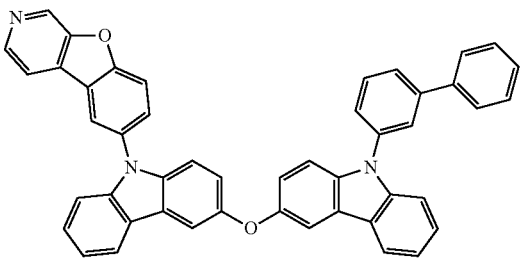
H-48
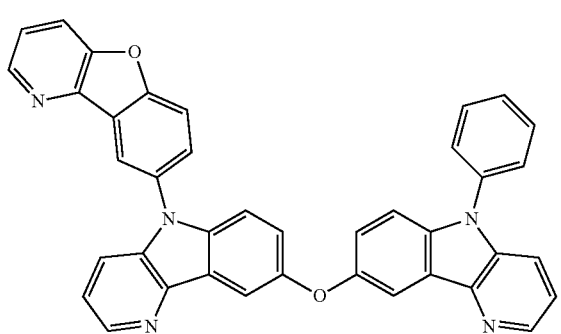
H-49
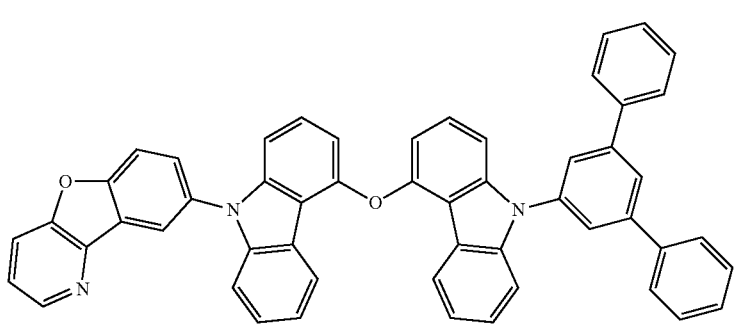
H-50
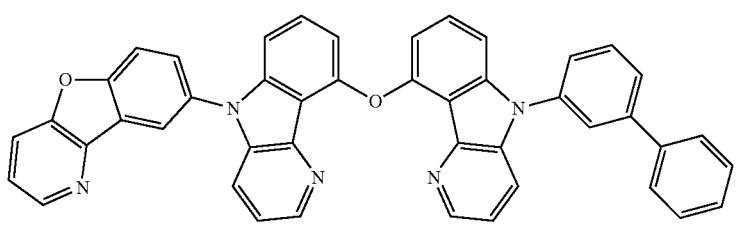

-continued
H-51
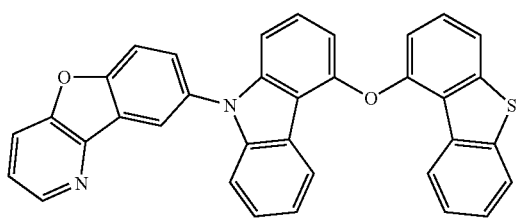
H-52
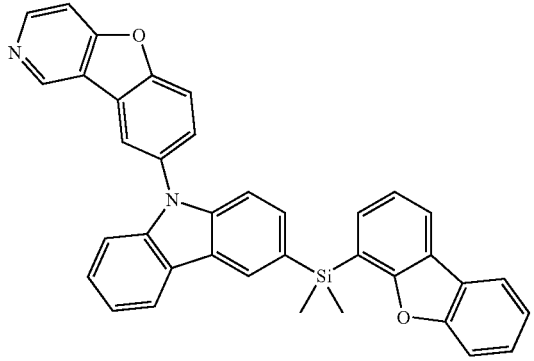
H-53
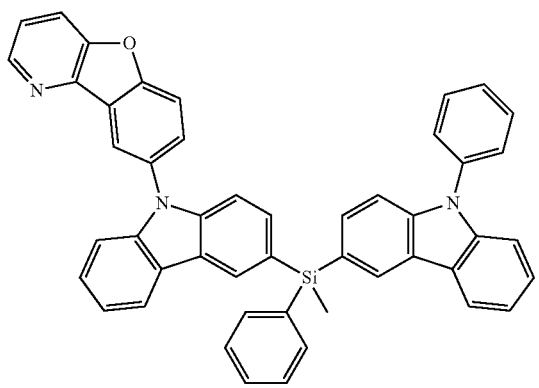
H-54
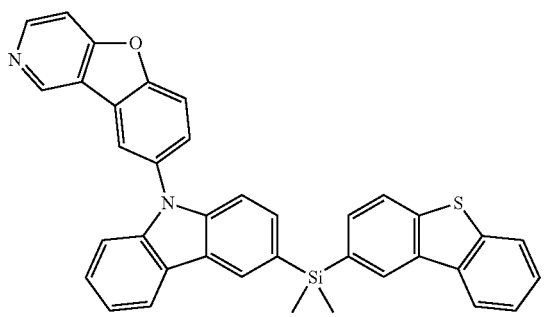
H-55
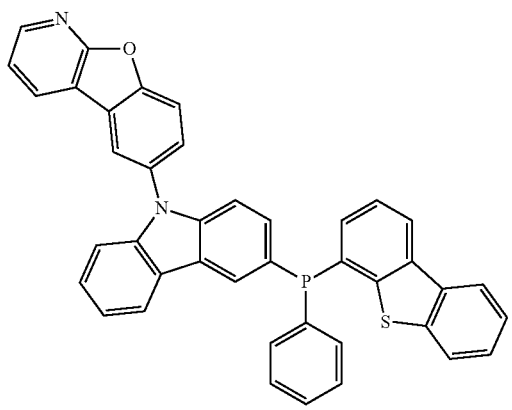
H-56
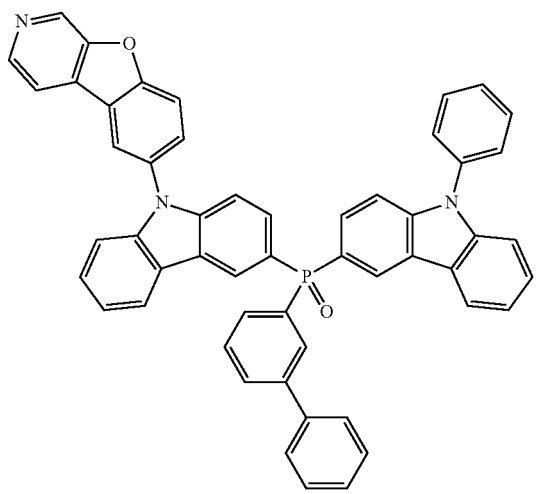
H-57
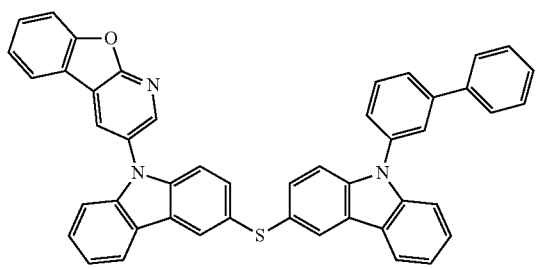
H-58
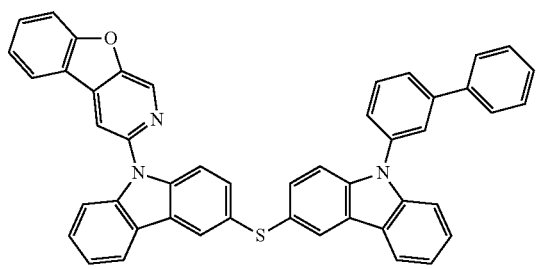

-continued
H-59
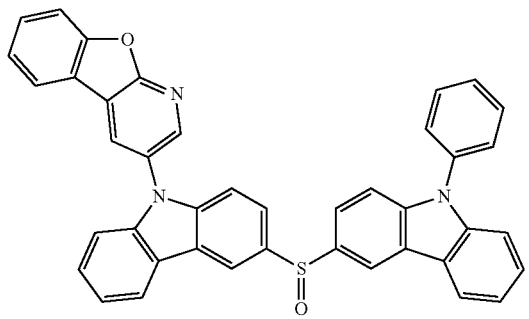
H-60
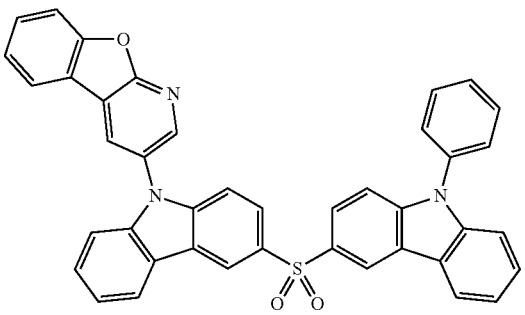
H-61
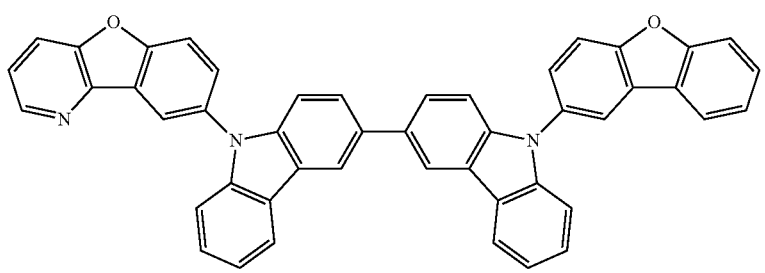
H-62
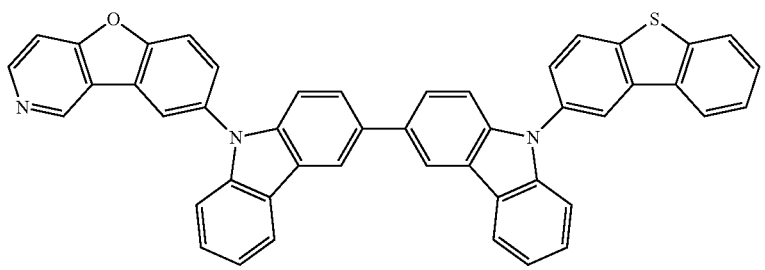
H-63
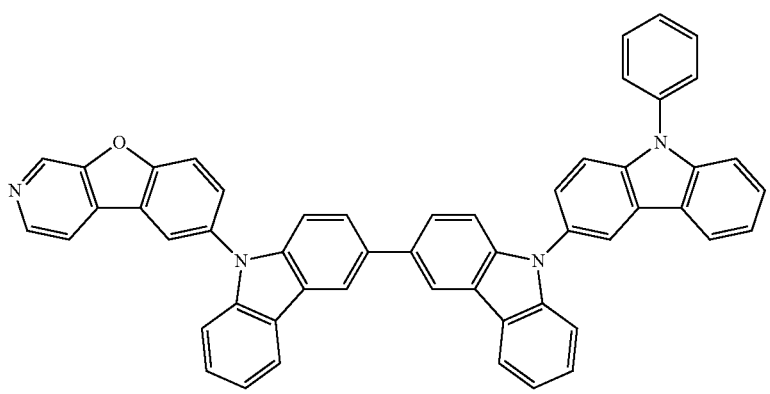
H-64
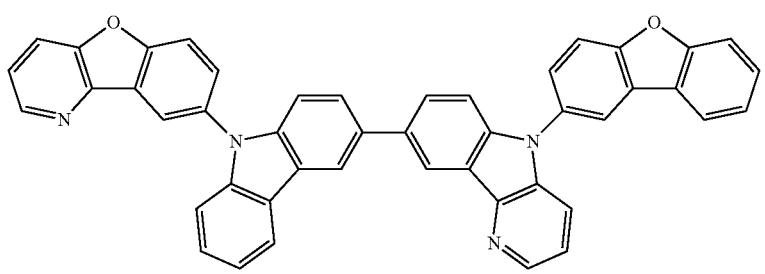

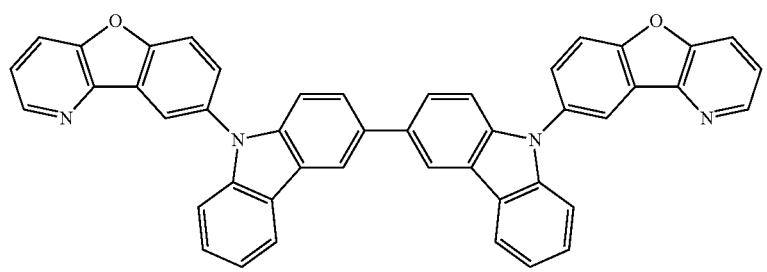
H-65
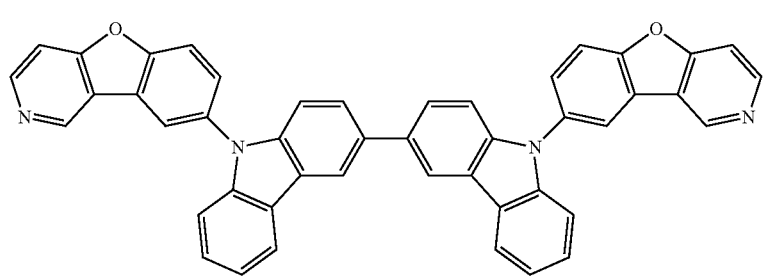
H-66
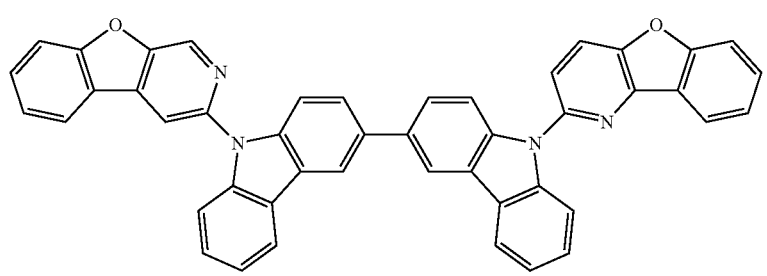
H-67
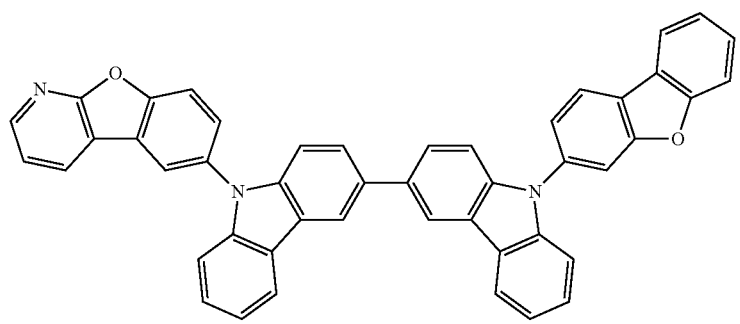
H-68
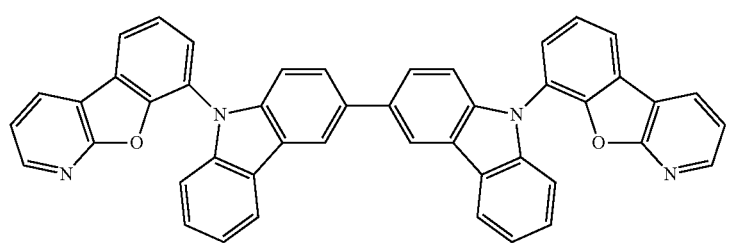
H-69

-continued
H-70
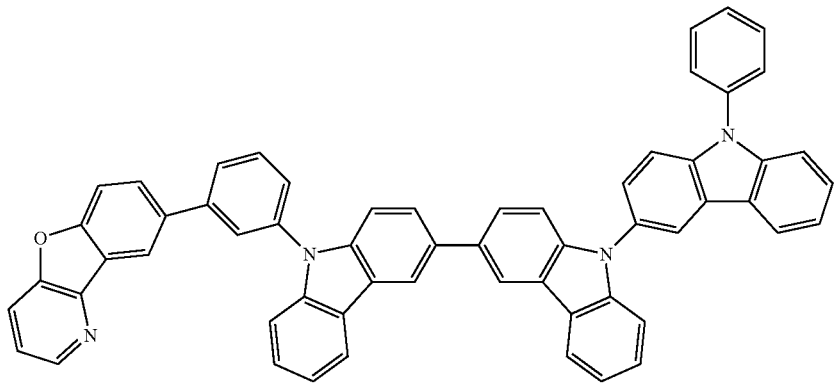
H-71
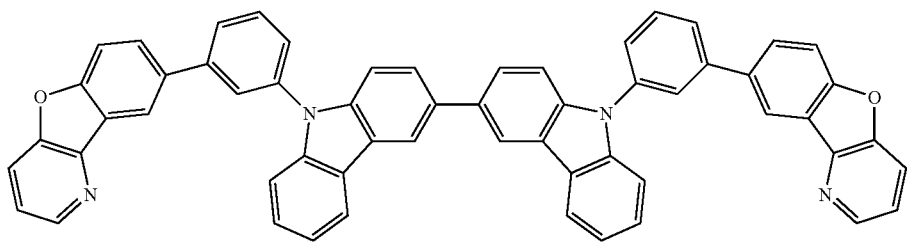
H-72
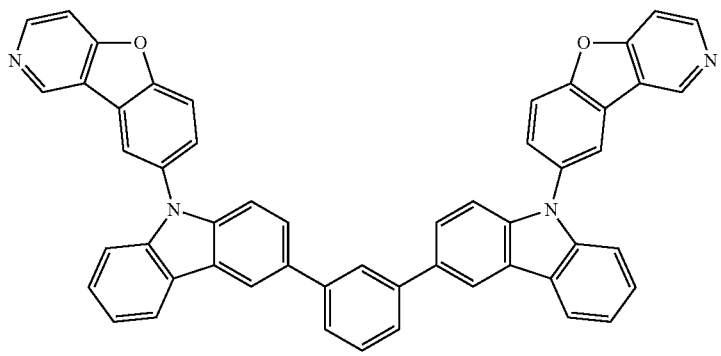
H-73
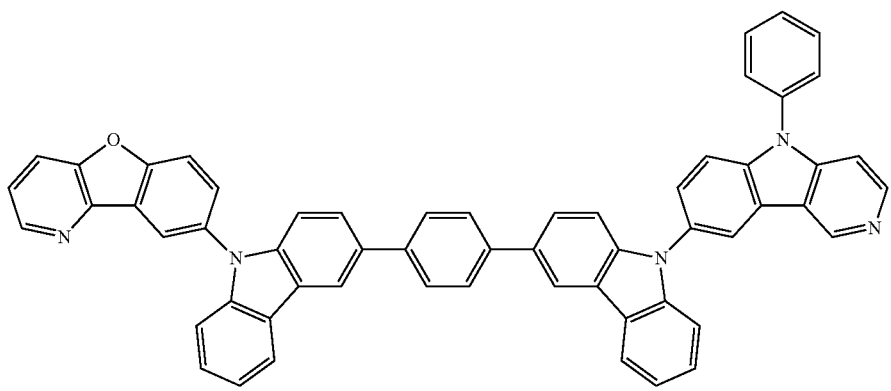

-continued
H-74
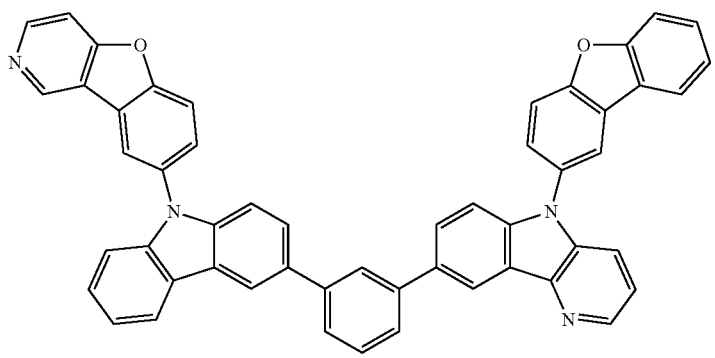
H-75
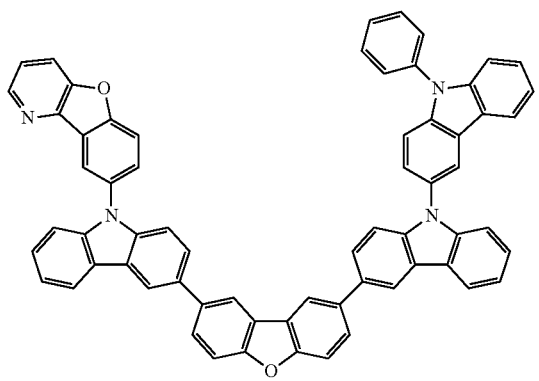
H-76
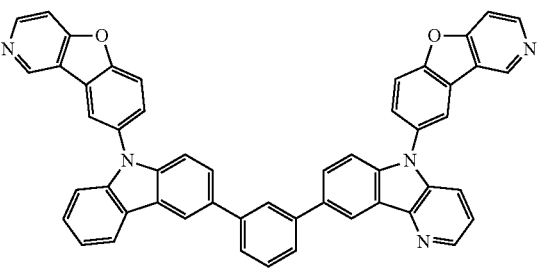
H-77
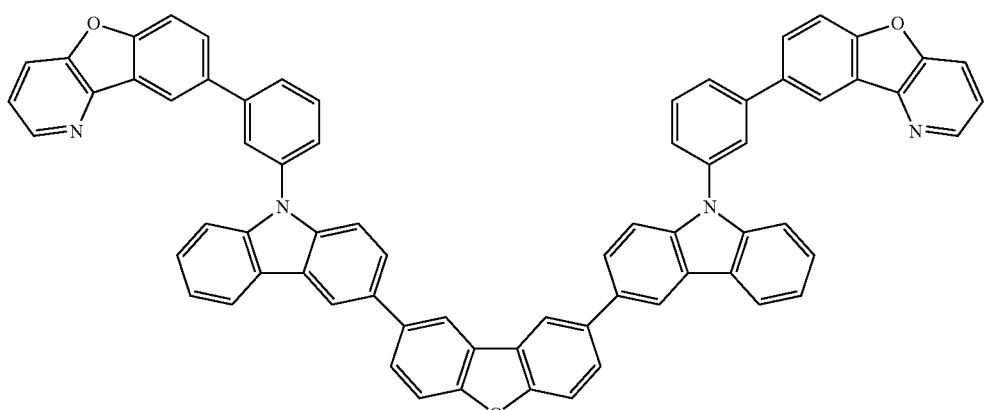
H-78
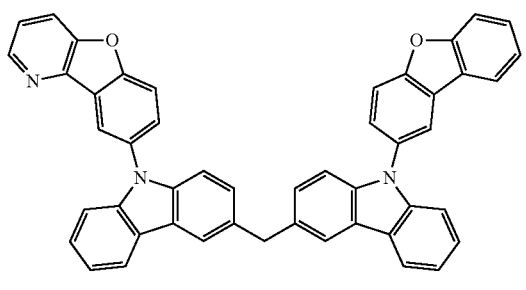
H-79
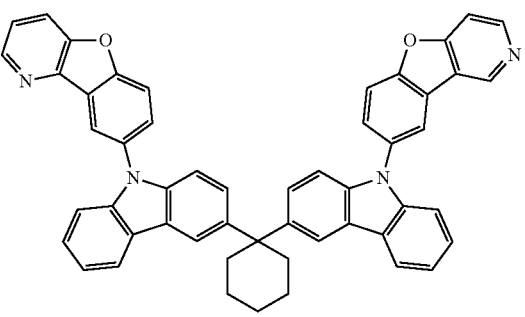

-continued
H-80
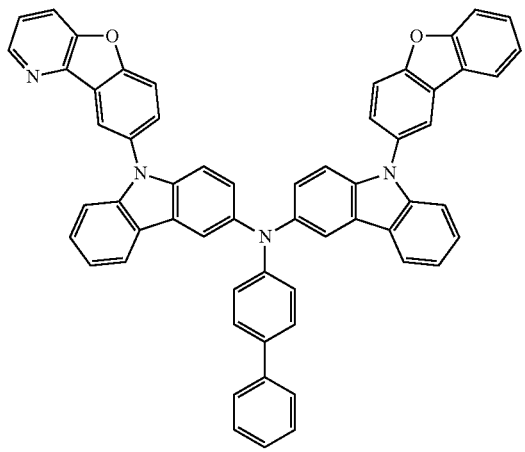
H-81
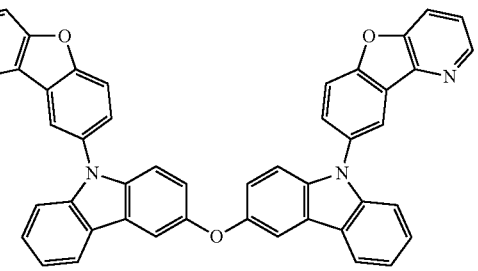
H-82
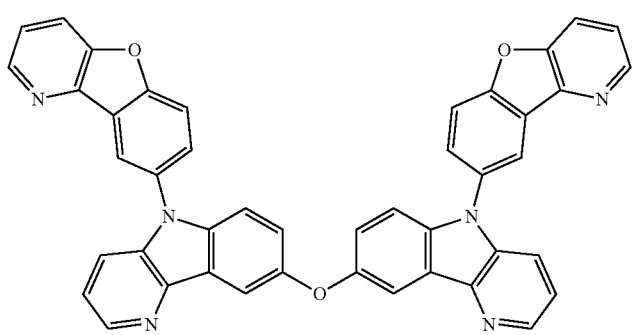
H-83
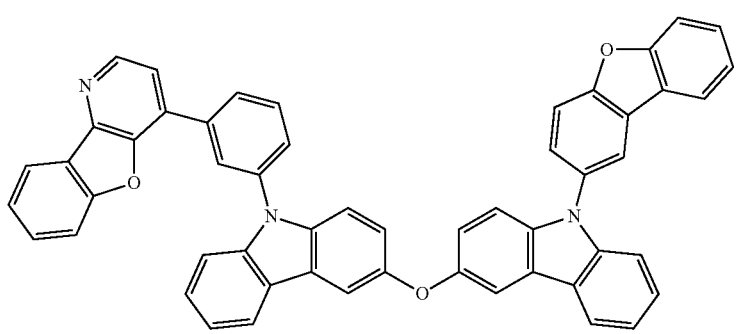
H-84
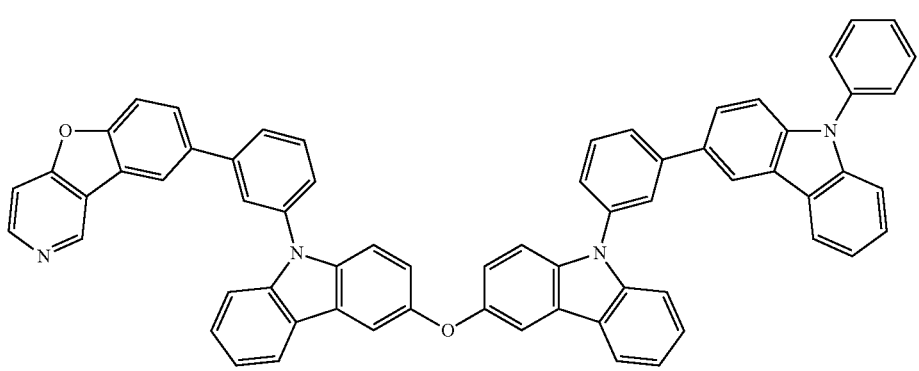

-continued
H-85
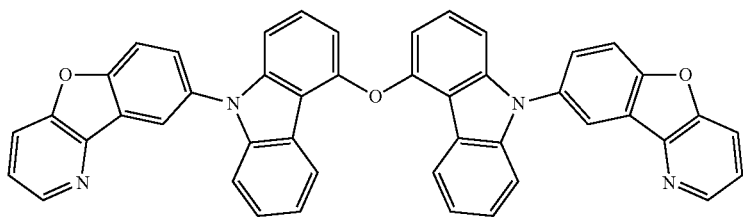
H-86
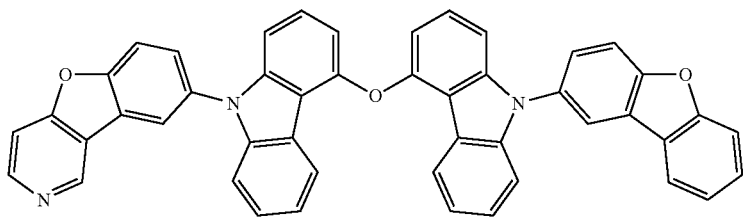
H-87
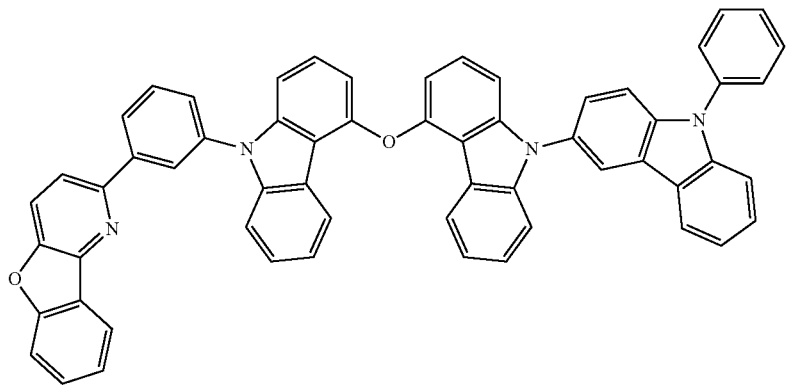
H-88
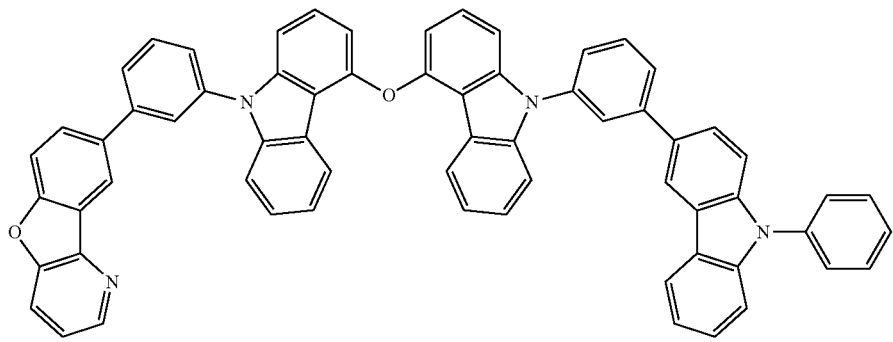
H-89
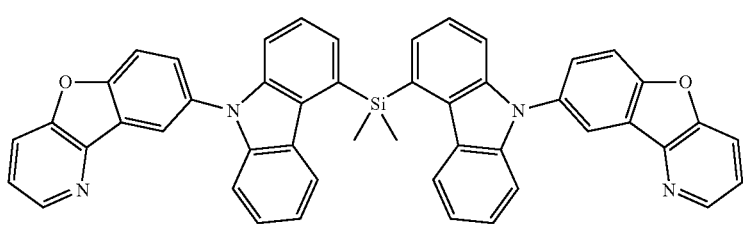

-continued
H-90
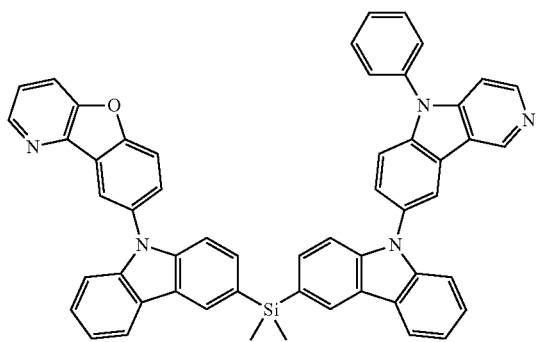
H-91
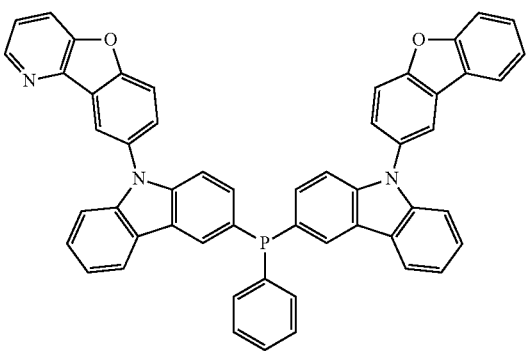
H-92
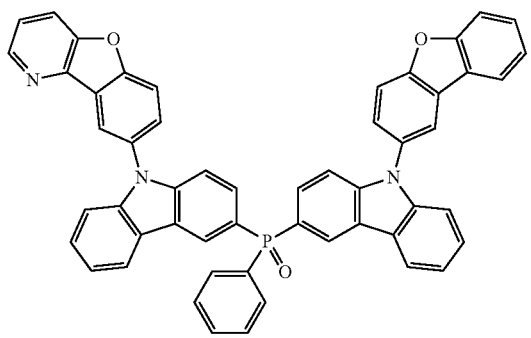
H-93
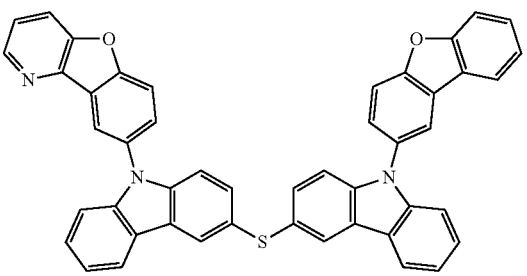
H-94
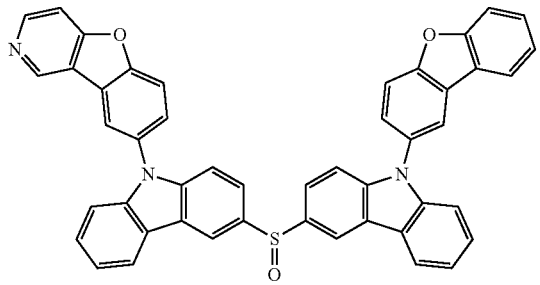
H-95
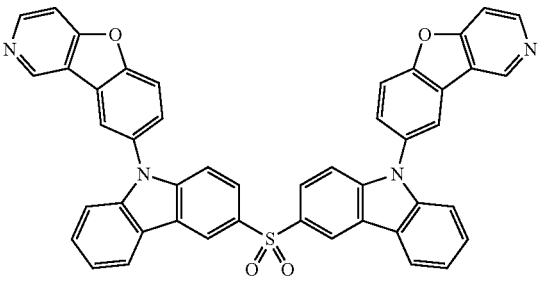
H-96
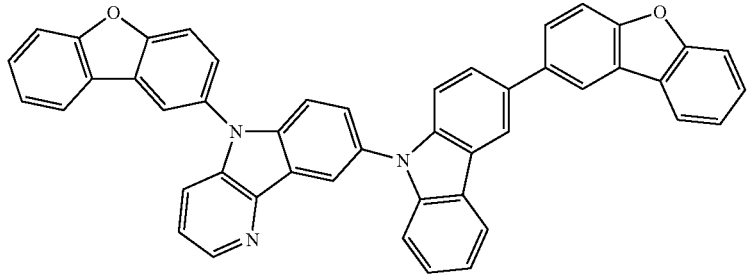
H-97
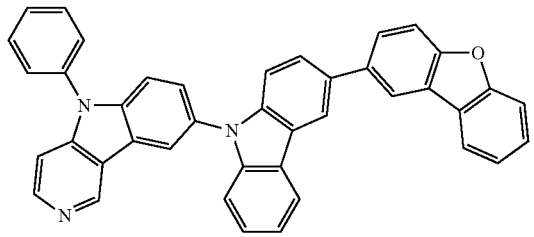
H-98
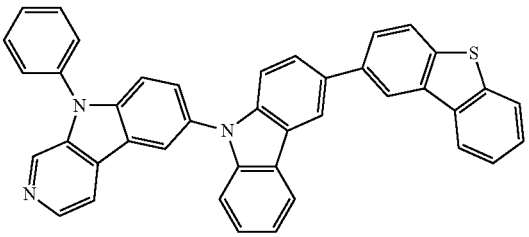

-continued
H-99
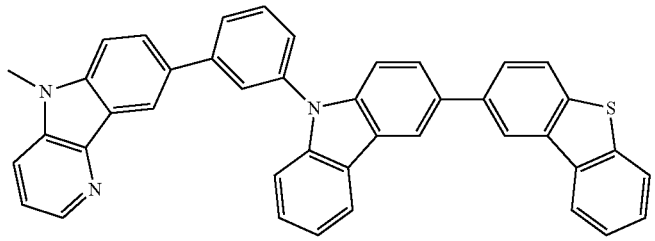
H-100
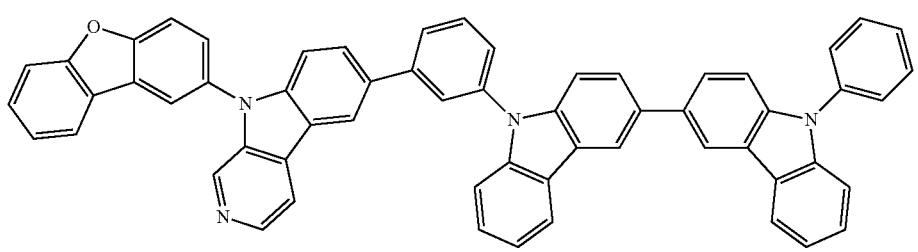
H-101
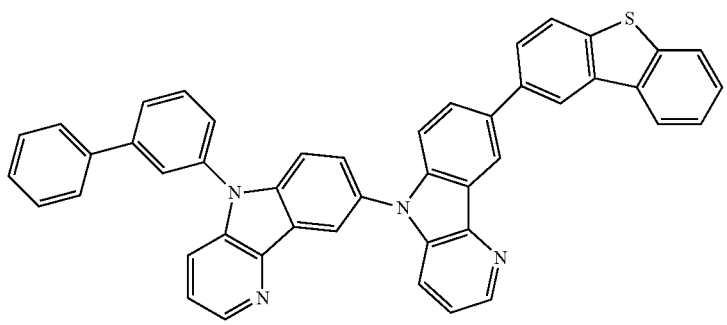
H-102
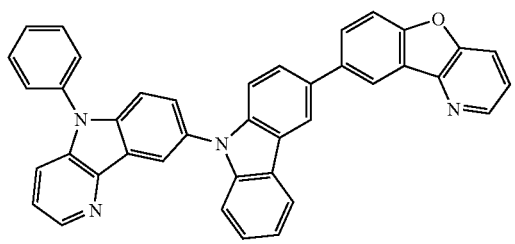
H-103
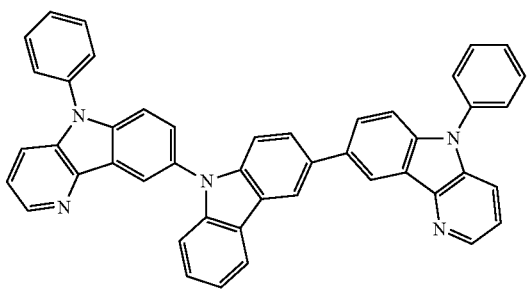
H-104
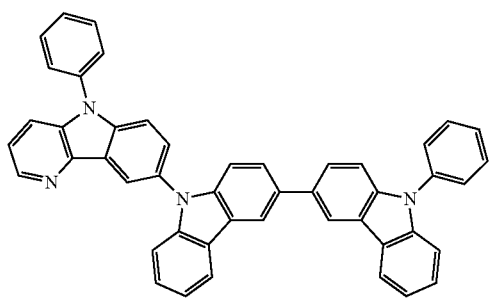
H-105
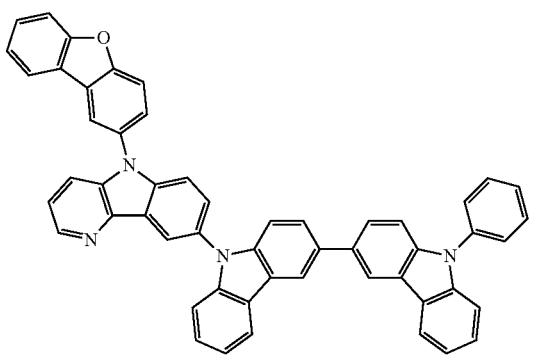

-continued
H-106
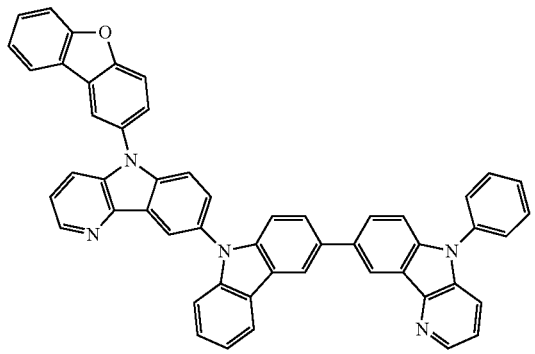
H-107
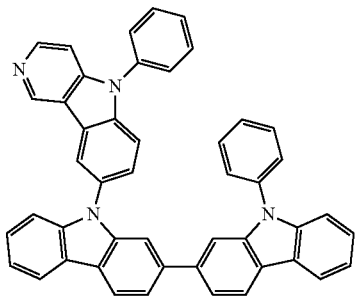
H-108
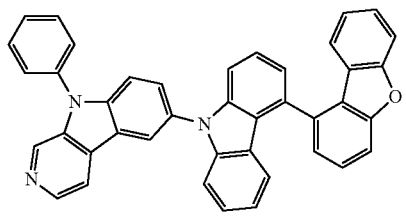
H-109
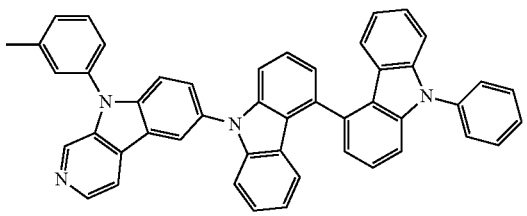
H-110
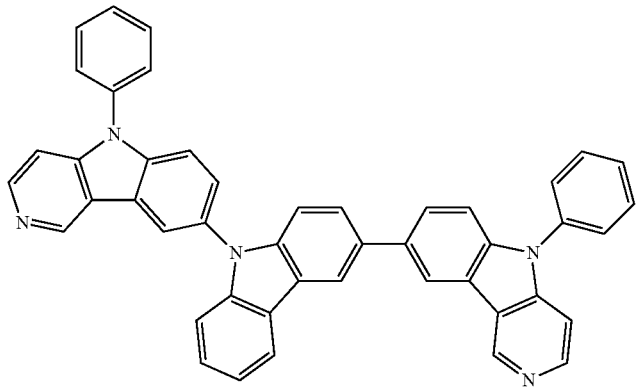
H-111
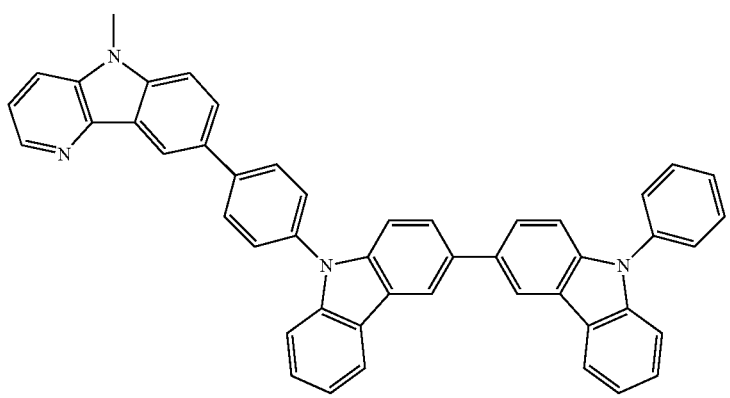

-continued
H-112
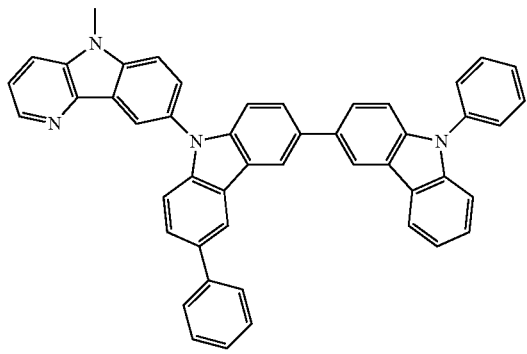
H-113
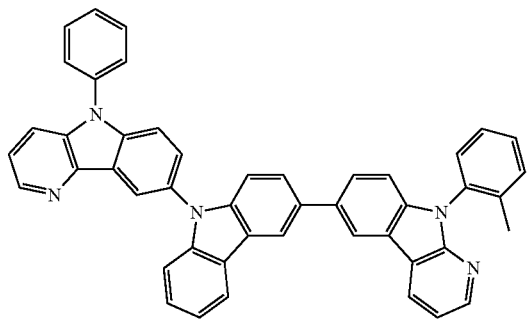
H-114
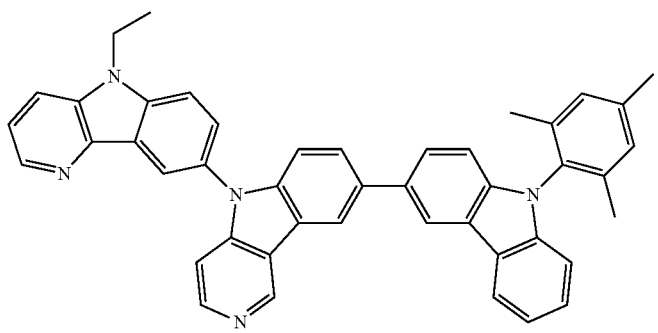
H-115
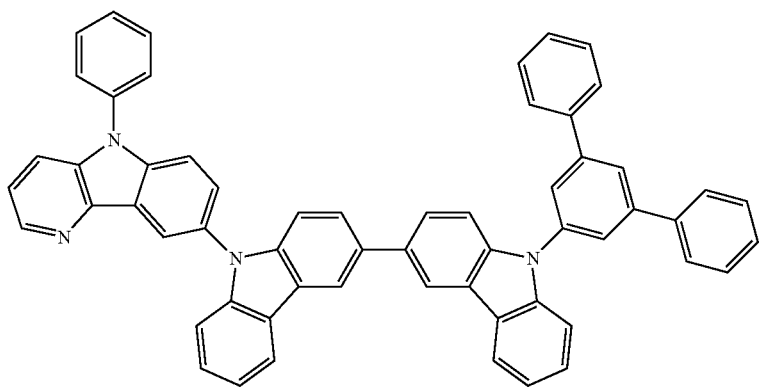
H-116
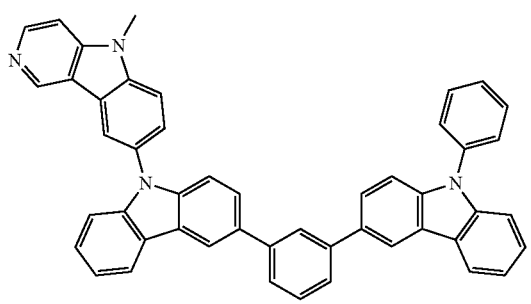
H-117
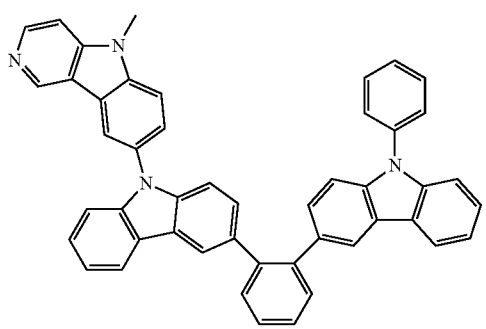

-continued
H-118
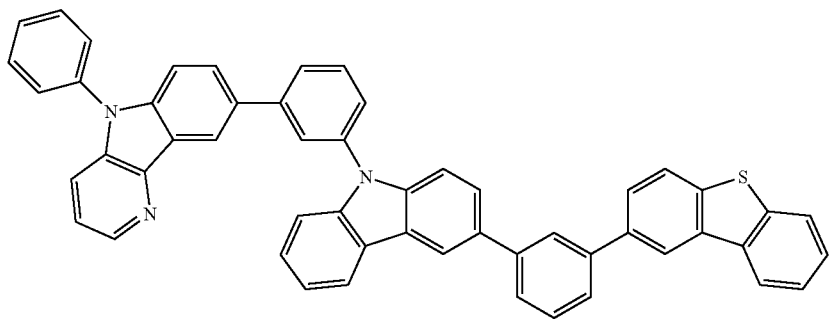
H-119
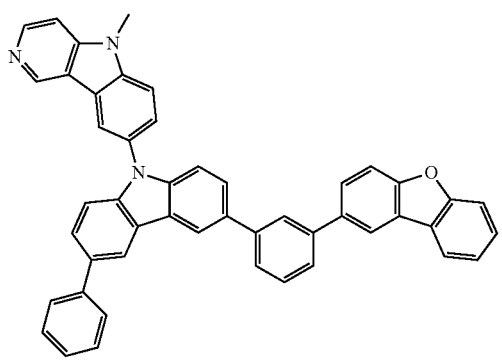
H-120
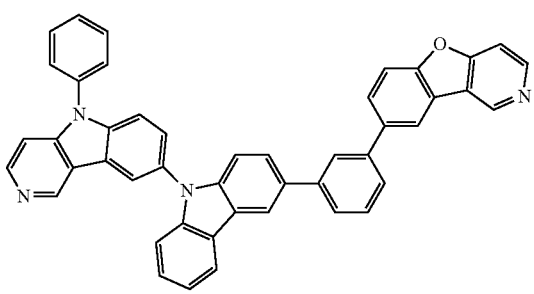
H-121
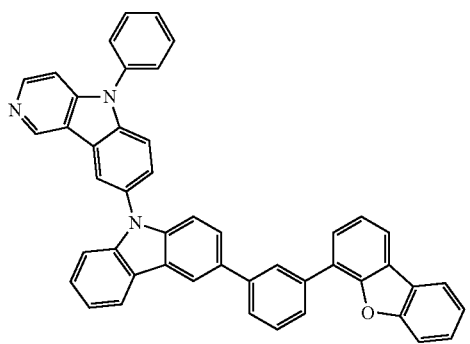
H-122
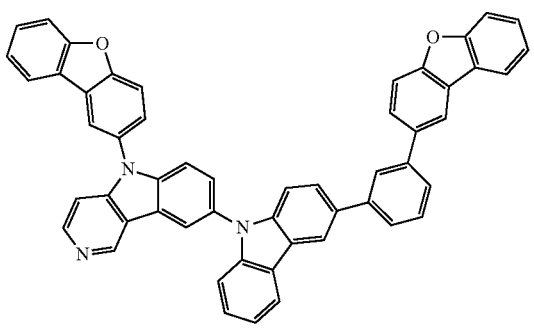
H-123
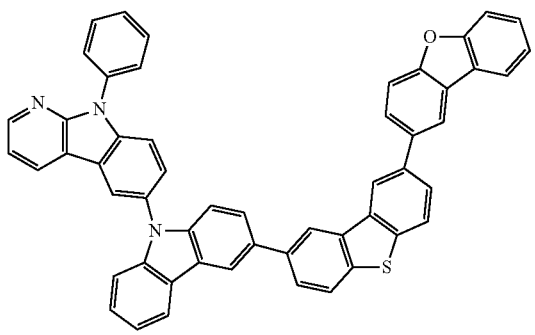
H-124
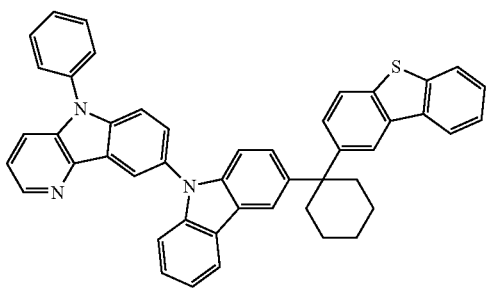

-continued
H-125
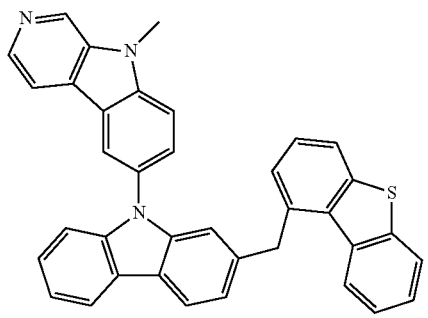
H-126
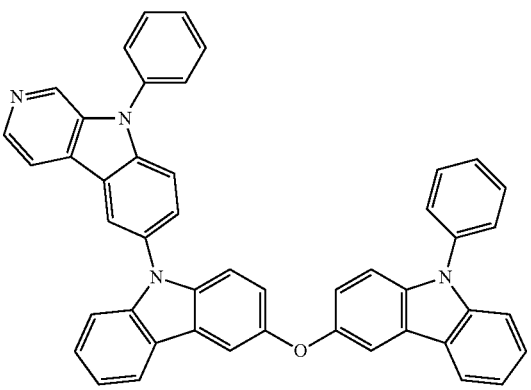
H-127
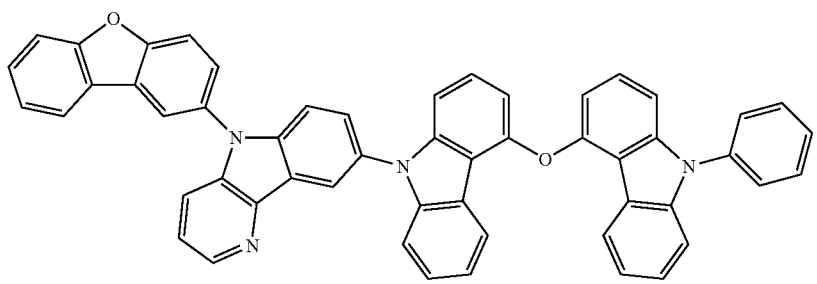
H-128
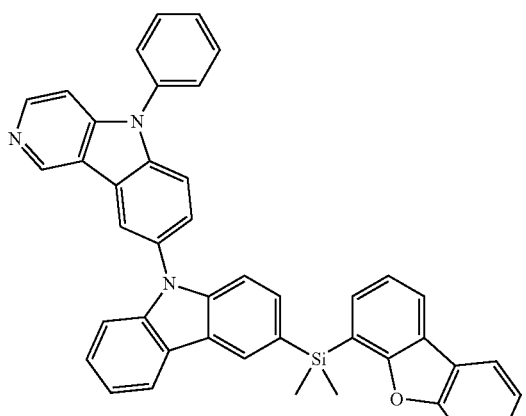
H-129
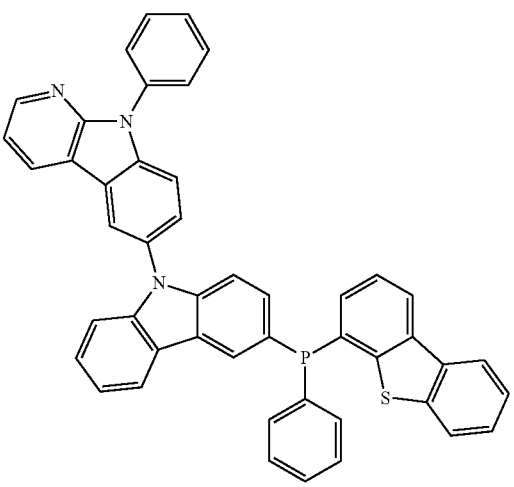
H-130
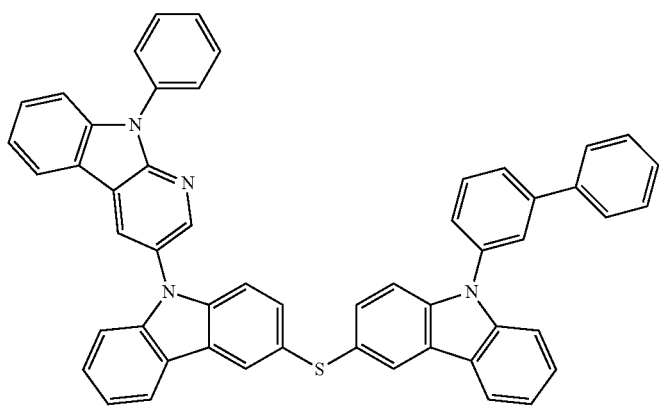

H-131
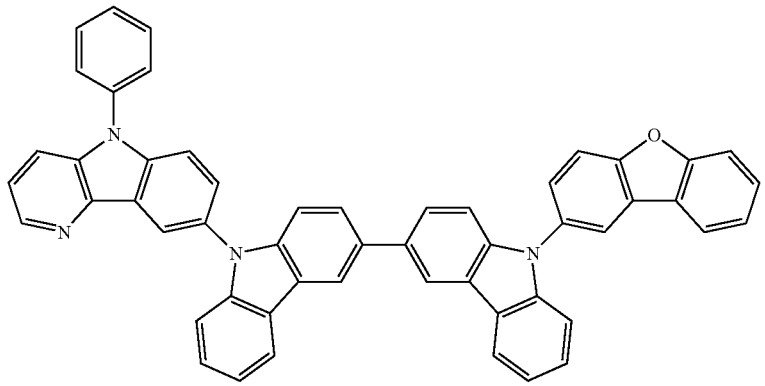
H-132
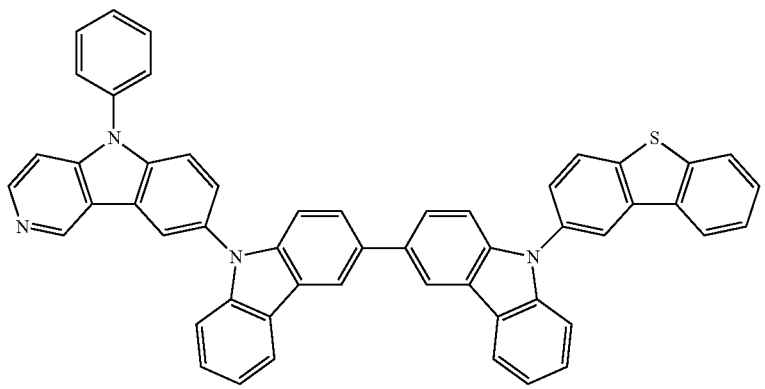
H-133
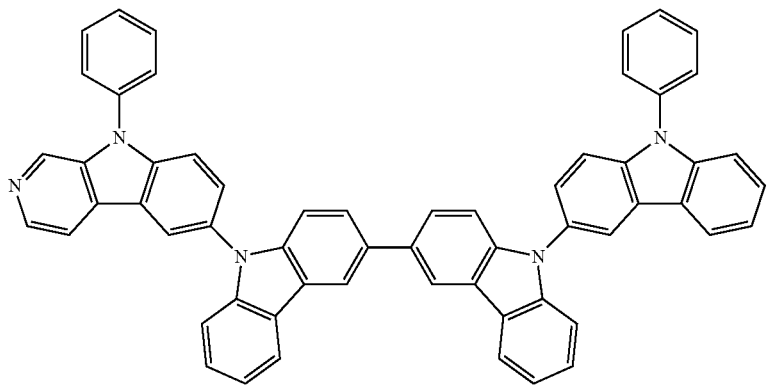
H-134
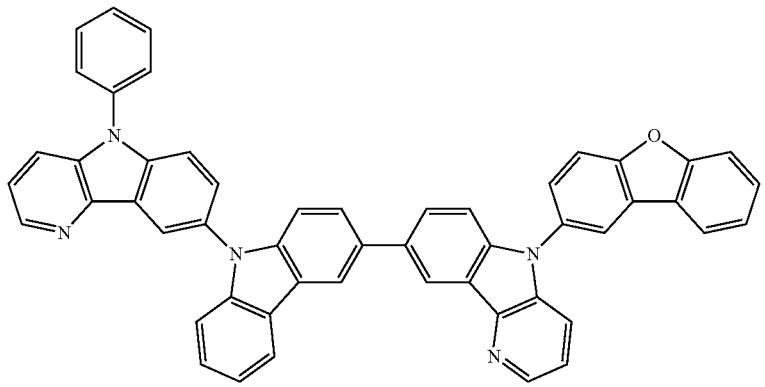

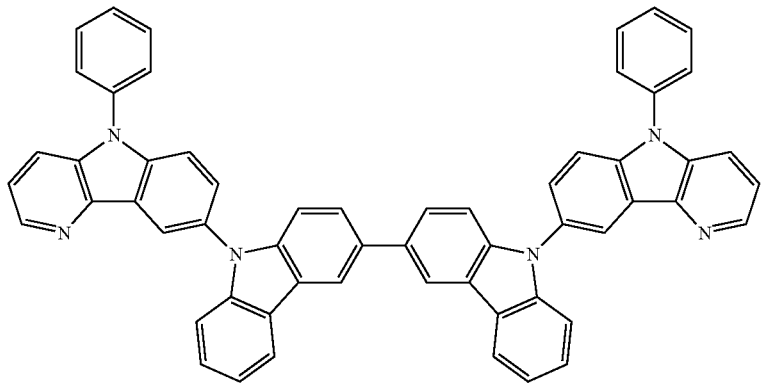
H-135
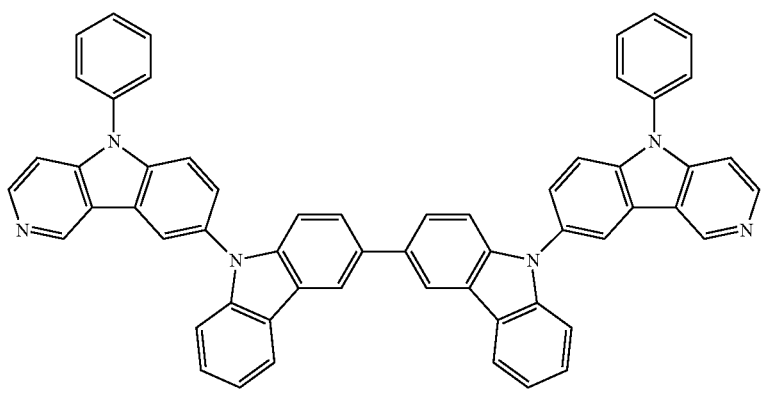
H-136
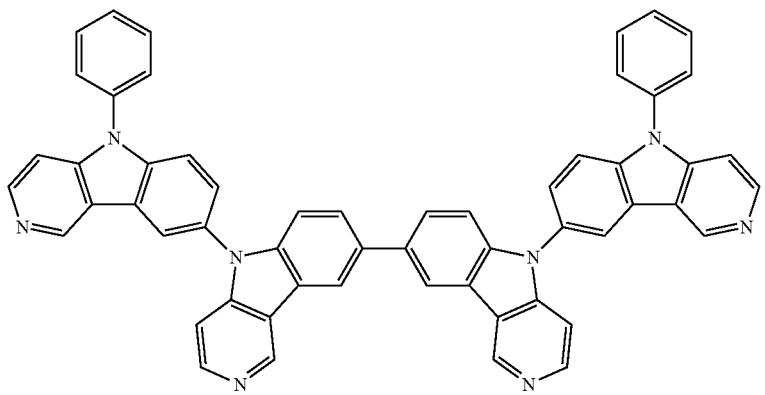
H-137
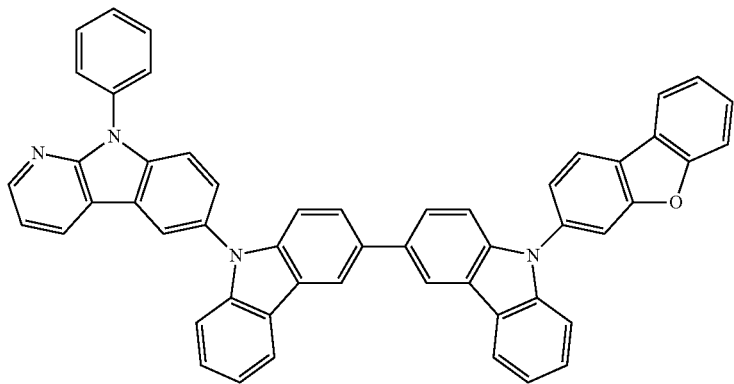
H-138

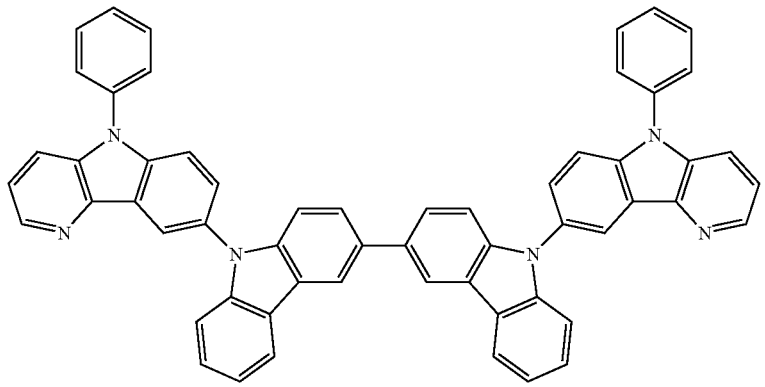
H-139
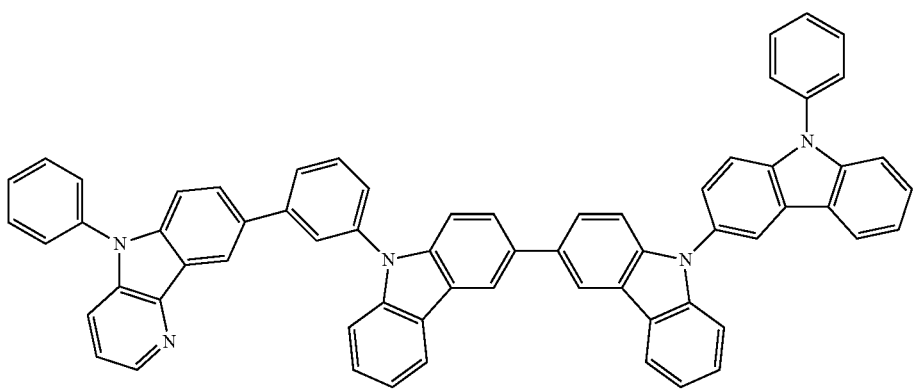
H-140
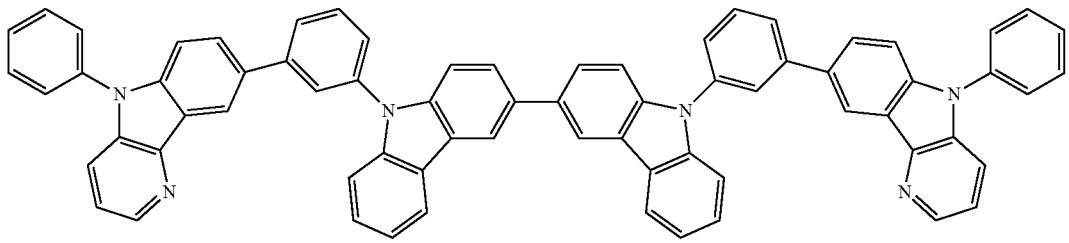
H-141
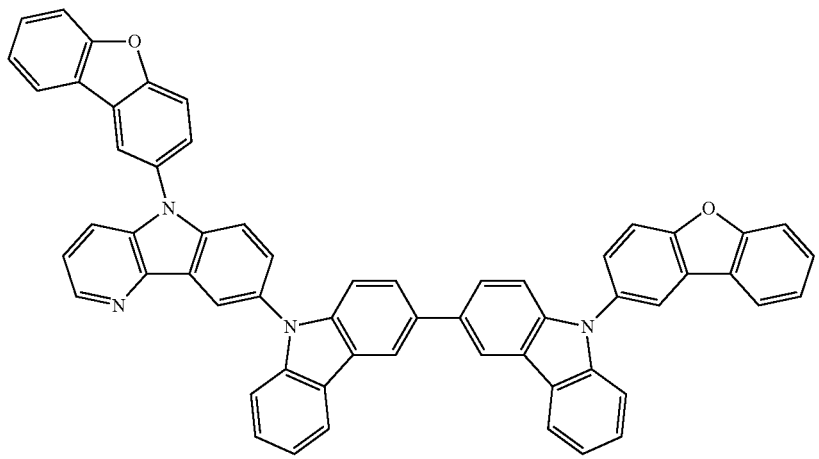
H-142

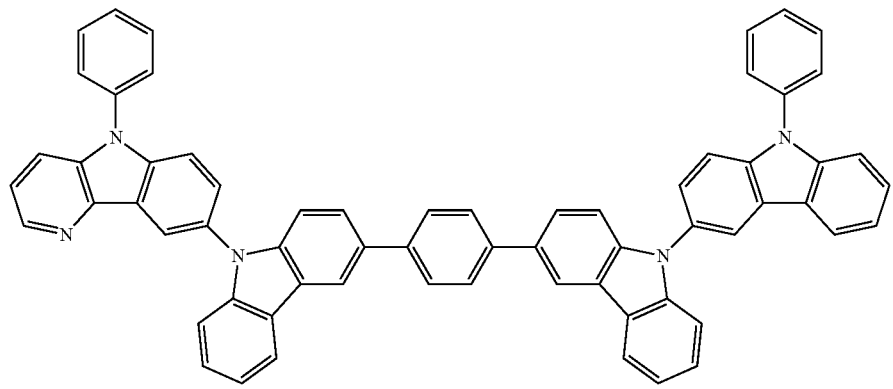
H-143
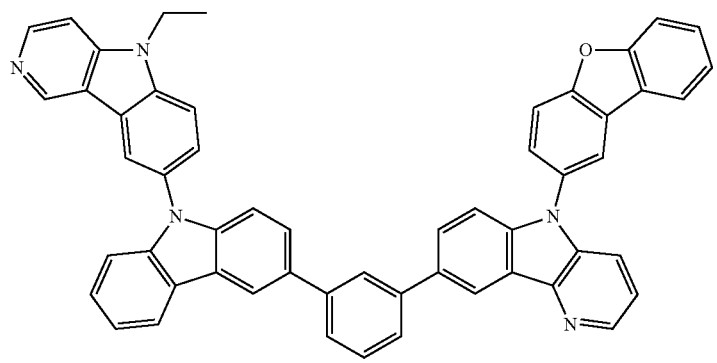
H-144
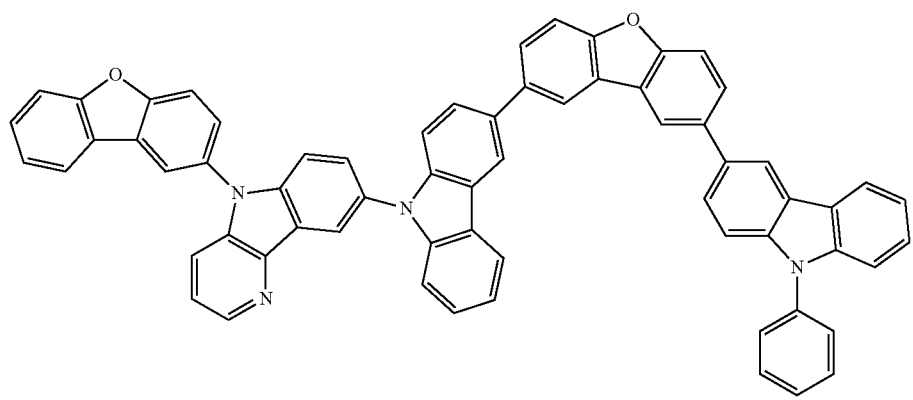
H-145
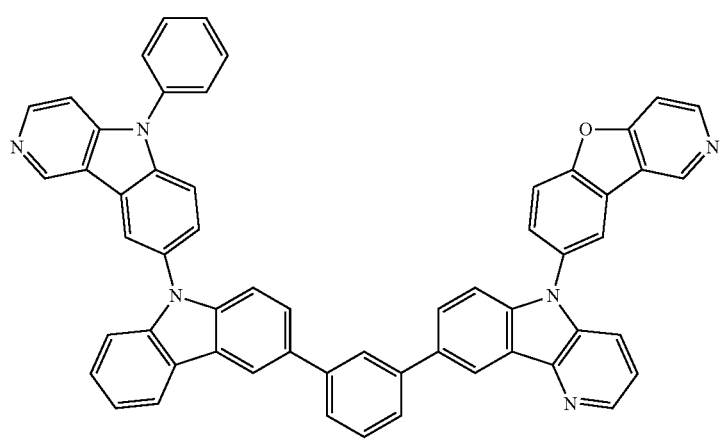
H-146

-continued
H-147
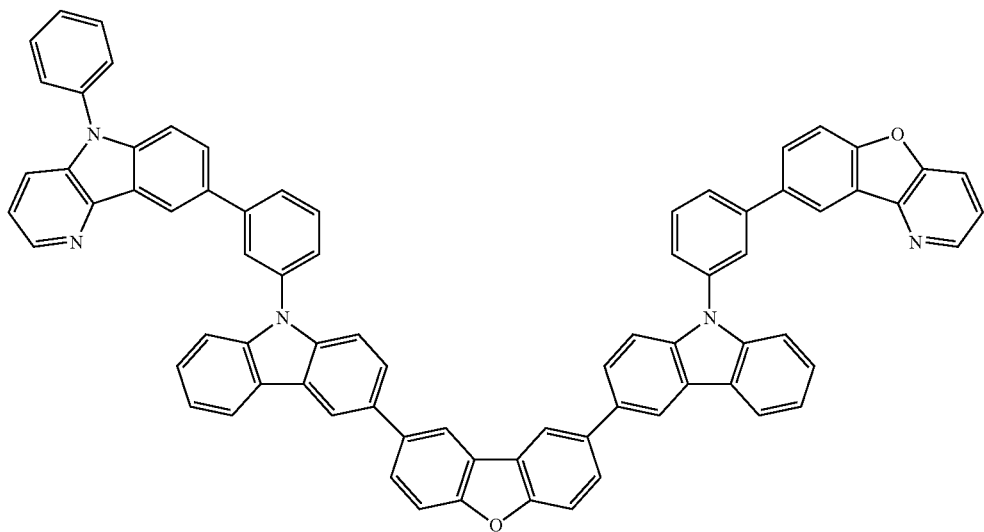
H-148
H-149
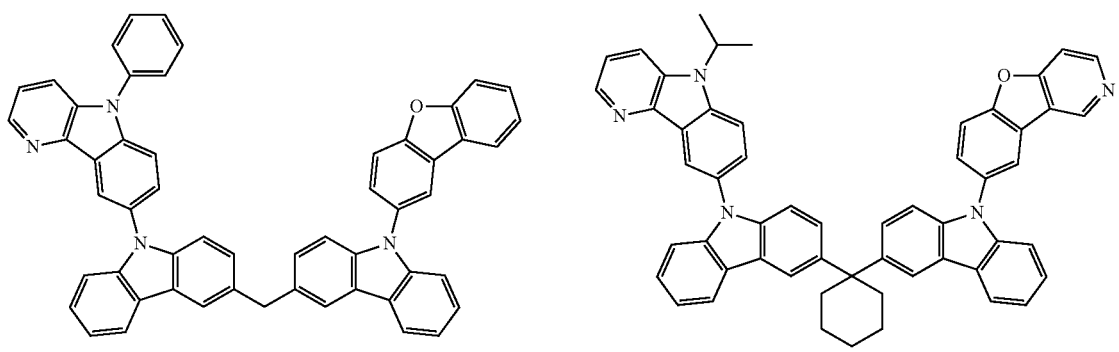
H-150
H-151
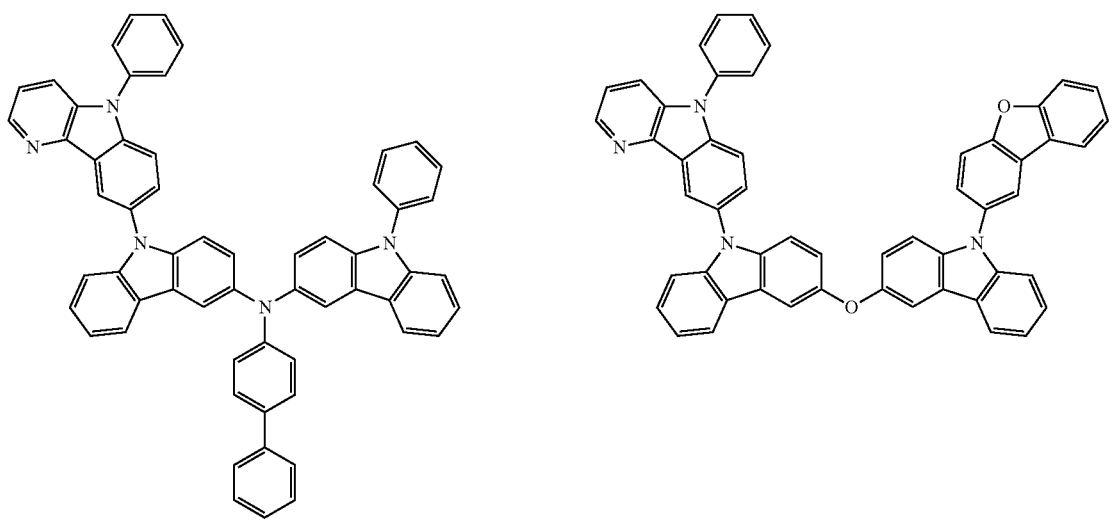

H-152
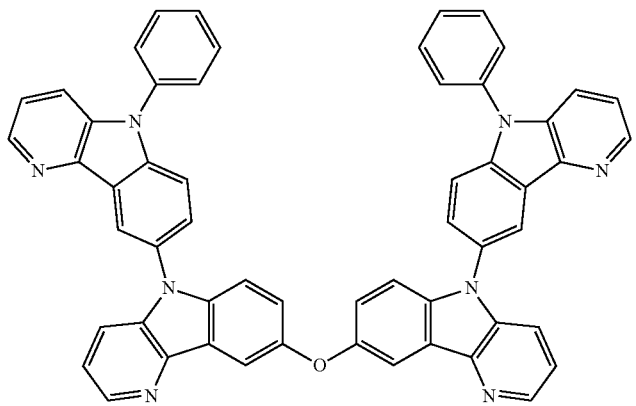
H-153
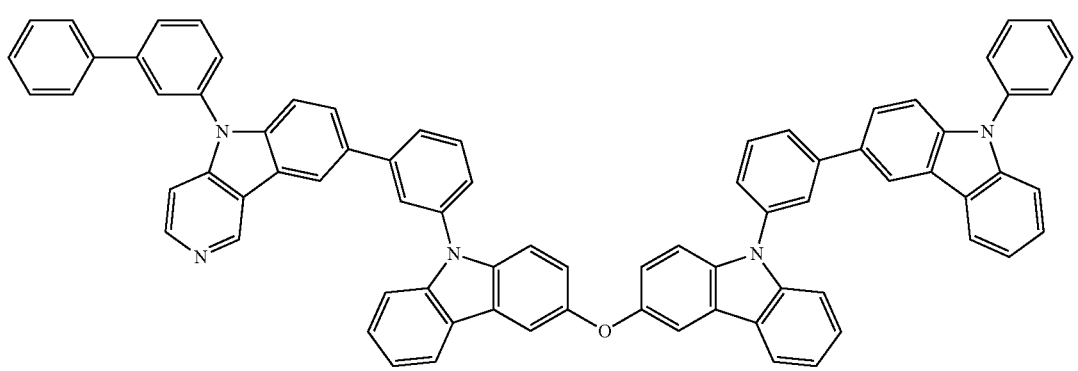
H-154
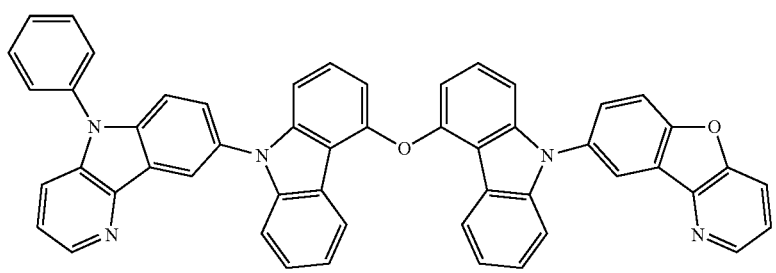
H-155
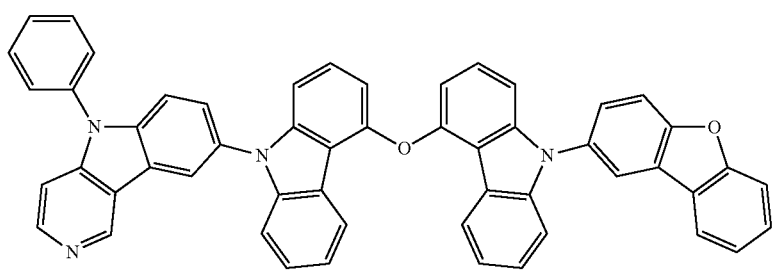

H-156
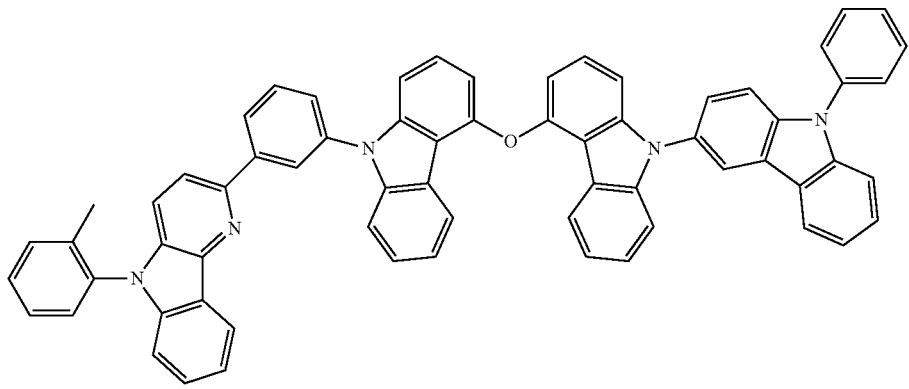
H-157
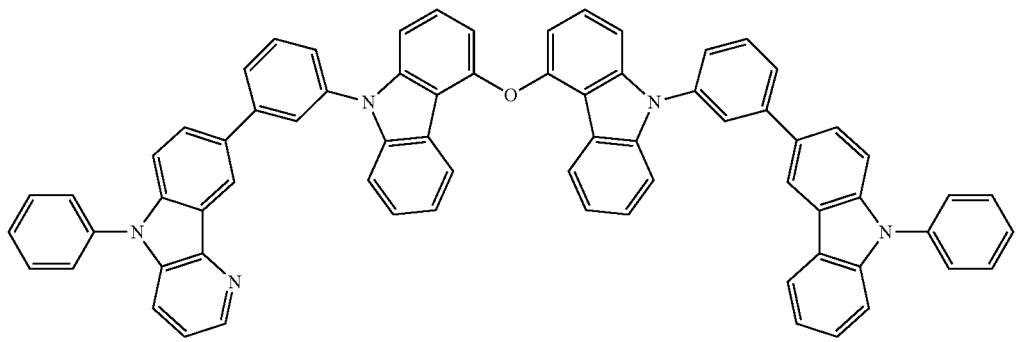
H-158
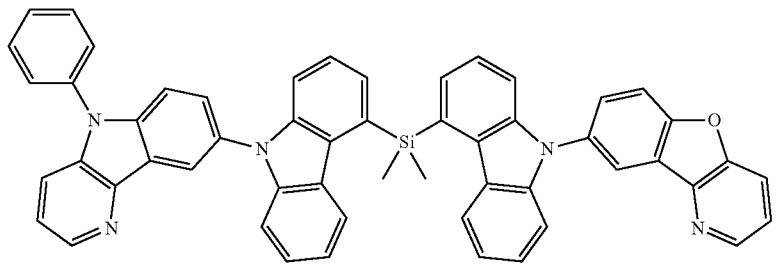
H-159
H-160
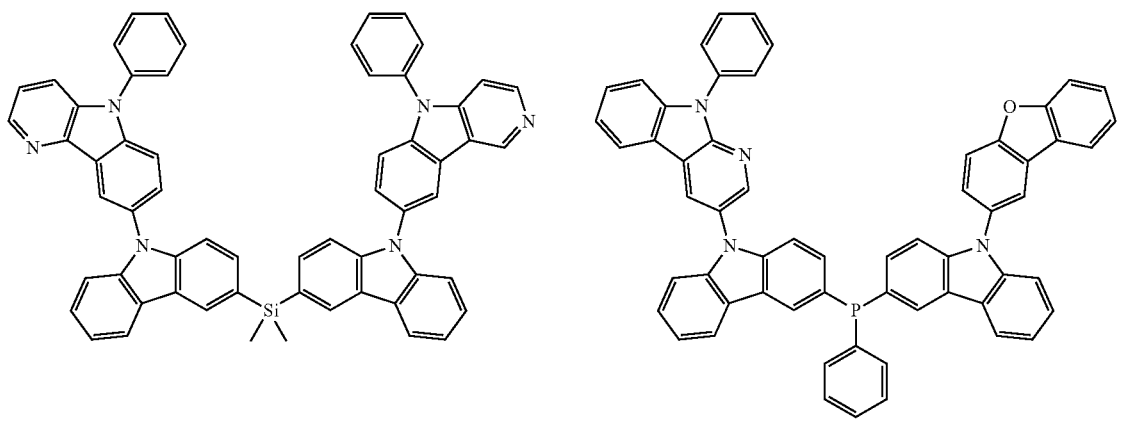

-continued
H-161
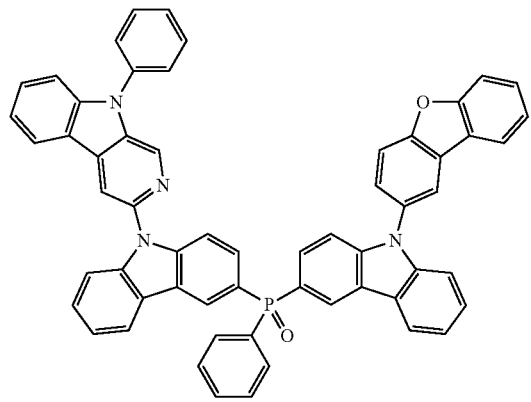
H-162
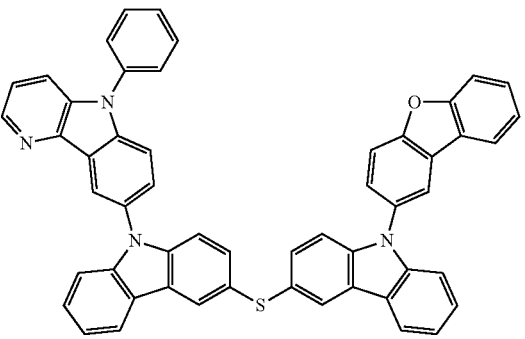
H-163
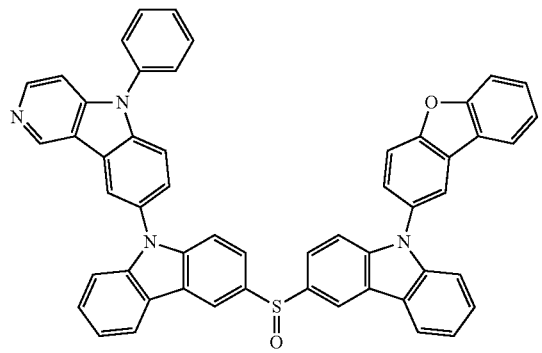
H-164
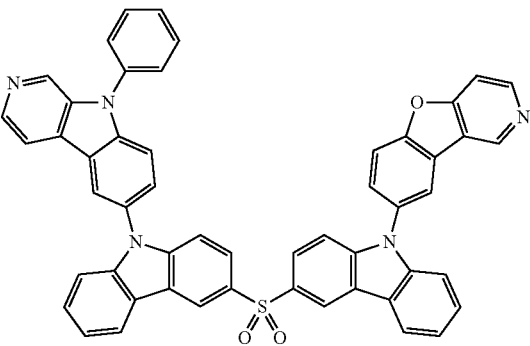
H-165
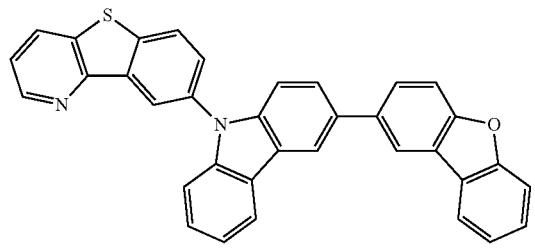
H-166
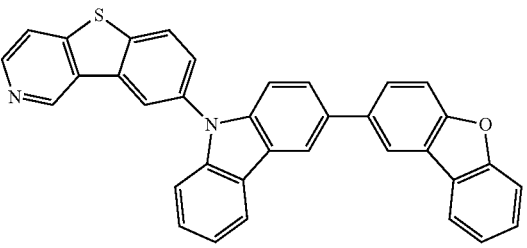
H-167
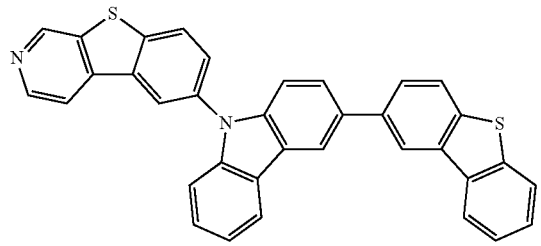
H-168
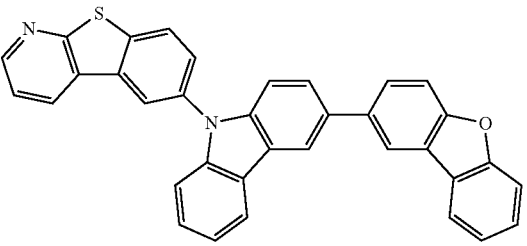
H-169
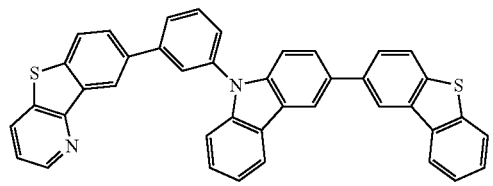
H-170
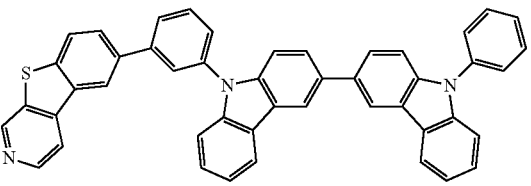

-continued
H-171
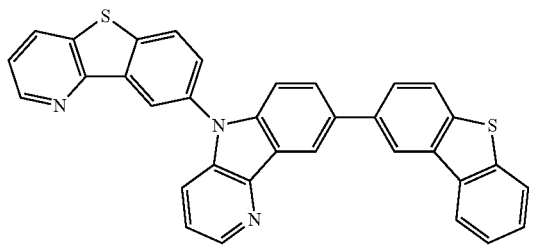
H-172
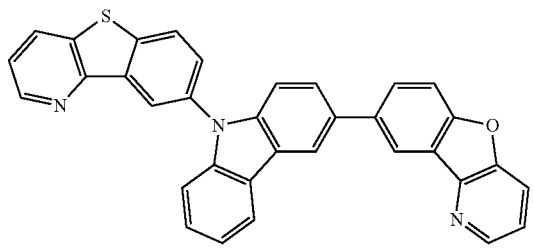
H-173
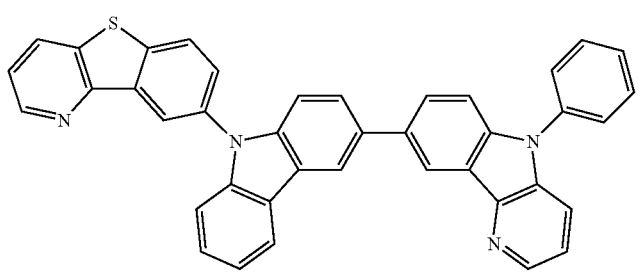
H-174
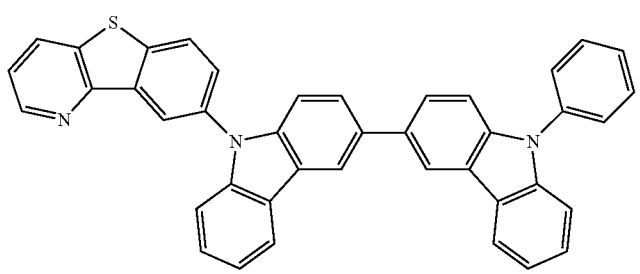
H-175
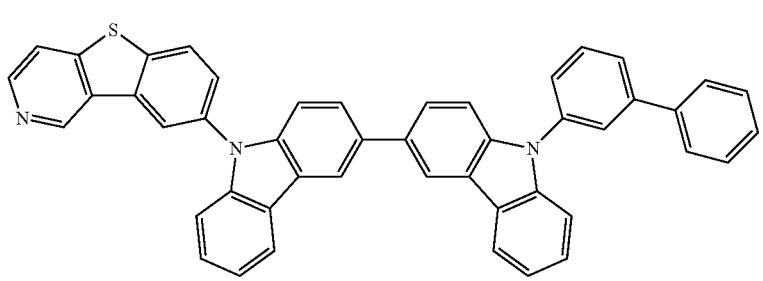
H-176
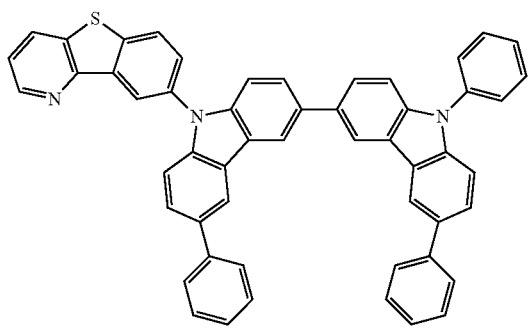
H-177
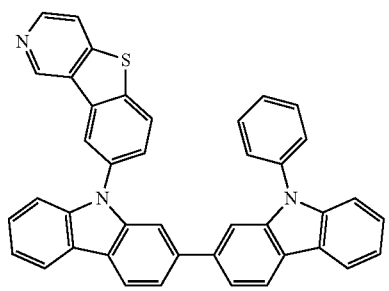

-continued
H-178
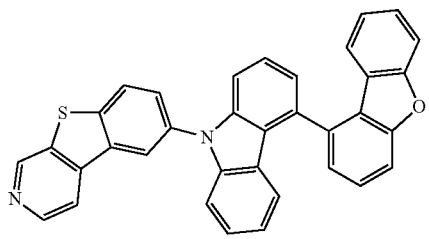
H-179
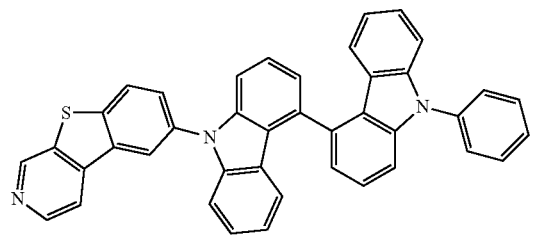
H-180
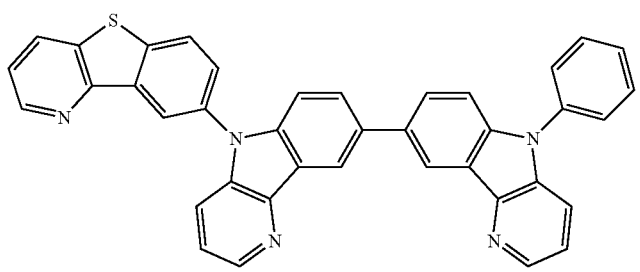
H-181
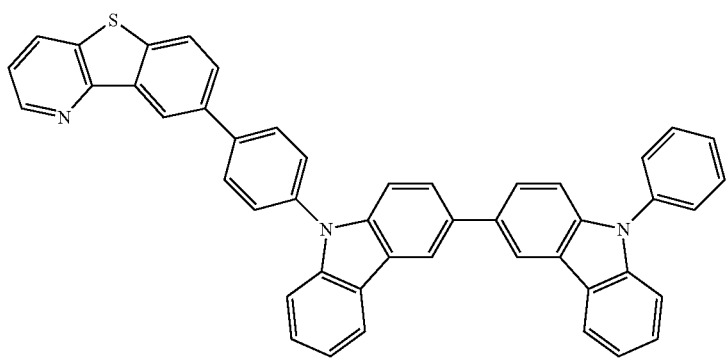
H-182
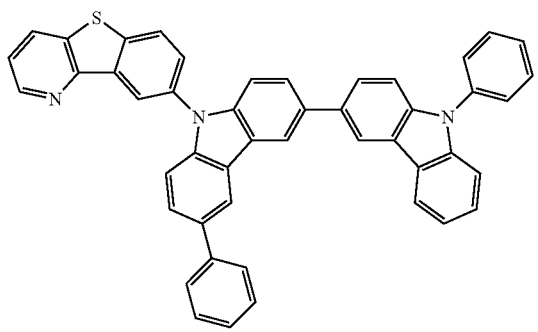
H-183
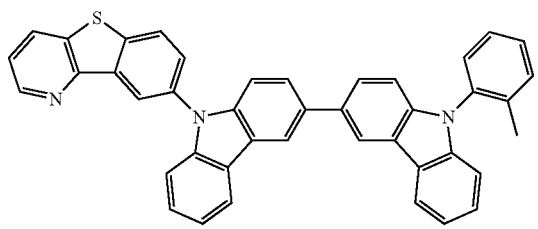
H-184
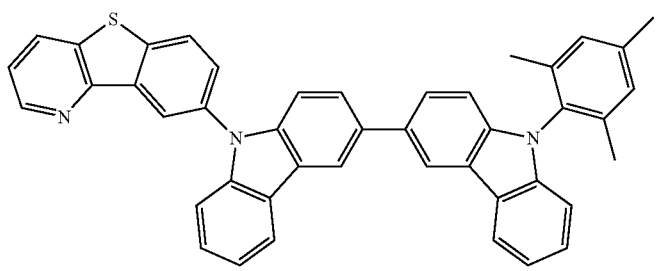

H-185
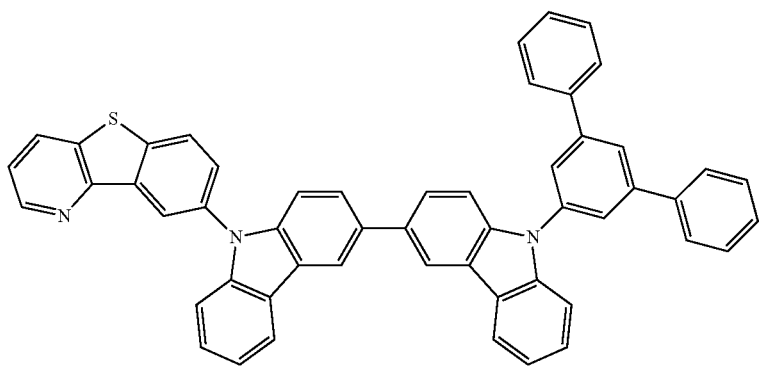
H-186
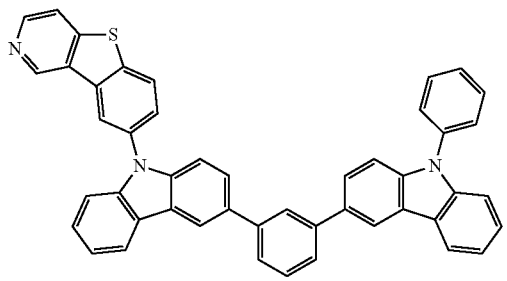
H-187
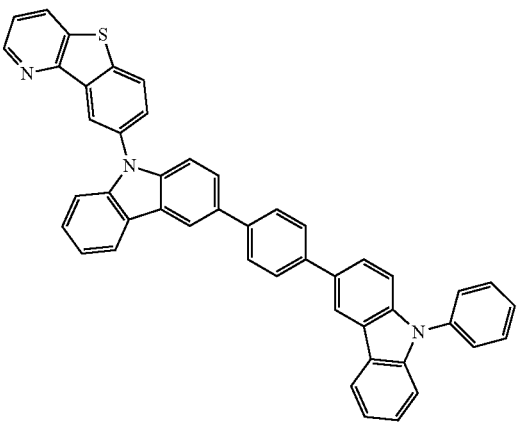
H-188
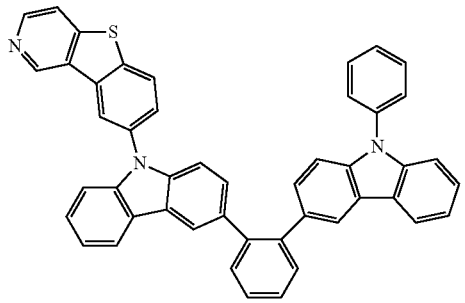
H-189
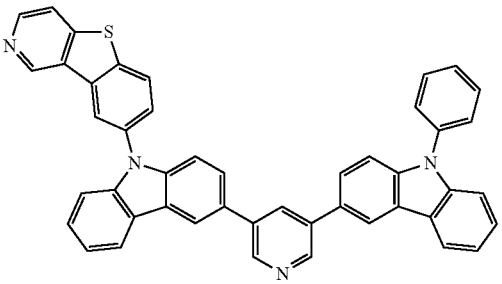
H-190
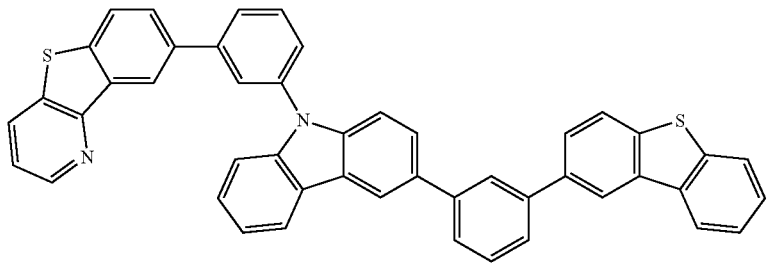

H-191
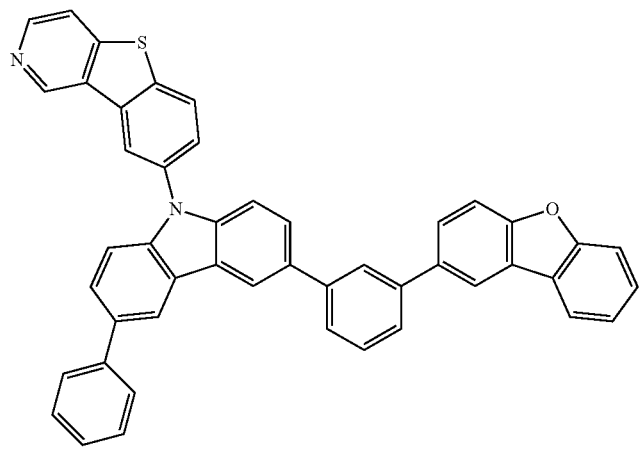
H-192
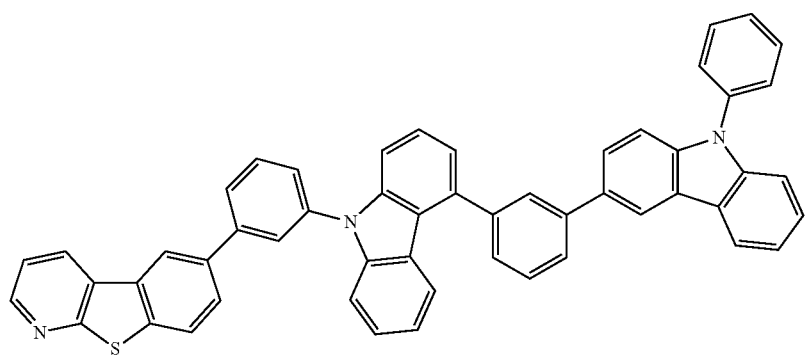
H-193
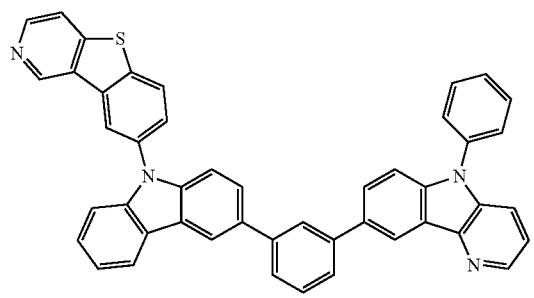
H-194
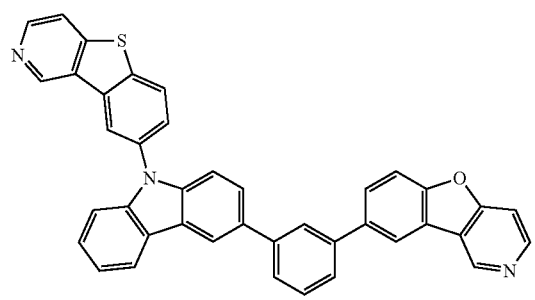
H-195
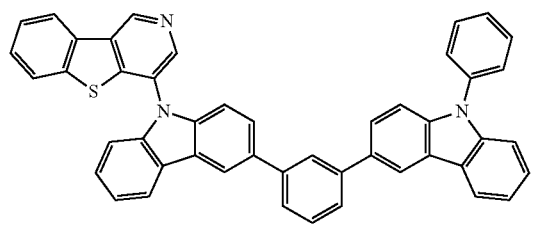
H-196
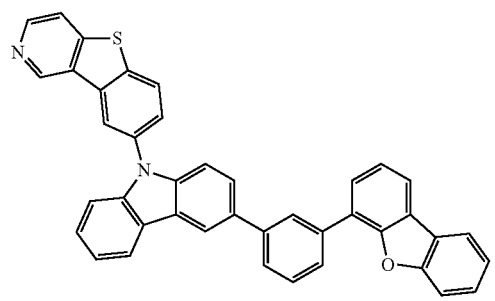

-continued
H-197
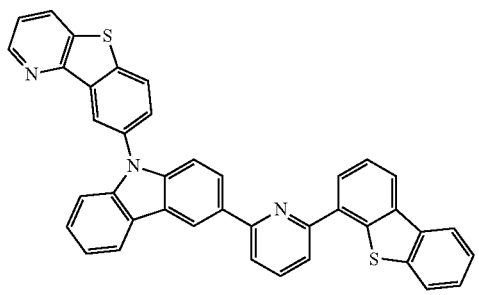
H-198
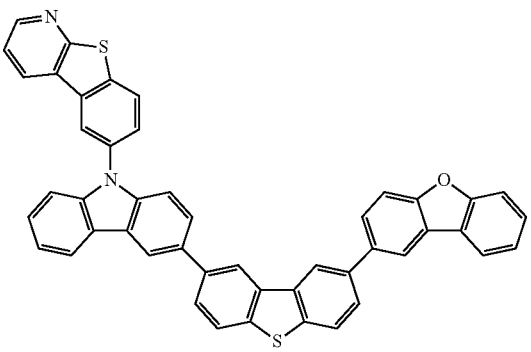
H-199
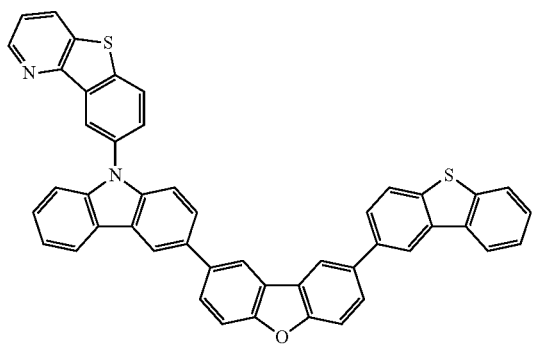
H-200
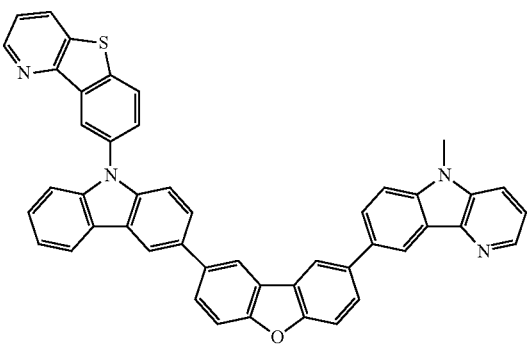
H-201
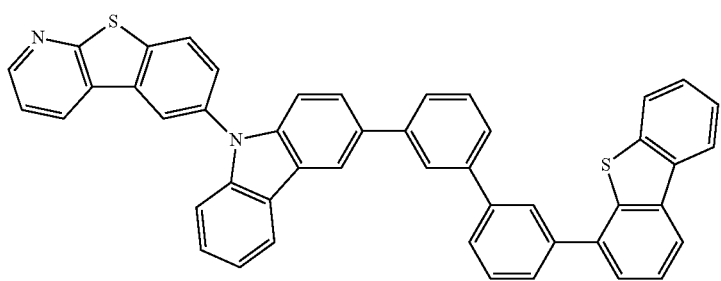
H-202
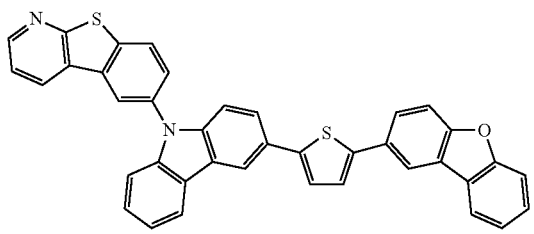
H-203
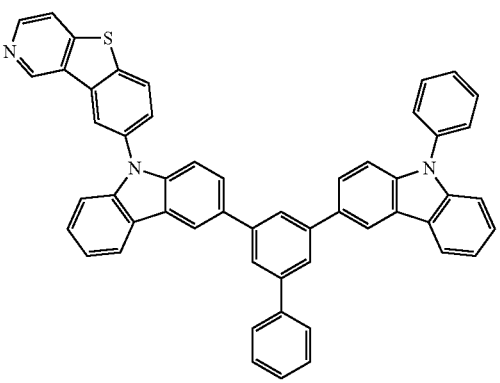

-continued
H-204
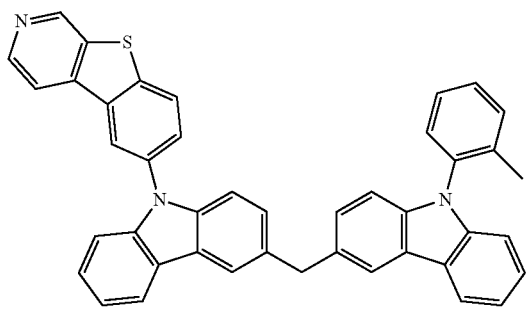
H-205
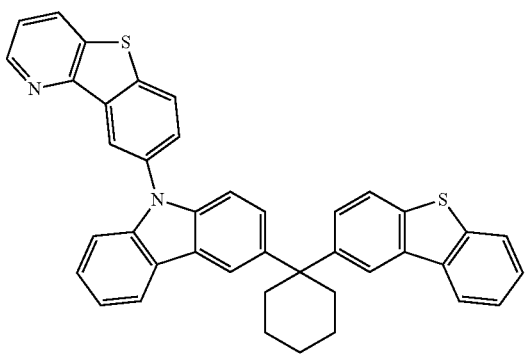
H-206
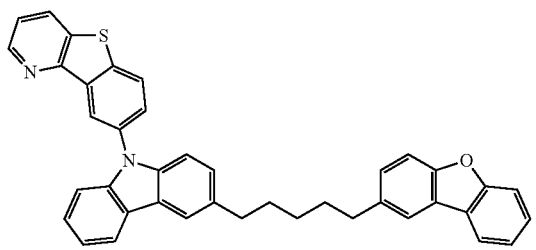
H-207
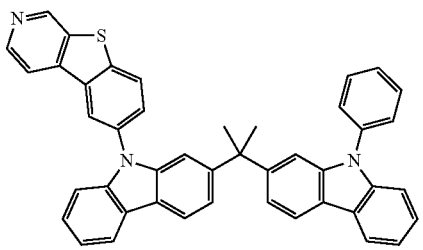
H-208
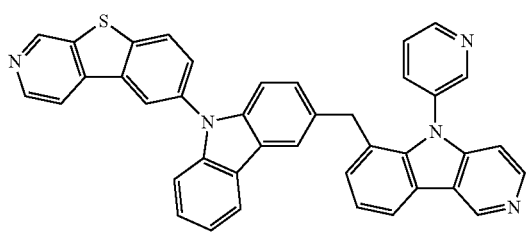
H-209
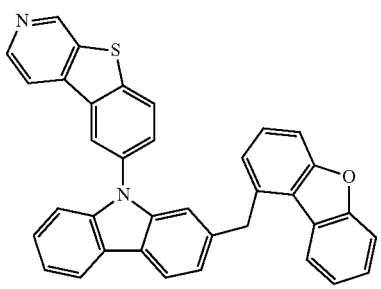
H-210
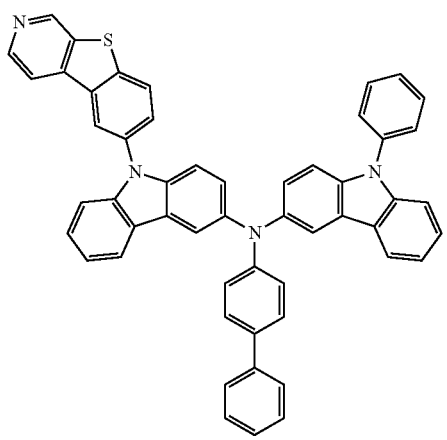
H-211
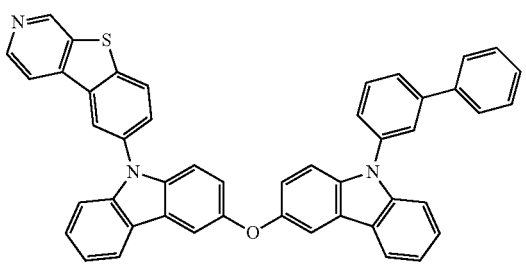

-continued
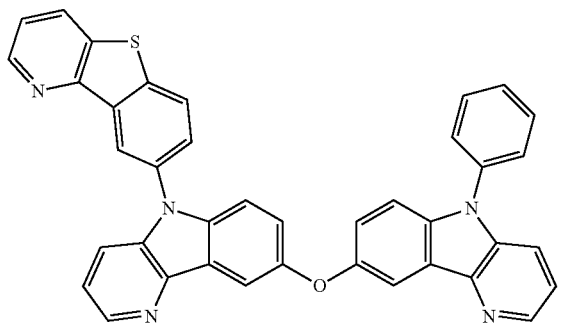
H-212
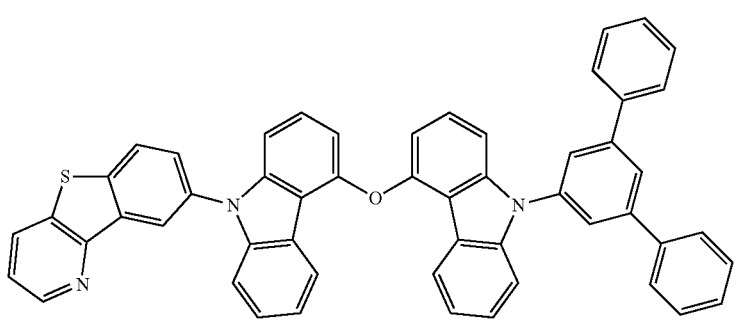
H-213
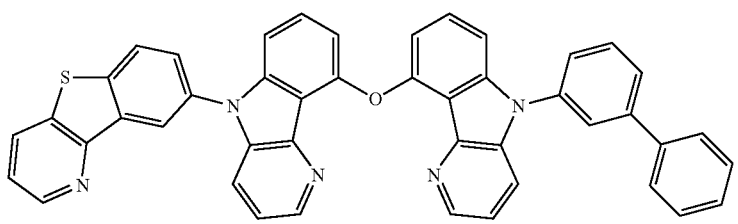
H-214
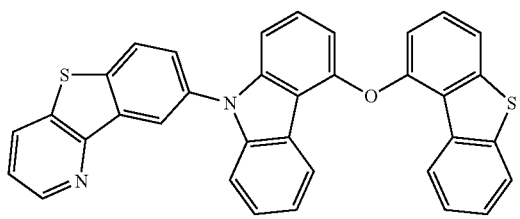
H-215
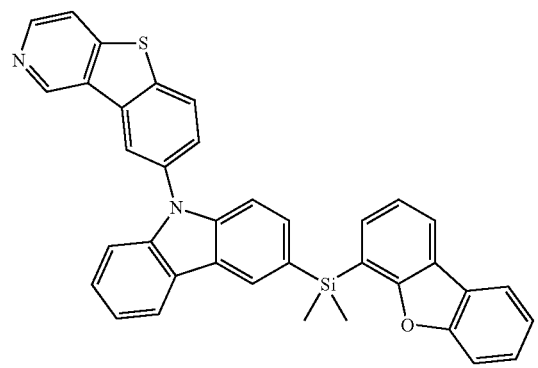
H-216

-continued
H-217
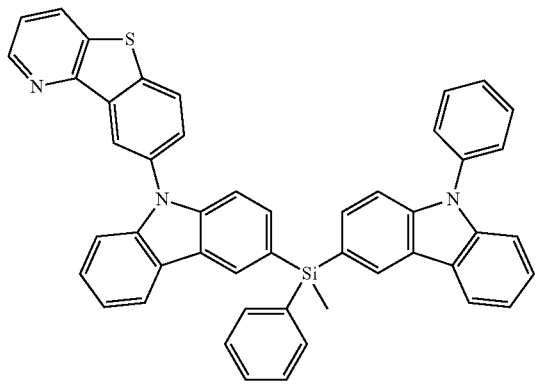
H-218
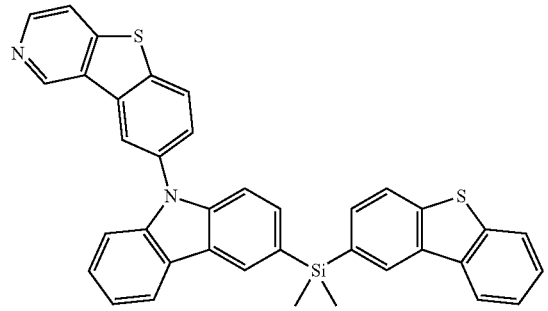
H-219
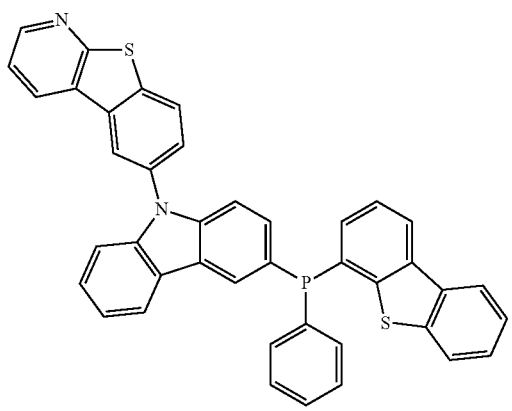
H-220
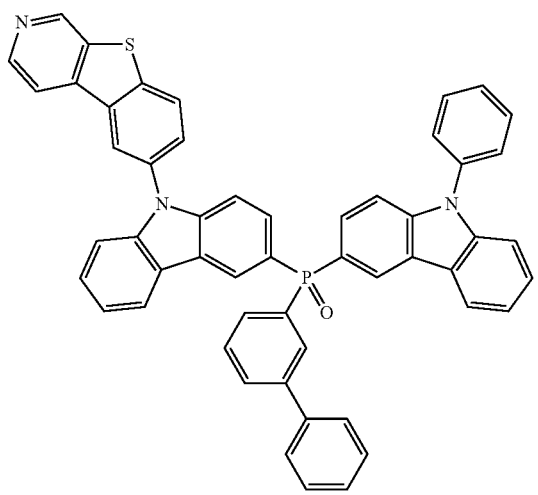
H-221
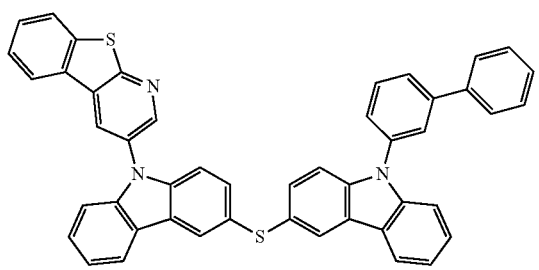
H-222
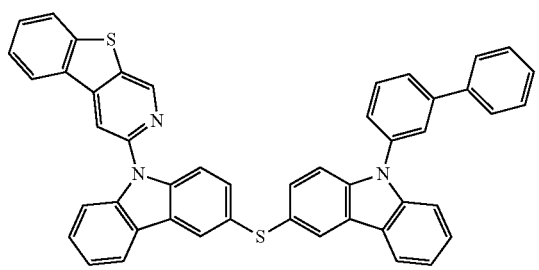
H-223
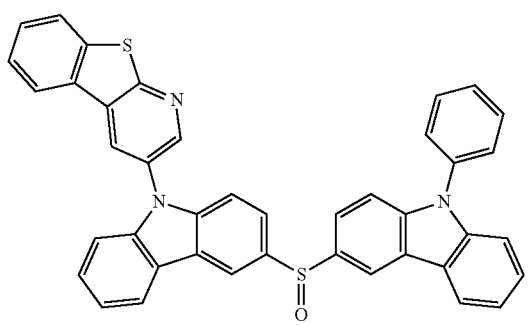
H-224
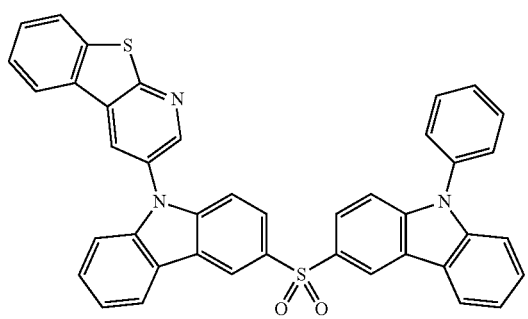

-continued
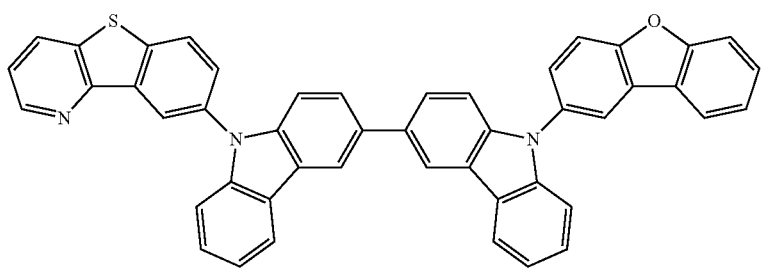
H-225
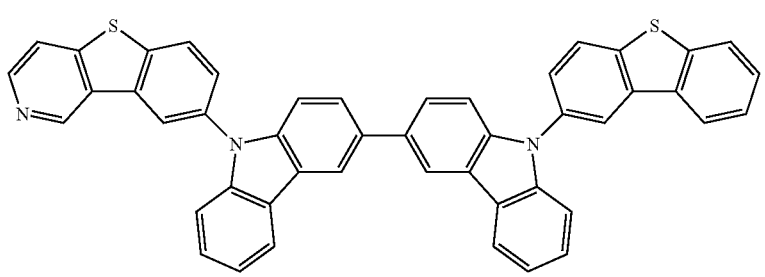
H-226
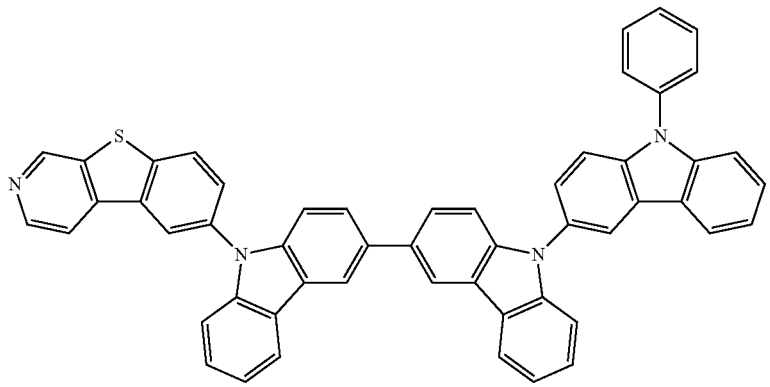
H-227
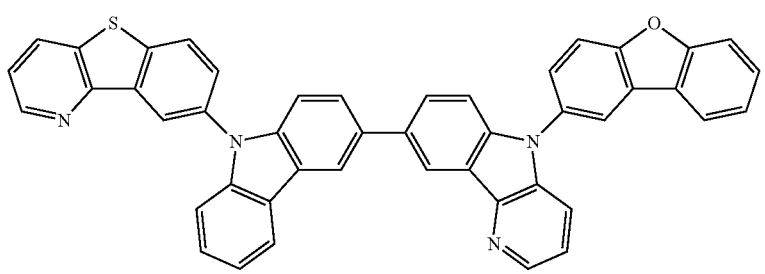
H-228
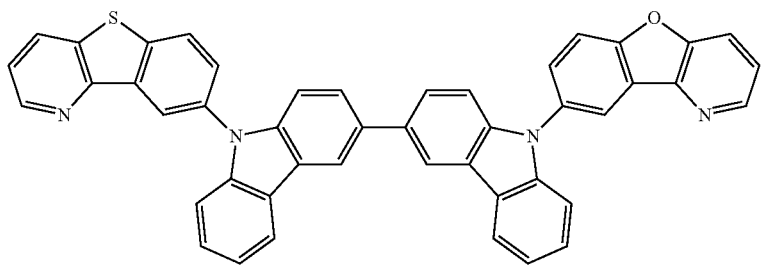
H-229

-continued
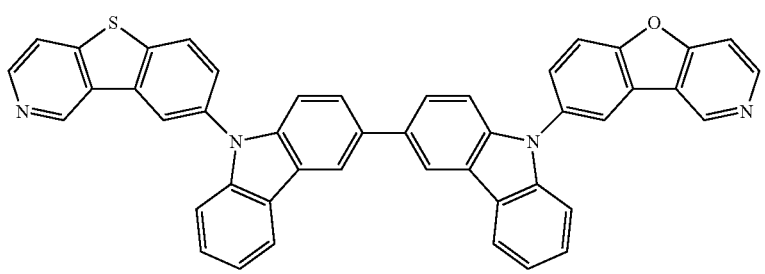
H-230
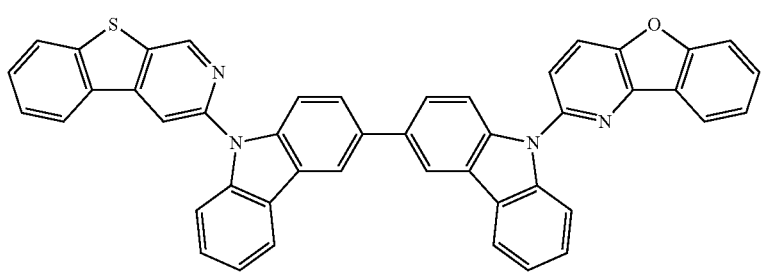
H-231
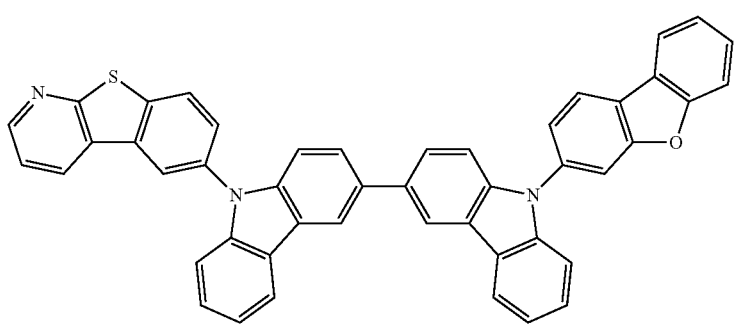
H-232
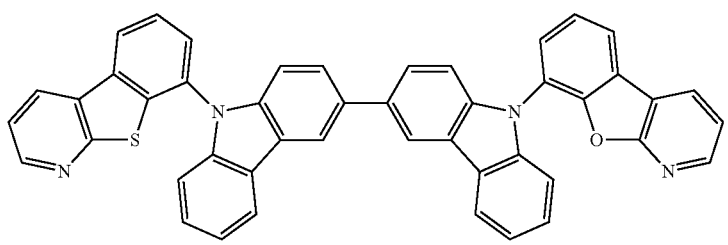
H-233
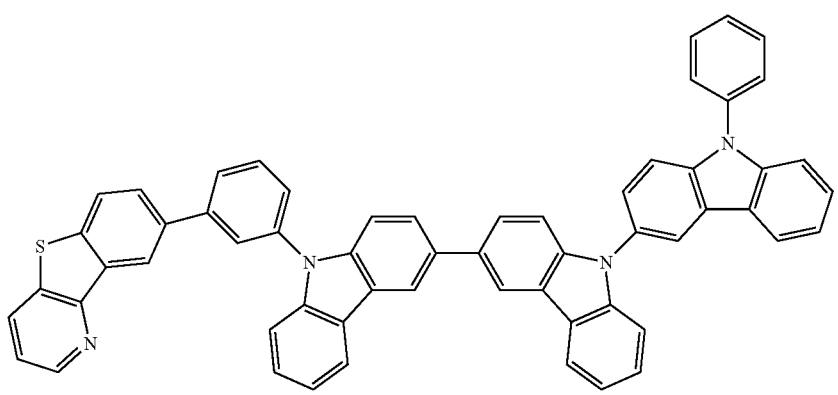
H-234

-continued
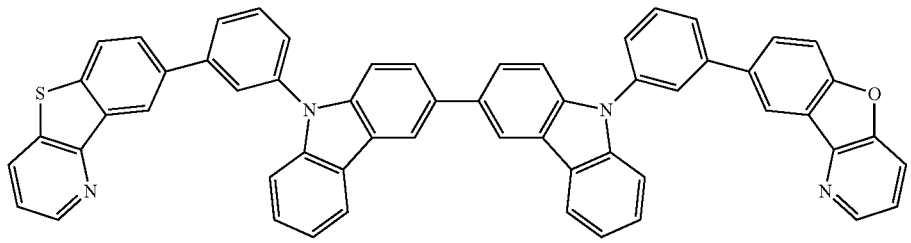
H-235
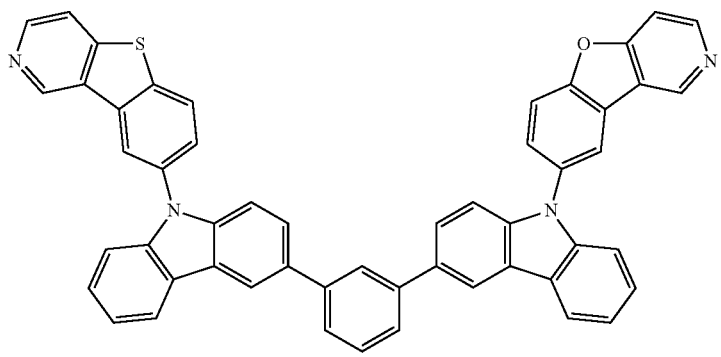
H-236
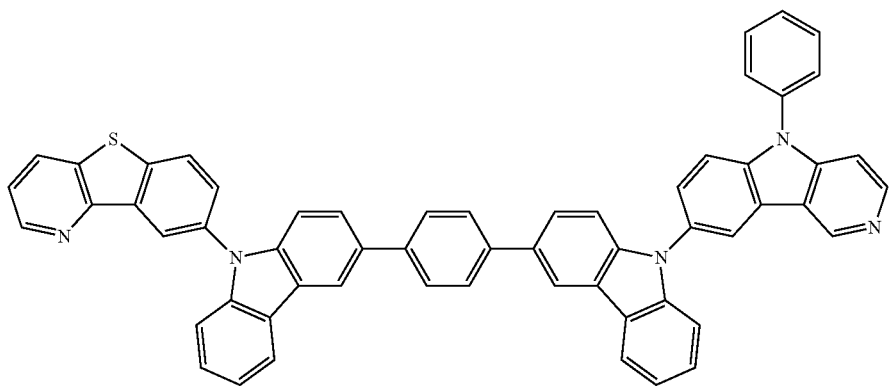
H-237
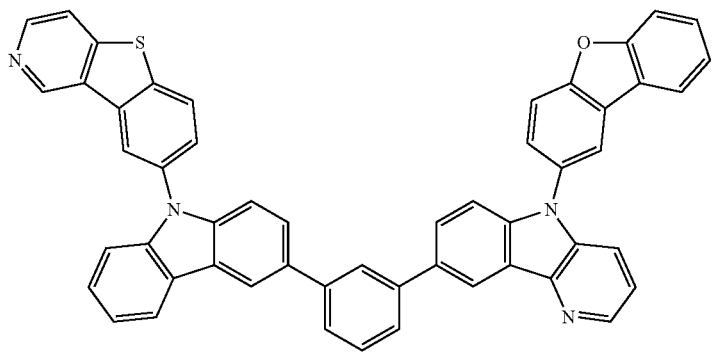
H-238

-continued
H-239
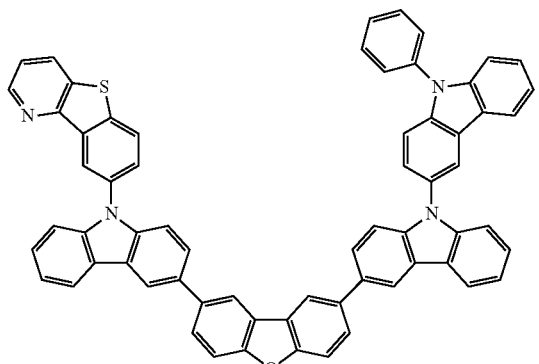
H-240
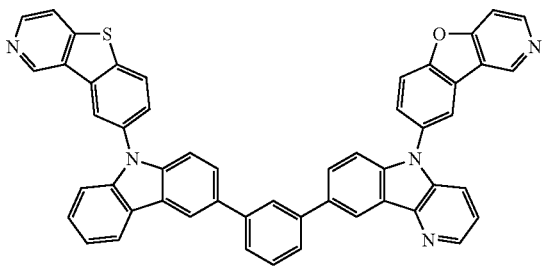
H-241
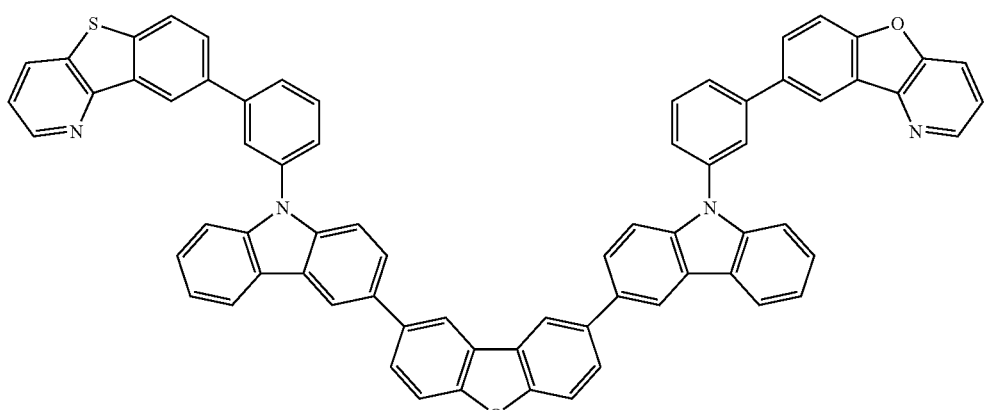
H-242
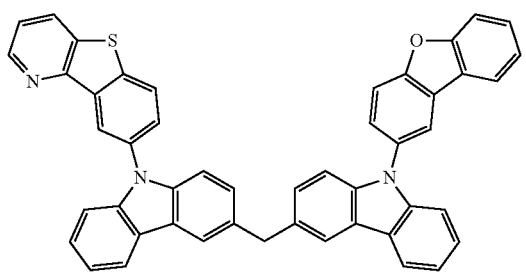
H-243
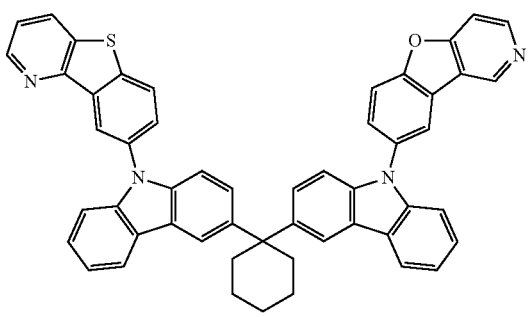
H-244
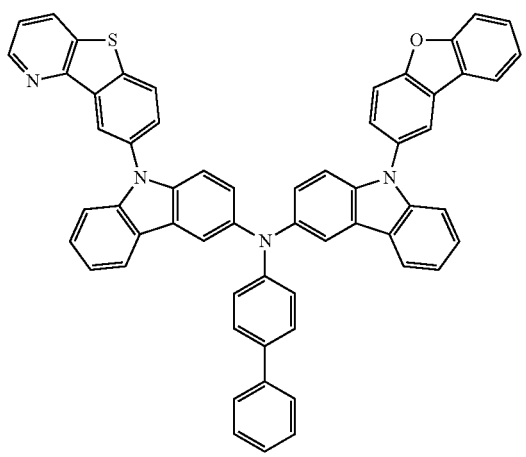
H-245
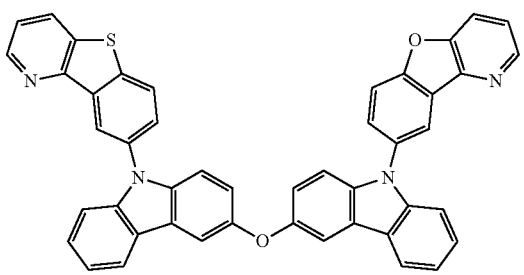

-continued
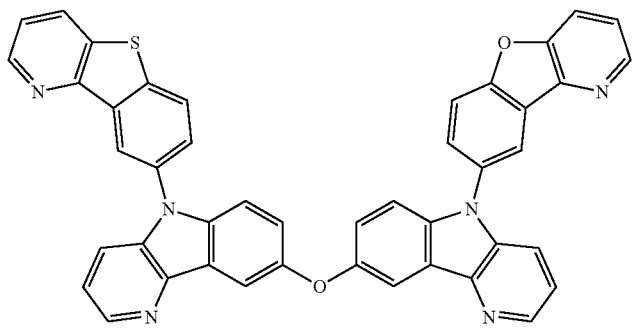
H-246
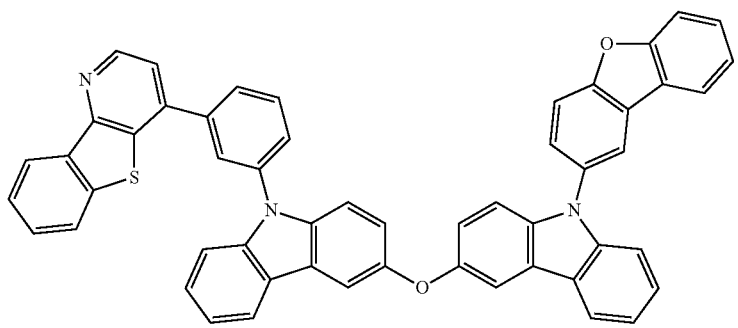
H-247
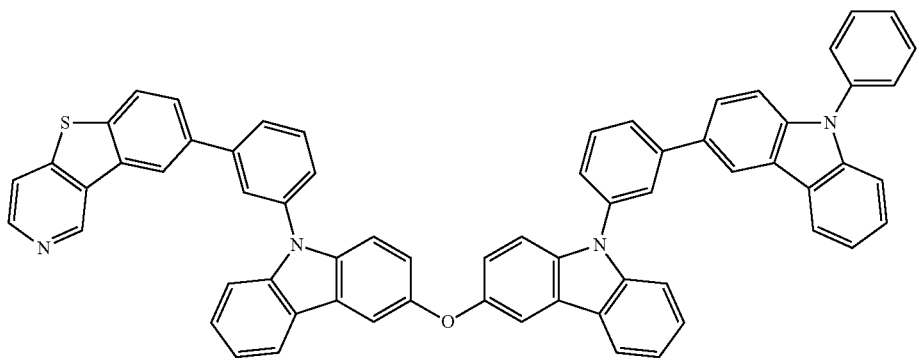
H-248
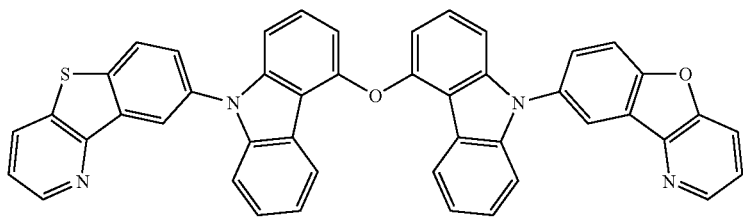
H-249
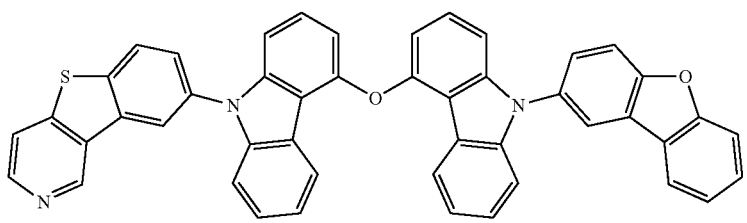
H-250

-continued
H-251
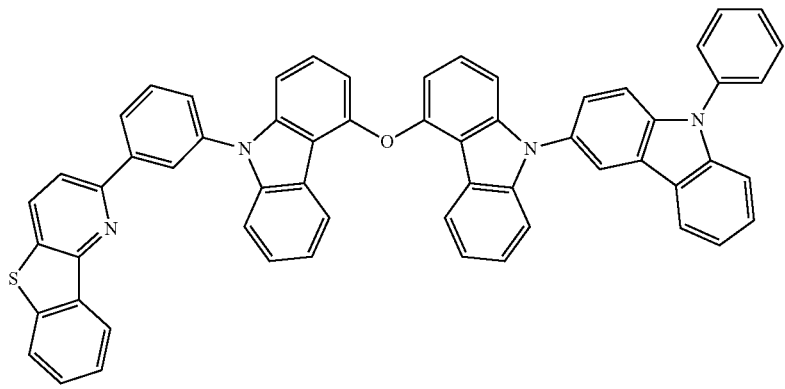
H-252
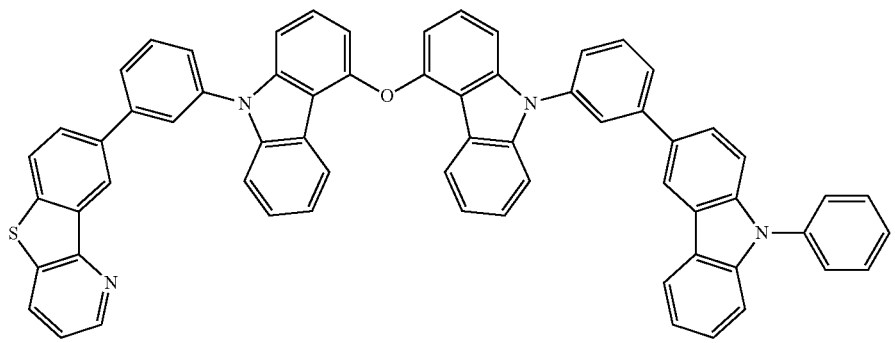
H-253
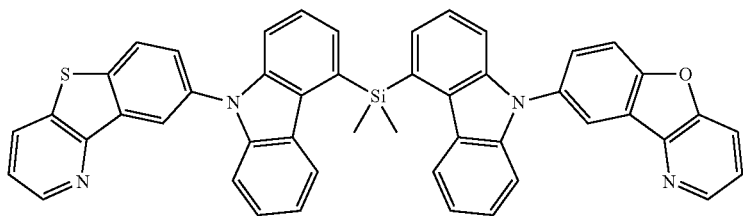
H-254
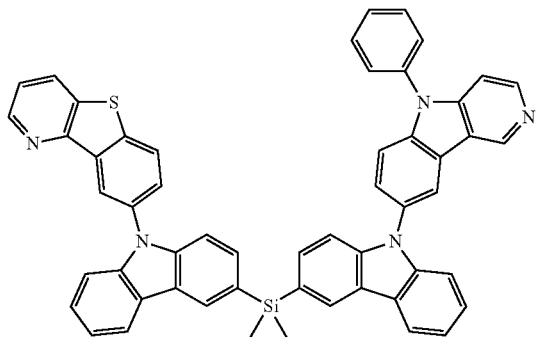
H-255
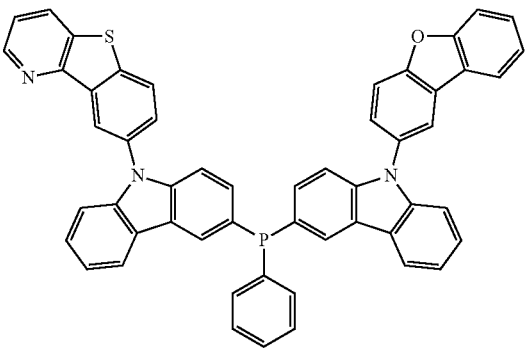

-continued
H-256
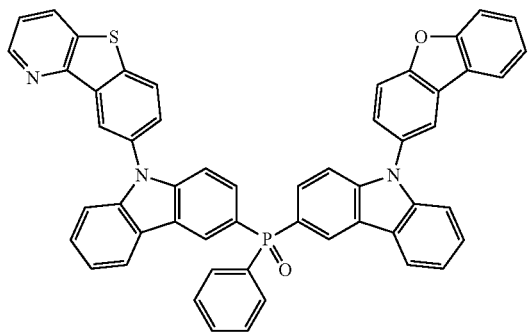
H-257
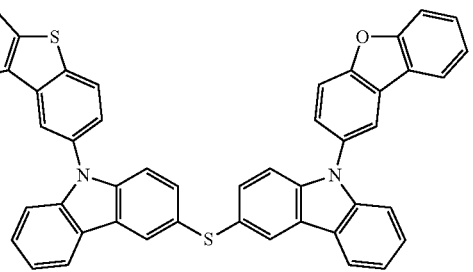
H-258
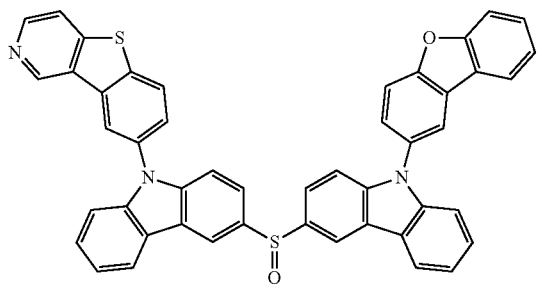
H-259
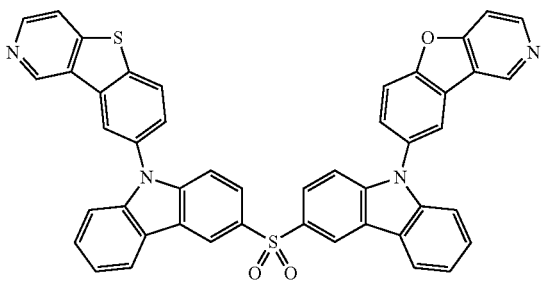
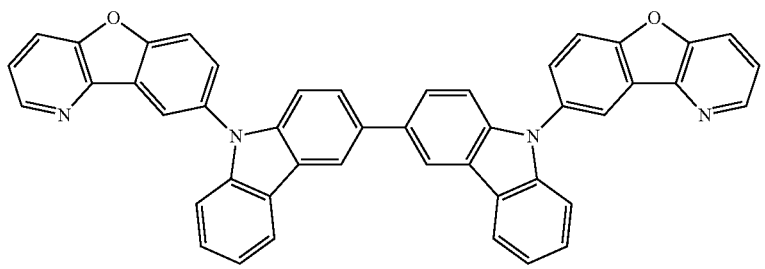
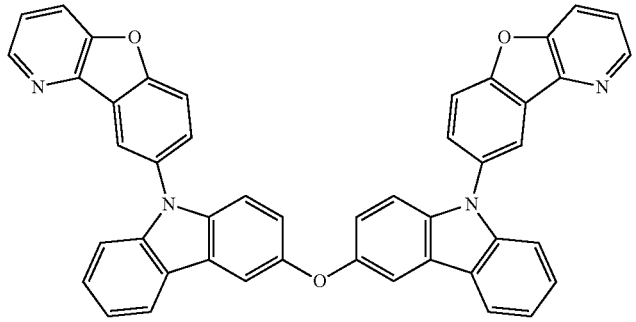
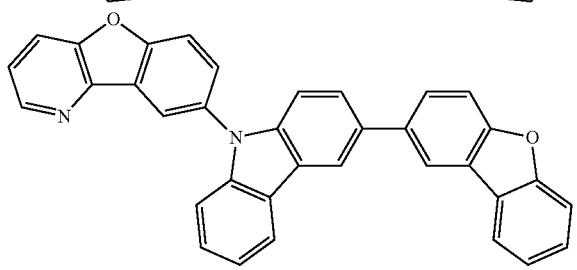

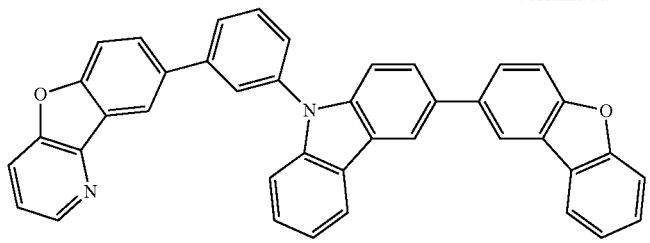
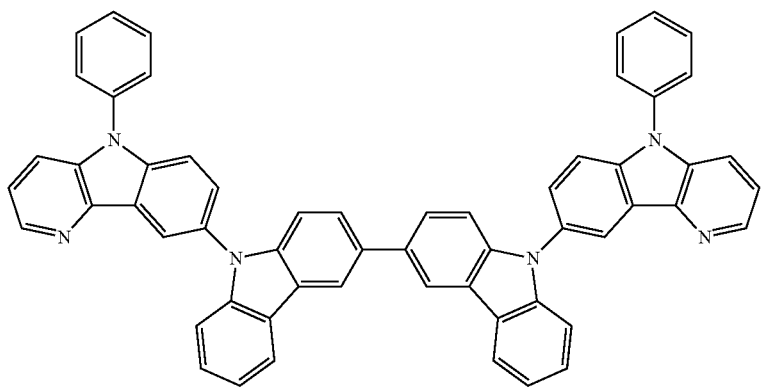
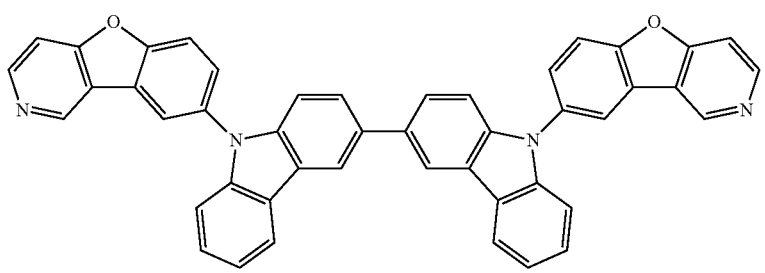
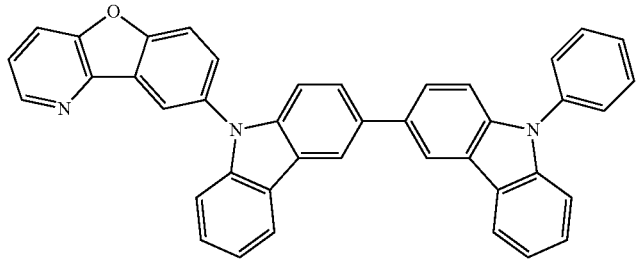
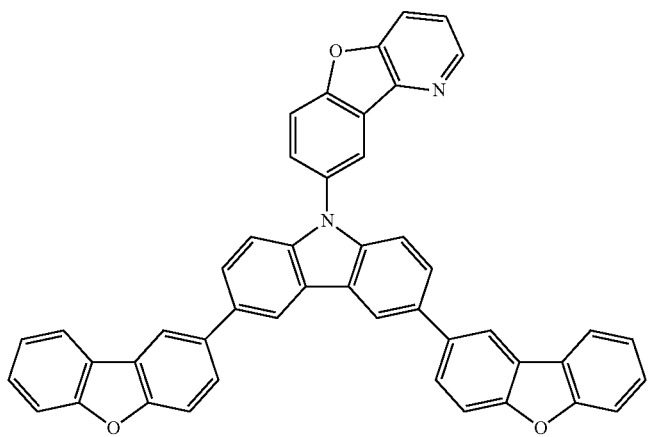

-continued
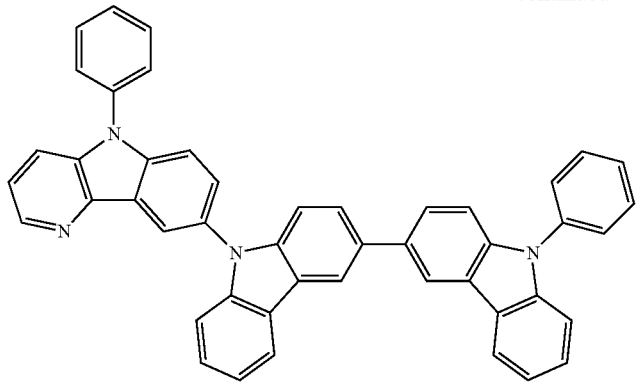
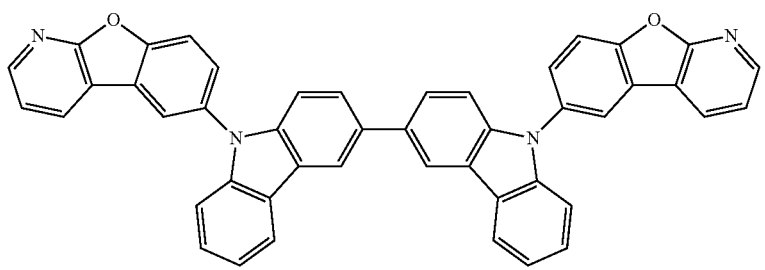
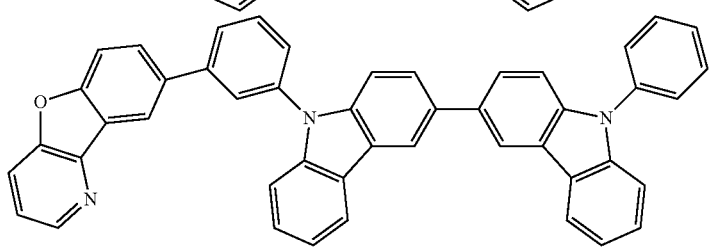
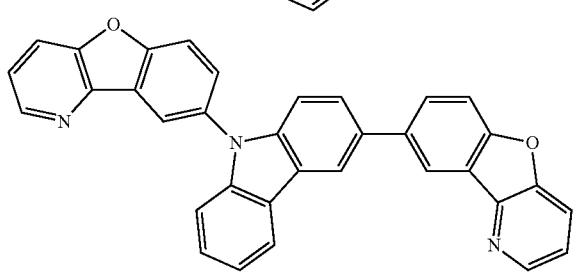
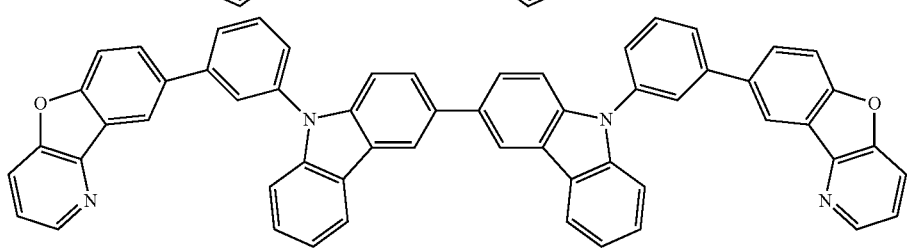
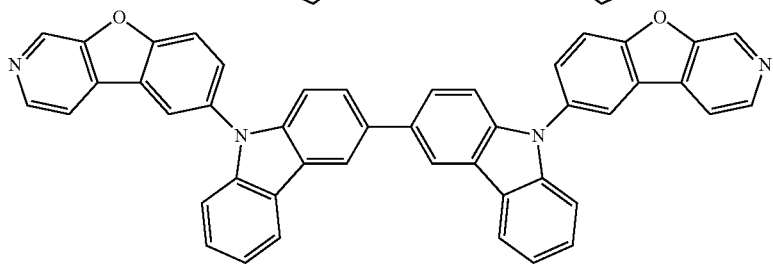

The organic EL device of the invention will be described below.

The organic EL device of the invention comprises an organic thin film layer comprising at least one layer between a cathode and anode. The organic thin film layer comprises a light emitting layer comprising a phosphorescent emitting material. At least one layer of the organic thin film layer comprises the material for organic electroluminescence device of the invention.

The multi-layered structure of the organic EL device include a multi-layered laminate, for example, anode/hole transporting zone (hole injecting layer and/or hole transporting layer)/light emitting layer/cathode; anode/light emitting layer/electron transporting zone (blocking layer, electron transporting layer and/or electron injecting layer)/cathode; and anode/hole transporting zone/light emitting layer/electron transporting zone/cathode.

The organic EL device may be a tandem device having at least two organic layer units which comprise a light emitting layer. Examples of the structure of the organic layer unit include hole transporting zone/light emitting layer, light emitting layer/electron transporting zone, and hole transporting zone/light emitting layer/electron transporting zone.

An intermediate layer (also referred to as intermediate conductive layer, charge generation layer, or CGL) may be interposed between two light emitting layers and an electron transporting zone may be disposed in each unit. At lease one of the light emitting layers of a tandem device is a phosphorescent emitting layer. Examples of the laminate structure of the tandem device include anode/phosphorescent emitting layer/intermediate layer/phosphorescent emitting layer/electron transporting zone (preferably including a blocking layer)/cathode, anode/phosphorescent emitting layer/electron transporting zone (preferably including a blocking layer)/intermediate layer/phosphorescent emitting layer/cathode, anode/fluorescent emitting layer/intermediate layer/phosphorescent emitting layer/electron transporting zone (preferably including a blocking layer)/cathode, anode/phosphorescent emitting layer/electron transporting zone (preferably including a blocking layer)/intermediate layer/fluorescent emitting layer/cathode, and anode/phosphorescent emitting layer/electron transporting zone (preferably including a blocking layer)/intermediate layer/phosphorescent emitting layer/electron transporting zone (preferably including a blocking layer)/cathode.

The "hole injecting/transporting layer" referred to herein is an embodiment of the hole transporting layer. The light emitting layer may be a laminate of light emitting layers.

In an embodiment of the organic EL device of the invention, a hole transporting zone may be disposed between an anode and a light emitting layer and the light emitting layer or the hole transporting zone may contain the material for organic electroluminescence device of the invention, or an electron transporting zone may be disposed between a light emitting layer and a cathode and the electron transporting zone may contain the material for organic electroluminescence device of the invention.

The organic EL device of the invention contains the material for organic EL device represented by formula (1) preferably in at least one of the light emitting layer, the hole transporting zone (hole transporting layer, hole injecting layer), and the electron transporting zone (electron transporting layer, electron injecting layer, blocking layer), particularly preferably in the light emitting layer or the electron transporting zone.

The content of the material for organic electroluminescence device of the invention in each organic thin film layer containing it is preferably 50 volume % (v/v) or more, more preferably 70 volume % (v/v) or more, and still more preferably 90 volume % (v/v) or more.

The electron transporting zone preferably includes a blocking layer in the portion adjacent to the light emitting layer. As describes below, the blocking layer prevents the diffusion of the triplet excitons generated in the light emitting layer to the electron transporting zone to confine the triplet excitons in the light emitting layer, thereby preventing the energy of the triplet excitons from being deactivated on the molecules other than the emitting dopant, i.e., on the molecules in the electron transporting zone.

This effect can be simply explained as follows to facilitate the understanding of the invention. By using the compound of the invention in the blocking layer of the electron transporting zone, the energy deactivation of triplet excitons in the electron transporting zone may be prevented while efficiently injecting electrons into the light emitting layer. Namely, by using the compound of the invention in the blocking layer, the electron-hole recombination zone may be easily controlled. In addition, since the compound of the invention has a high electrochemical stability to both hole injection and hole transport, the blocking layer containing the compound of the invention may be prevented from the electrochemical deterioration, thereby providing an organic electroluminescence device excellent in the durability.

If a device having a blocking layer satisfies the following energy relationship:

$$E^T_d < E^T_{TB}$$

wherein $E^T_d$ is the triplet energy of the phosphorescent dopant in the light emitting layer and $E^T_{TB}$ is the triplet energy of the compound which forms the blocking layer, the triplet excitons of phosphorescent dopant are confined due to the energy relationship (not diffuse to other molecules). Therefore, the energy deactivation process other than the emission on the phosphorescent dopant may be prevented to cause the emission with high efficiency. However, even in case of satisfying the relationship of $E^T_d < E^T_{TB}$, the triplet excitons may move into other molecules if the energy difference ($\Delta E^T = E^T_{TB} - E^T_d$) is small, because the energy difference $\Delta E^T$ may be overcome by the absorption of ambient heat energy when driving a device at around room temperature as generally employed in the practical use of device. As compared with the fluorescent emission, the phosphorescent emission is relatively likely to be affected by the diffusion of excitons due to the heat absorption, because the lifetime of triplet excitons is longer. Therefore, the use of the compound of the invention in the blocking layer may be effective for increasing the efficiency of a phosphorescent device. As for the energy difference $\Delta E^T$, the larger as compared with the heat energy of room temperature, the better. Therefore, the energy difference $\Delta E^T$ is more preferably 0.1 eV or more and particularly preferably 0.2 eV or more.

The triplet energy referred to herein was determined as follows. A sample was dissolved in EPA solvent (diethyl ether:isopentane:ethanol=5:5:2 (by volume)) in a concentration of 10 μmol/L to prepare a specimen for phosphorescence measurement. The specimen for phosphorescence measurement was placed in a quartz cell and irradiated with excitation ray at 77 K, and the emitted phosphorescence was measured. Using the measured result, the triplet energy was determined as the value calculated from the following conversion formula:

$$E^T(eV)=1239.85/\lambda_{edge}.$$

On the phosphorescence spectrum with a vertical axis of phosphorescent intensity and a horizontal axis of wavelength, a line tangent to the rising portion at the short-wavelength side of the phosphorescent spectrum was drawn, and the wavelength (nm) at the intersection of the tangent line and the horizontal axis was expressed by "$\lambda_{edge}$."

A material satisfying the following relationship:

$$A_b - A_h \leq 0.1 eV$$

wherein $A_b$ is the affinity level of the blocking layer material and $A_h$ is the affinity level of the host material in the light emitting layer,
is preferably used as the host material in the light emitting layer.

The electron affinity is defined as the amount of energy released or absorbed when one electron is added to a molecule. The affinity level is expressed by a positive sign when the energy is released and a negative sign when the energy is absorbed.

Using the ionization potential Ip and the optical energy gap Eg(S), the affinity level Af is expressed by:

$$Af=Ip-Eg(S).$$

The ionization potential Ip is the amount of energy required to remove an electron from a compound to form an ion. In the present invention, Ip is a positive value measured by a photoelectronic spectrophotometer (AC-3, manufactured by Riken Keiki Co., Ltd.) in the atmosphere. The optical energy gap Eg(S) is the difference between the conduction level and the valence level. In the present invention, Eg(S) is a positive value which is determined by measuring an ultraviolet/visible absorption spectrum of a diluted dichloromethane solution of a material, drawing a line tangent to the spectrum at the long-wavelength side, and converting the wavelength of the intersection between the tangent line and the base line (zero absorption) to the unit of energy.

The electron mobility of the blocking layer material is preferably $10^{-6}$ cm$^2$/Vs or more when measured at an electric field strength of 0.04 to 0.5 MV/cm. There are several methods for measuring the electron mobility of organic materials, for example, Time of Flight method. In the present invention, the electron mobility is determined by an impedance spectroscopy.

The electron mobility of the electron injecting layer is preferably $10^{-6}$ cm$^2$/Vs or more when measured at an electric field strength of 0.04 to 0.5 MV/cm. Within the above range, the electron injection from the cathode to the electron injecting layer is promoted, and thus, the electron injection into the adjacent blocking layer and light emitting layer is also promoted, thereby allowing the driving at lower voltage.

In view of good heat stability, the glass transition point of the material for organic electroluminescence device of the invention is preferably 140° C. or higher and more preferably 150° C. or higher. The upper limit of the glass transition point is generally about 260° C. The glass transition point was determined by heating and cooling about 3 mg of sample according to the following 2-cycle heating/cooling process (1) to (6) using DSC 8500 manufactured by Perkin Elmer Inc. and reading the temperature of the inflection point where the base line of DSC curve in the temperature-rising step (6) changed stepwise, thereby determining the glass transition point:

(1) keeping the sample at 30° C. for one minute;

(2) heating the sample from 30° C. to a given temperature lower than the thermal decomposition temperature of the sample at a temperature rising speed of 10° C./min;

(3) keeping the sample at the given temperature for 3 min;

(4) cooling the sample from the given temperature to 0° C. at a cooling speed of 200° C./min;

(5) keeping the sample at 0° C. for 10 min; and (6) heating the sample from 0° C. to 200° C. at a temperature rising speed of 10° C./min.

The light emitting layer preferably comprises the host material and the dopant (phosphorescent emitting material) and the material for organic electroluminescence device of the invention is preferably used in the light emitting layer as the host material.

In view of obtaining a high phosphorescent quantum yield and further improving the external quantum efficiency of electroluminescence device, the phosphorescent emitting material is preferably a compound comprising a metal selected from iridium (Ir), osmium (Os) and platinum (Pt), more preferably a metal complex, such as an iridium complex, an osmium complex, and a platinum complex, and still more preferably an iridium complex and a platinum complex. The metal complex is preferably an ortho metallated complex wherein the central metal and the carbon atom of the ligand are ortho metal bonded to each other and more preferably an ortho metallated iridium complex. The iridium complexes are shown below as more preferred embodiment of the ortho metallated complex.

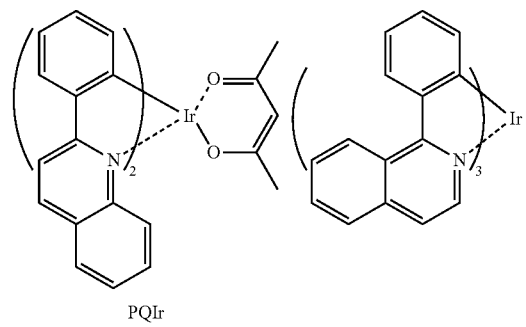

PQIr

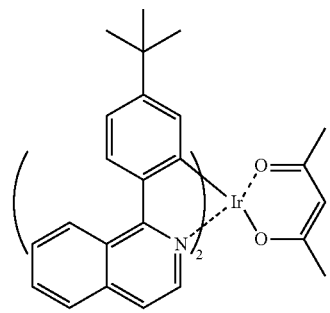

105
-continued
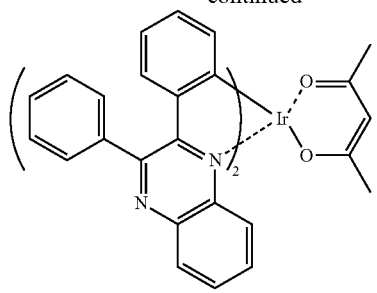
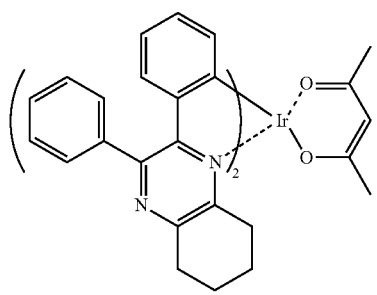
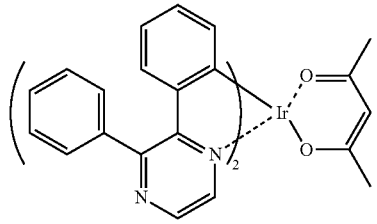
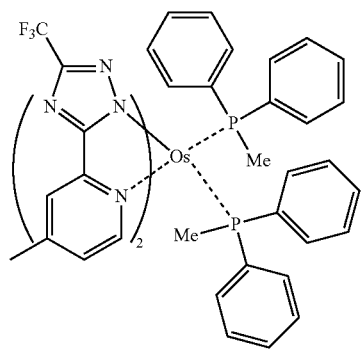
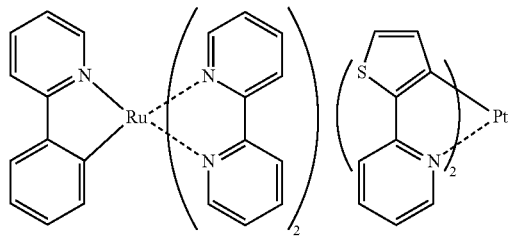
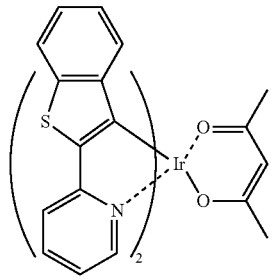
106
-continued
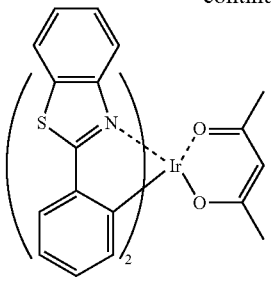
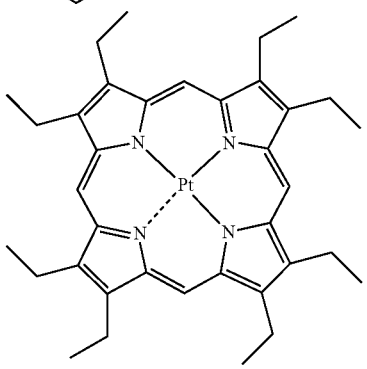
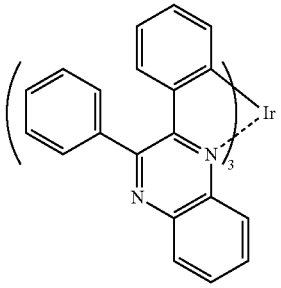
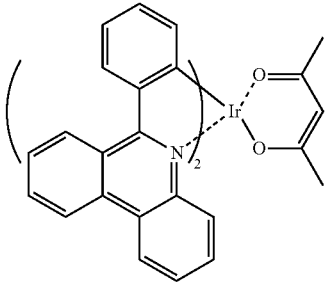
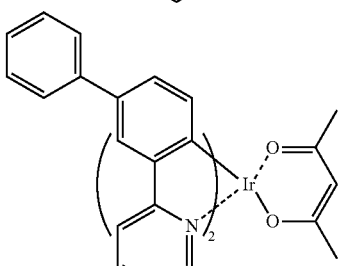
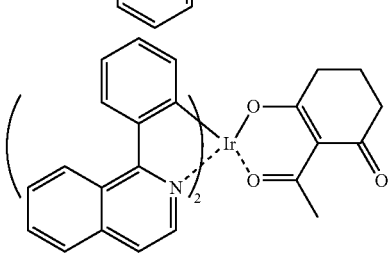

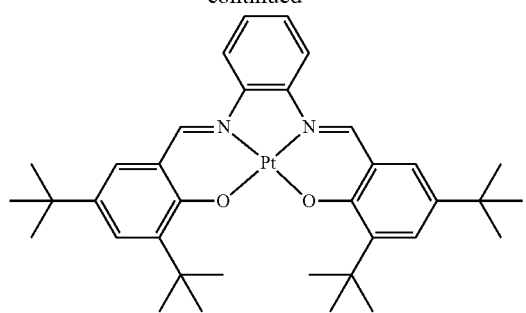
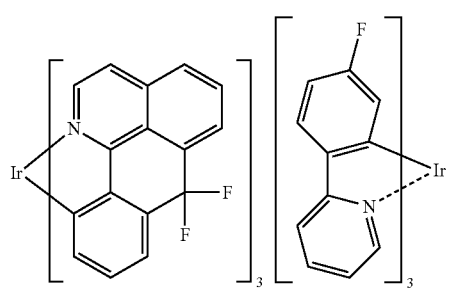
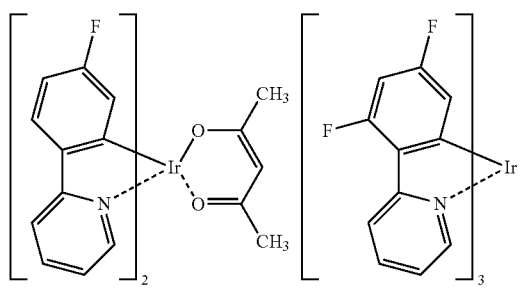
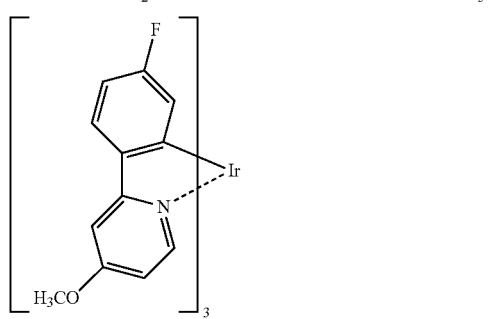
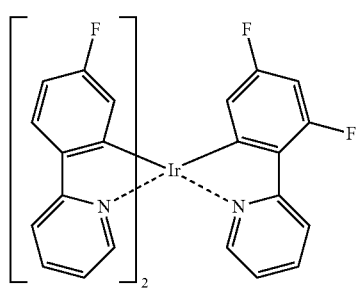
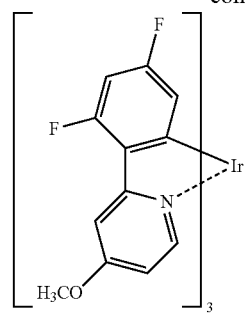
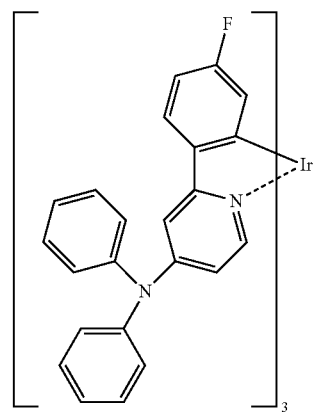
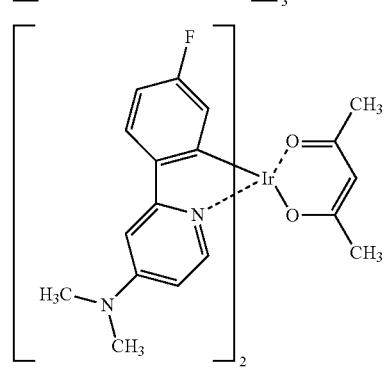
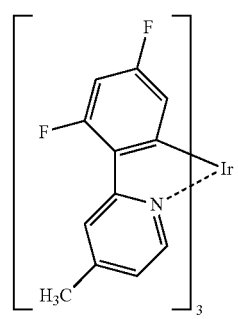
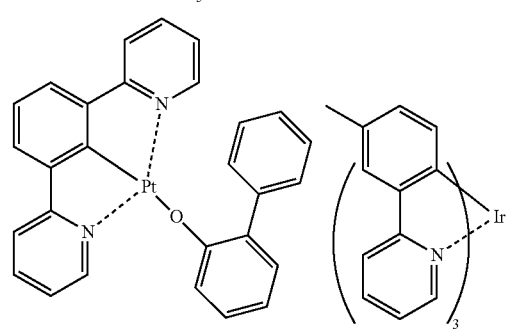

109
-continued
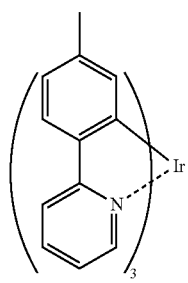
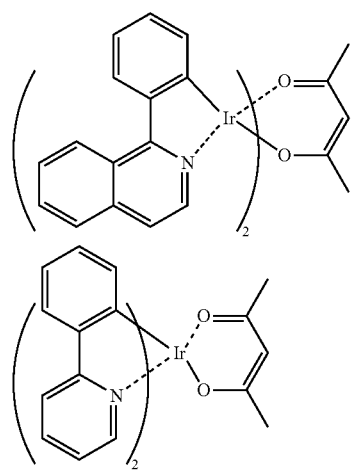
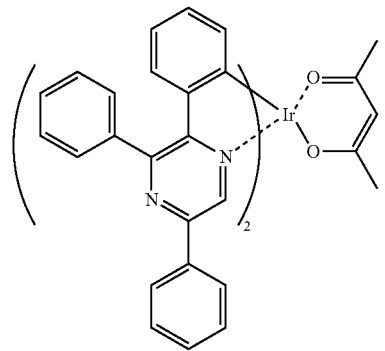
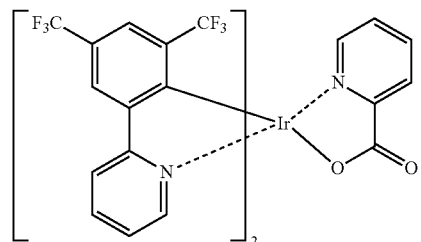
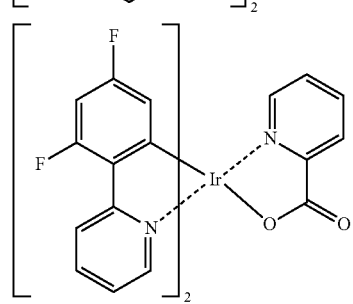
110
-continued
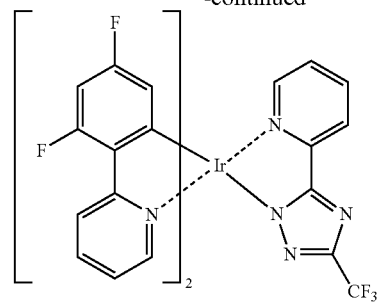
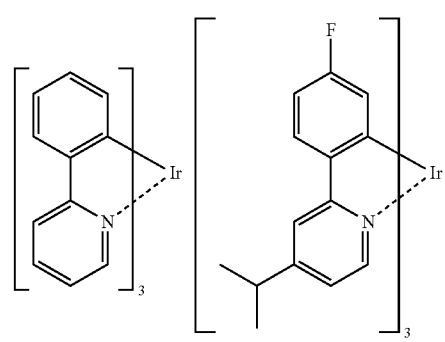
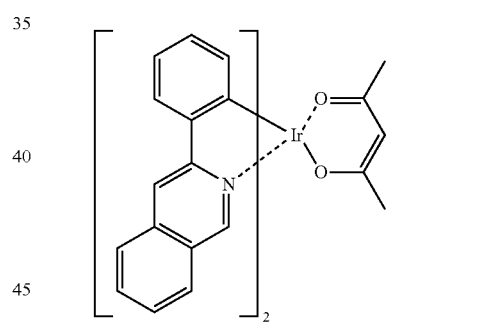
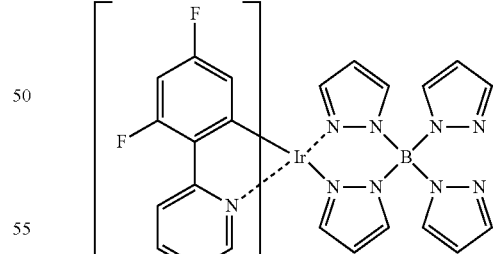
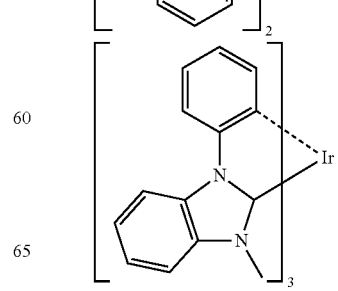

111
-continued
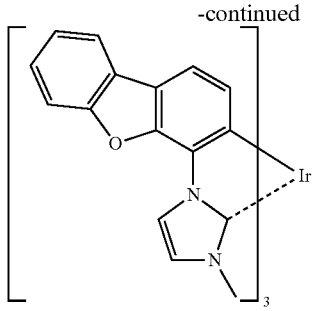
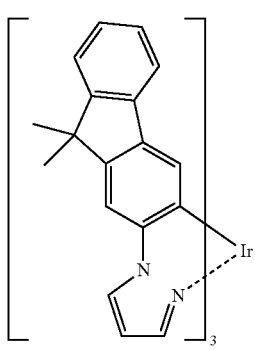
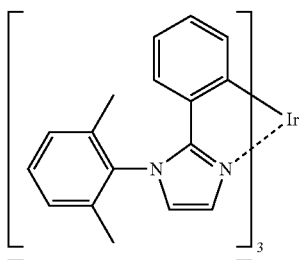
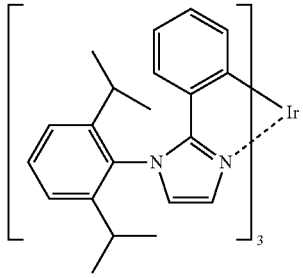
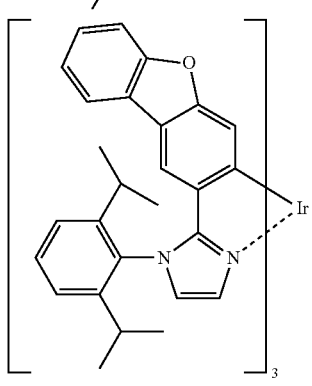
112
-continued
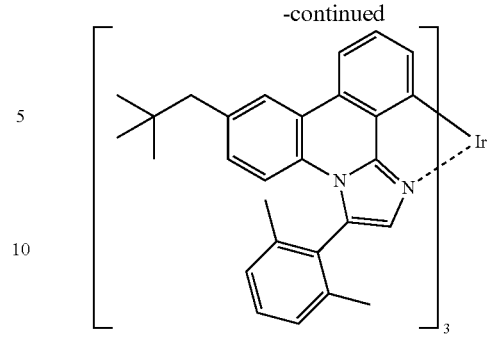
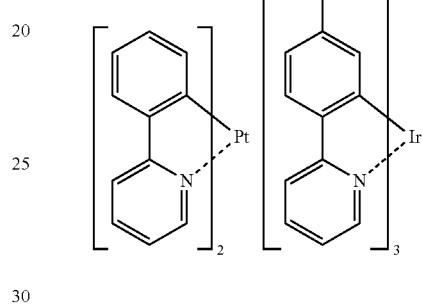
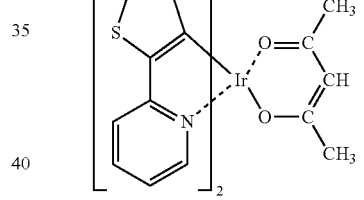
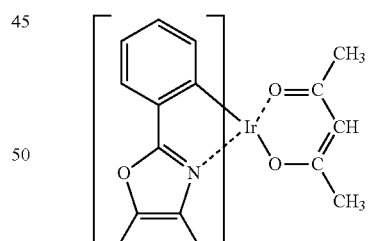
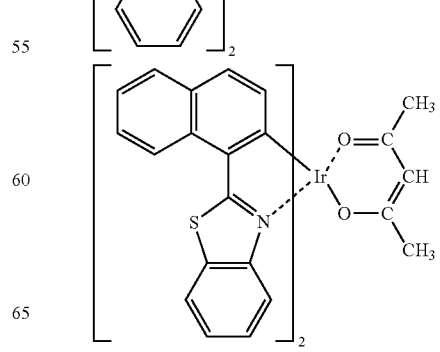

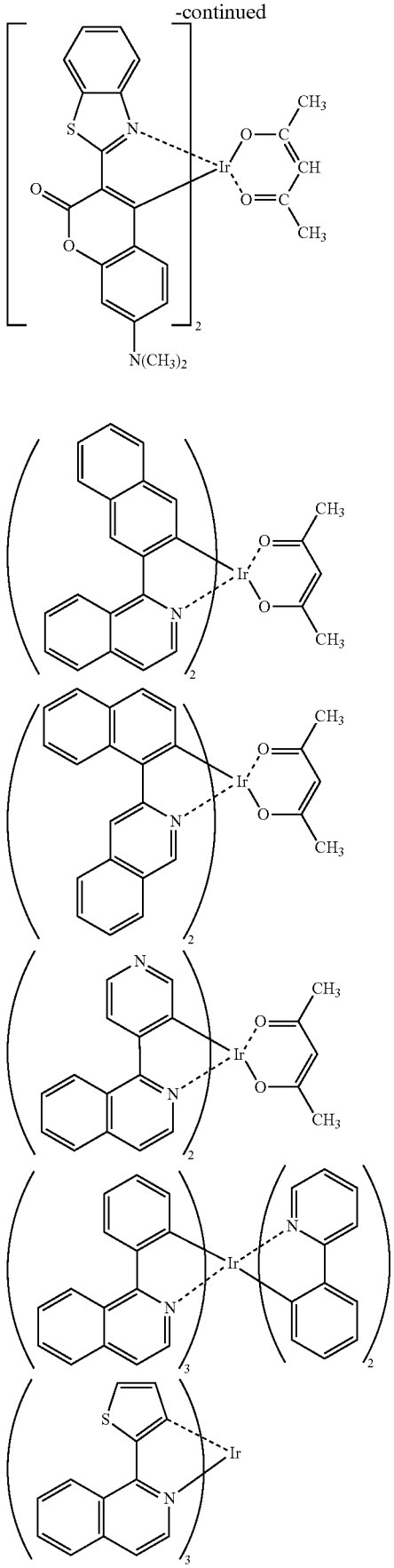

The light emitting layer of the organic EL device preferably comprises the host material comprising the material for organic EL device of the invention and the phosphorescent emitting material. The phosphorescent emitting material is preferably a blue-emitting metal complex having a maximum emitting wavelength of 550 nm, preferably 500 nm or less.

In a preferred embodiment of the invention, the organic EL device may comprise a hole transporting layer (hole injecting layer) and the hole transporting layer (hole injecting layer) comprises the material for organic EL device of the invention.

The organic EL device of the invention may contain an electron-donating dopant preferably in the interfacial region between the cathode and the organic thin film layer, more preferably in the interfacial region between the cathode and the electron transporting zone. The electron-donating dopant is a metal having a work function of 3.8 eV or less or a compound containing such metal. Examples thereof include at least one selected from alkali metal, alkali metal complex, alkali metal compound, alkaline earth metal, alkaline earth metal complex, alkaline earth metal compound, rare earth metal, rare earth metal complex, and rare earth metal compound.

Examples of the alkali metal include Li(work function: 2.9 eV), Na (work function: 2.36 eV), K (work function: 2.28 eV), Rb (work function: 2.16 eV), and Cs (work function: 1.95 eV), with those having a work function of 2.9 eV or less being particularly preferred. Of the above, preferred are K, Rb, and Cs, more preferred are Rb and Cs, and most preferred is Cs.

Examples of the alkaline earth metal include Ca (work function: 2.9 eV), Sr (work function: 2.0 to 2.5 eV), and Ba (work function: 2.52 eV), with those having a work function of 2.9 eV or less being particularly preferred.

Examples of the rare earth metal include Sc, Y, Ce, Tb, and Yb, with those having a work function of 2.9 eV or less being particularly preferred.

The preferred metals mentioned above have a high reducing ability and can improve the emission luminance and the lifetime of the organic EL device by the addition into the electron injecting zone in a relatively small amount.

Examples of the alkali metal compound include alkali oxide, such as $Li_2O$, $Cs_2O$, $K_2O$, and alkali halide, such as LiF, NaF, CsF, and KF, with LiF, $Li_2O$, and NaF being preferred.

Examples of the alkaline earth metal compound include BaO, SrO, CaO, and mixture thereof, such as $Ba_xSr_{1-x}O$ (0<x<1) and $Ba_xCA_{1-x}O$ (0<x<1), with BaO, SrO, and CaO being preferred.

Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, alkaline earth metal complex, and rare earth metal are not particularly limited as long as each containing at least one metal ion selected from alkali metal ions, alkaline earth metal ions, and rare earth metal ions, respectively. The ligand is preferably, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzoimidazole, hydroxybenzotriazole, hydroxyfulborane, bipyridyl, phenanthroline, phthalocyanine, porphyrin, cyclopentadiene, β-diketones, azomethines, and derivative thereof.

The electron-donating dopant is added to the interfacial region preferably into a form of layer or island. The electron-donating dopant is added preferably by co-depositing the electron-donating dopant with the organic compound (light emitting material, electron injecting material, etc.) for forming the interfacial region by a resistance heating deposition method, thereby dispersing the electron-donating dopant into the organic material. The disperse concentration expressed by the molar ratio of the organic material and the electron-donating dopant is 100:1 to 1:100 and preferably 5:1 to 1:5. When the electron-donating dopant is formed into a form of layer, a light emitting material or an electron injecting material is made into a layer which serves as an organic layer in the interface, and then, the electron-donating dopant alone is deposited by a resistance heating deposition method into a layer having a thickness preferably 0.1 to 15 nm. When the electron-donating dopant is formed into a form of island, a light emitting material or an electron injecting material is made into a form of island which serves as an organic layer in the interface, and then, the electron-donating dopant alone is deposited by a resistance heating deposition method into a form of island having a thickness preferably 0.05 to 1 nm.

In a preferred embodiment of the invention, the organic EL device may comprise an electron injecting layer between the light emitting layer and the cathode and the electron injecting layer comprises a nitrogen-containing heterocyclic derivative preferably in an amount of 50% by mass or more. The electron transporting material for use in the electron injecting layer is preferably an aromatic heterocyclic compound having at least one heteroatom in its molecule and particularly preferably a nitrogen-containing heterocyclic derivative.

The nitrogen-containing heterocyclic derivative is preferably a chelate metal complex having a nitrogen-containing heteroring, which is represented by formula (A).

The nitrogen-containing heterocyclic derivative is preferably a chelate metal complex having a nitrogen-containing heteroring, which is represented by formula (A):

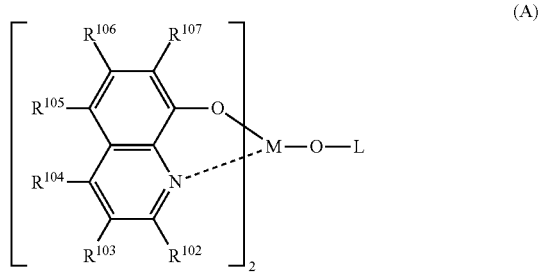

(A)

wherein $R^{102}$ to $R^{107}$ each independently represent a hydrogen atom, a halogen atom, an amino group, a hydrocarbon group having 1 to 40 carbon atoms, an alkoxy group, an aryloxy group, an alkoxycarbonyl group, or a heterocyclic group, each being optionally substituted.

Examples of the halogen atom include those mentioned above. Examples of the amino group which may be substituted include the alkylamino group, the arylamino group, and the aralkylamino group mentioned above.

Examples of the hydrocarbon group having 1 to 40 carbon atoms include a substituted or unsubstituted alkyl group, alkenyl group, a cycloalkyl group, an aryl group, and an aralkyl group. Examples of the alkyl group, alkenyl group, cycloalkyl group, alkoxy group, aryl group, heterocyclic group, aralkyl group, and aryloxy group include those mentioned above. The alkoxycarbonyl group is represented by —COOY', wherein Y' is an alkyl group as described above.

M is aluminum (Al), gallium (Ga), or indium (In), with In being preferred.

L in formula (A) is a group represented by formula (A') or (A"):

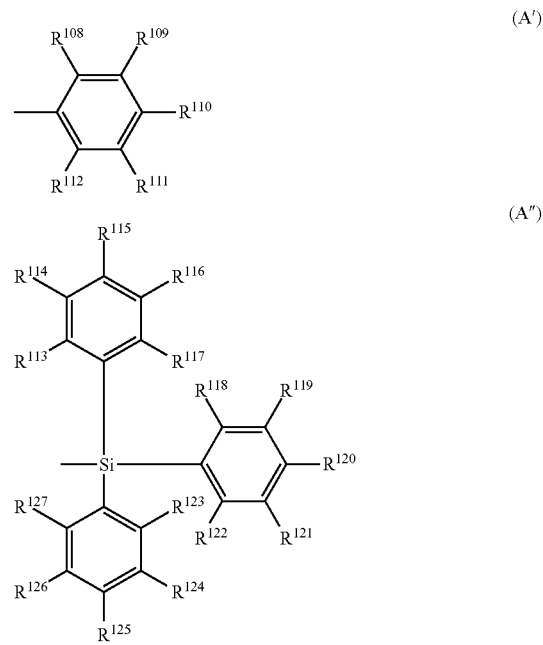

wherein $R^{108}$ to $R^{112}$ each independently represent a hydrogen atom or a substituted or unsubstituted hydrocarbon group having 1 to 40 carbon atoms and adjacent two groups may form a ring structure, and $R^{113}$ to $R^{127}$ each independently represent a hydrogen atom or a substituted or unsubstituted hydrocarbon group having 1 to 40 carbon atoms and adjacent two groups may form a ring structure.

Examples of the hydrocarbon group having 1 to 40 carbon atoms for $R^{108}$ to $R^{112}$ and $R^{113}$ to $R^{127}$ in formulae (A') and (A") are the same as those described above with respect to $R^2$ to $R^7$.

Examples of the divalent group formed by the adjacent two groups of $R^8$ to $R^{12}$ and $R^{13}$ to $R^{27}$ which completes the ring structure include tetramethylene group, pentamethylene group, hexamethylene group, diphenylmethane-2,2'-diyl group, diphenylethane-3,3'-diyl group, and diphenylpropane-4,4'-diyl group.

The specific examples of the chelate metal complex having a nitrogen-containing heteroring represented by formula (A) are shown below, although not limited thereto.

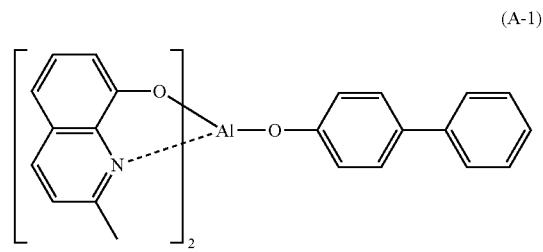

(A-1)

-continued (A-2)

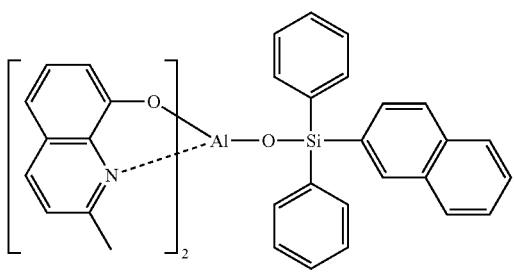

Examples of the nitrogen-containing heterocyclic derivative further include a nitrogen-containing compound other than the metal complex, for example, a nitrogen-containing heterocyclic derivative having the following formulae, such as a compound having a 5- or 6-membered ring which has the skeleton represented by formula (a) or a compound represented by formula (b).

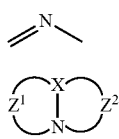 (a)

(b)

In formula (b), X is a carbon atom or a nitrogen atom. $Z^1$ and $Z^2$ each independently represent a group of atoms for completing the nitrogen-containing heteroring.

The nitrogen-containing heterocyclic derivative is more preferably an organic compound comprising a 5-membered or 6-membered nitrogen-containing aromatic polycyclic ring. If two or more nitrogen atoms are included, the nitrogen-containing aromatic polycyclic compound preferably has a skeleton of a combination of (a) and (b).

The nitrogen-containing group of the nitrogen-containing organic compound is selected, for example, from the nitrogen-containing heterocyclic groups shown below.

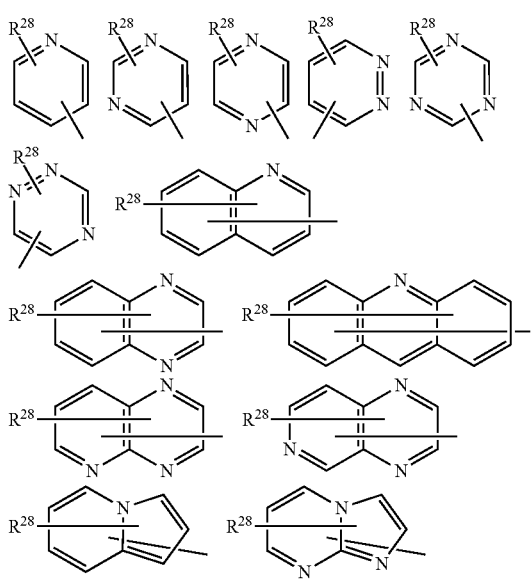

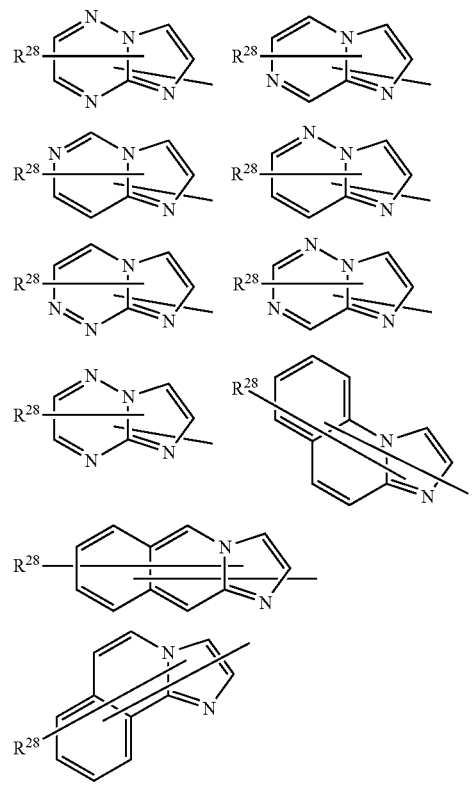

In each of the above formulae, $R^{28}$ is an aryl group having 6 to 40 carbon atoms, a heteroaryl group having 3 to 40 carbon atoms, an alkyl group having 1 to 20 carbon atoms, or an alkoxy group having 1 to 20 carbon atoms; and n is an integer of 0 to 5. If n is an integer of 2 or more, $R^{28}$ groups may be the same or different.

More preferred is a nitrogen-containing heterocyclic derivative represented by the following formula:

$$HAr^a\text{-}L^b\text{-}Ar^b\text{—}Ar^c$$

wherein $HAr^a$ is a nitrogen-containing heterocyclic group having 3 to 40 carbon atoms which may be substituted; $L^b$ is a single bond, an arylene group having 6 to 40 carbon atoms which may be substituted, or a heteroarylene group having 3 to 40 carbon atoms which may be substituted; $Ar^b$ is a divalent aromatic hydrocarbon group having 6 to 40 carbon atoms which may be substituted; and $Ar^c$ is an aryl group having 6 to 40 carbon atoms which may be substituted or a heteroaryl group having 3 to 40 carbon atoms which may be substituted.

$HAr^a$ is selected, for example, from the following groups:

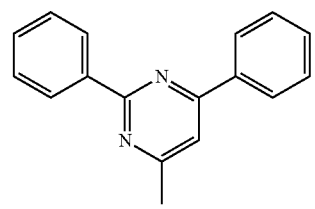

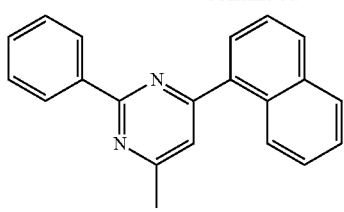
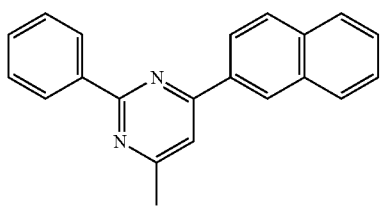
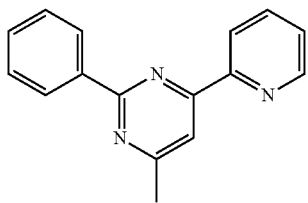
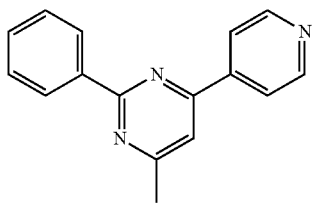
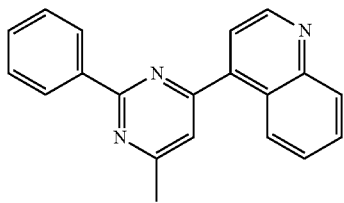
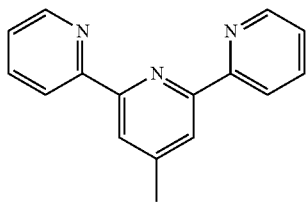
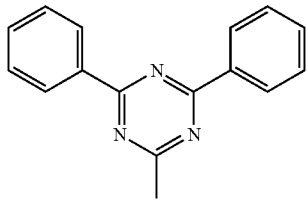
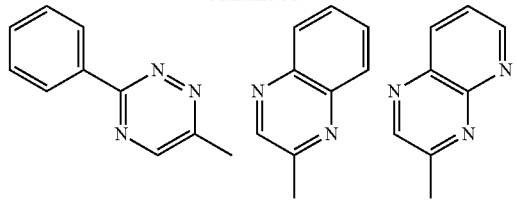
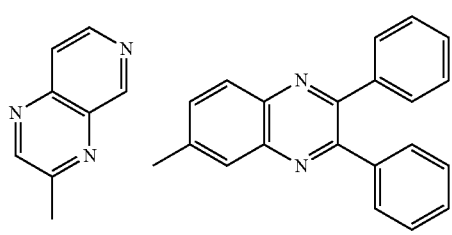
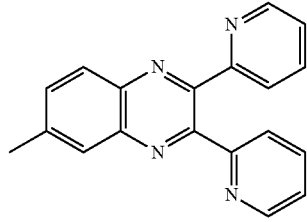
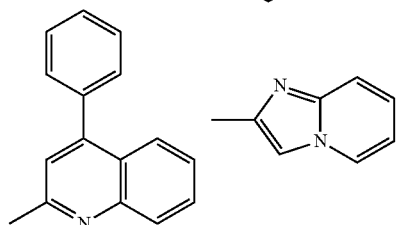
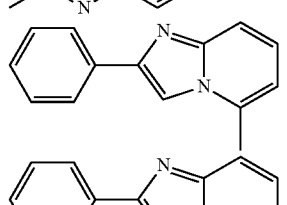
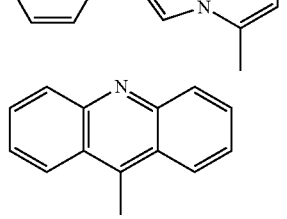
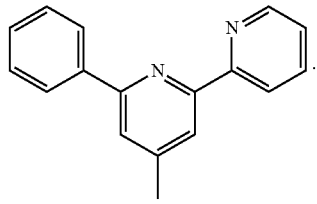
$L^6$ is selected, for example, from the following groups:
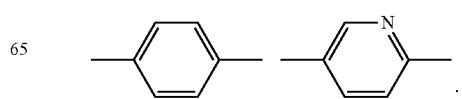

Ar$^c$ is selected, for example, from the following groups:

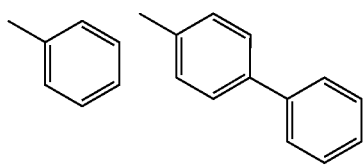

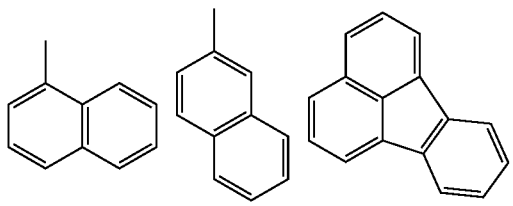

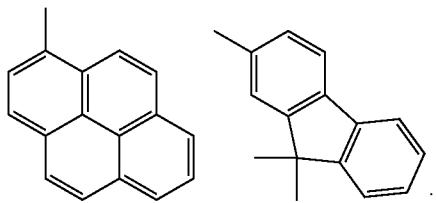

Ar$^b$ is selected, for example, from the following arylanthranyl groups:

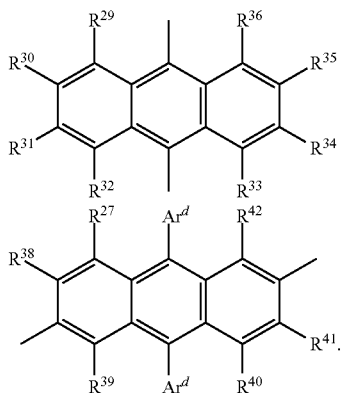

In the above formulae, R$^{29}$ to R$^{42}$ are each independently a hydrogen atom, a halogen atom, an alkyl group having 1 to 20 carbon atoms, an alkoxy group having 1 to 20 carbon atoms, an aryloxy group having 6 to 40 carbon atoms, an aryl group having 6 to 40 carbon atoms which may be substituted, or a heteroaryl group having 3 to 40 carbon atoms which may be substituted; and Ar$^d$ is an aryl group having 6 to 40 carbon atoms which may be substituted or a heteroaryl group having 3 to 40 carbon atoms which may be substituted.

The Ar$^b$ group represented by the above formulae is preferably a nitrogen-containing heterocyclic derivative wherein R$^{29}$ to R$^{36}$ are all hydrogen atoms.

The electron transporting layer preferably contains at least one of the nitrogen-containing heterocyclic derivatives represented by formulae (201) to (203):

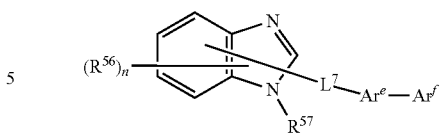 (201)

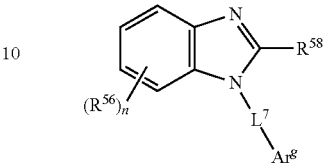 (202)

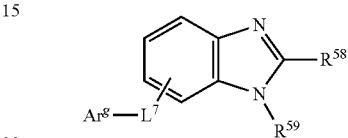 (203)

wherein R$^{56}$ is a hydrogen atom, a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms; n is an integer of 0 to 4; R$^{57}$ is a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or an alkoxy group having 1 to 20 carbon atoms; R$^{58}$ and R$^{59}$ are each independently a hydrogen atom, a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms; L$^7$ is a single bond, a substituted or unsubstituted arylene group having 6 to 60 carbon atoms, a substituted or unsubstituted pyridinylene group, a substituted or unsubstituted quinolinylene group, or a substituted or unsubstituted fluorenylene group; Ar$^e$ is a substituted or unsubstituted arylene group having 6 to 60 carbon atoms, a substituted or unsubstituted pyridinylene group, or a substituted or unsubstituted quinolinylene group; and Ar$^f$ is a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms.

Ar$^g$ is a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, a substituted or unsubstituted alkoxy group having 1 to 20 carbon atoms, or a group represented by —Ar$^e$—Ar$^f$ wherein Ar$^e$ and Ar$^f$ are as defined above.

In formulae (201) to (203), R$^{56}$ is a hydrogen atom, a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms.

Examples of the aryl group having 6 to 60 carbon atoms, preferably 6 to 40 carbon atoms, and more preferably 6 to 20 carbon atoms include phenyl group, naphthyl group, anthryl group, phenanthryl group, naphthacenyl group, chrysenyl group, pyrenyl group, biphenyl group, terphenyl group, tolyl group, t-butylphenyl group, (2-phenylpropyl)phenyl group, fluoranthenyl group, fluorenyl group, a monovalent residue of spirobifluorene, perfluorophenyl group, perfluoronaphthyl group, perfluoroanthryl group, perfluorobiphenyl group, a monovalent residue of 9-phenylanthracene, a monovalent residue of 9-(1'-naphthyl)anthracene, a monovalent residue of 9-(2'-naphthyl)anthracene, a monovalent residue of 6-phenylchrysene, and a monovalent residue of 9-[4-(diphenylamino)phenyl]anthracene, with phenyl group, naphthyl group, biphenyl group, terphenyl group, 9-(10-phenyl)anthryl group, 9-[10-(1'-naphthyl)]anthryl group, and 9-[10-(2'-naphthyl)]anthryl group being preferred.

Examples of the alkyl group having 1 to 20 carbon atoms, preferably 1 to 6 carbon atoms include methyl group, ethyl group, propyl group, butyl group, pentyl group, hexyl group, and a haloalkyl group, such as trifluoromethyl group. The alkyl group having 3 or more carbon atoms may be linear, cyclic or branched.

Examples of the alkoxy group having 1 to 20 carbon atoms, preferably 1 to 6 carbon atoms include methoxy group, ethoxy group, propoxy group, butoxy group, pentyloxy group, and hexyloxy group. The alkoxy group having 3 or more carbon atoms may be linear, cyclic or branched.

Examples of the substituent of the group represented by $R^{56}$ include a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms, and a substituted or unsubstituted heteroaryl group having 3 to 40 carbon atoms.

Examples of the halogen atom include fluorine, chlorine, bromine, and iodine.

Examples of the alkyl group having 1 to 20 carbon atoms, the alkoxy group having 1 to 20 carbon atoms, and the aryl group having 6 to 40 carbon atoms are the same as those described above.

Examples of the aryloxy group having 6 to 40 carbon atoms include phenoxy group and biphenyloxy group.

Examples of the heteroaryl group having 3 to 40 carbon atoms include pyrrolyl group, furyl group, thienyl group, silolyl group, pyridyl group, quinolyl group, isoquinolyl group, benzofuryl group, imidazolyl group, pyrimidyl group, carbazolyl group, selenophenyl group, oxadiazolyl group, and triazolyl group.

n is an integer of 0 to 4, preferably 0 to 2.

In formula (201), $R^{57}$ is a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or an alkoxy group having 1 to 20 carbon atoms.

Examples, preferred examples, and preferred carbon numbers of the above groups are the same as those described with respect to R.

In formulae (202) and (203), $R^{58}$ and $R^{59}$ are each independently a hydrogen atom, a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms.

Examples of each group, preferred carbon numbers, and examples of substituent of the groups are the same as those described with respect to $R^{56}$.

In formulae (201) to (203), $L^7$ is a single bond, a substituted or unsubstituted arylene group having 6 to 60 carbon atoms, a substituted or unsubstituted pyridinylene group, a substituted or unsubstituted quinolinylene group, or a substituted or unsubstituted fluorenylene group.

Preferably the arylene group has 6 to 40 carbon atoms and more preferably 6 to 20 carbon atoms. Examples thereof include divalent groups formed by removing one hydrogen atom from the aryl groups described with respect to R. Examples of the substituent of each group represented by $L^7$ are the same as those described with respect to $R^{56}$.

$L^7$ is preferably selected from the following group:

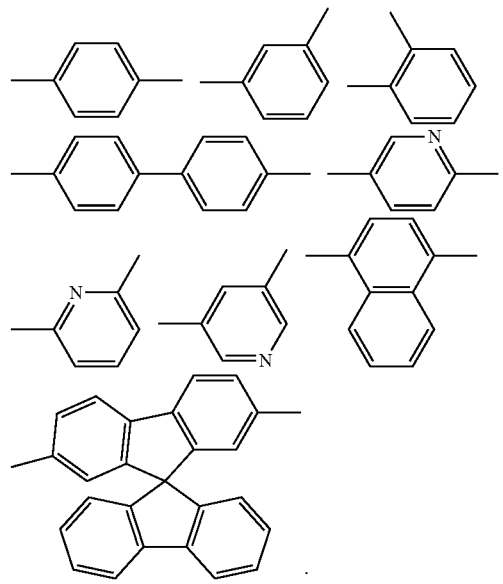

In formula (201), $Ar^e$ is a substituted or unsubstituted arylene group having 6 to 60 carbon atoms, a substituted or unsubstituted pyridinylene group, or a substituted or unsubstituted quinolinylene group. Examples of the substituent of each group represented by $Ar^e$ and $Ar^g$ are the same as those described with respect to R.

$Ar^e$ is preferably any one of condensed groups represented by the following formulae (101) to (110):

(101)

(102)

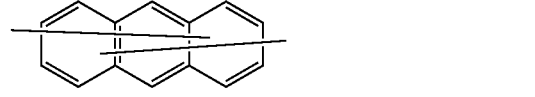

(103)

-continued

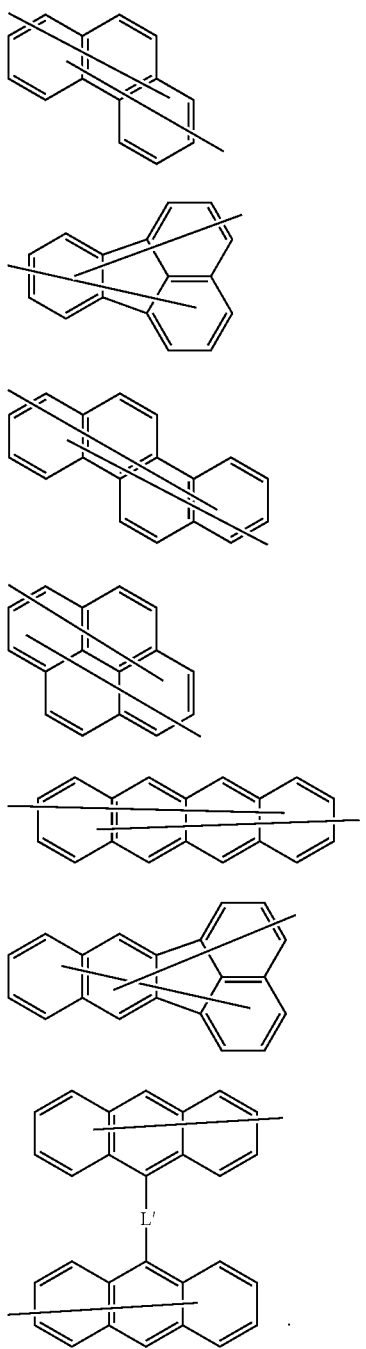

(104)

(105)

(106)

(107)

(108)

(109)

(110)

In formulae (101) to (110), each condensed ring may be substituted by a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms, or a substituted or unsubstituted heteroaryl group having 3 to 40 carbon atoms. If substituted by two or more substituents, the substituents may be the same or different. Examples of the substituent are the same as those described above.

In formula (110), L' is a single bond or a group selected from the following group:

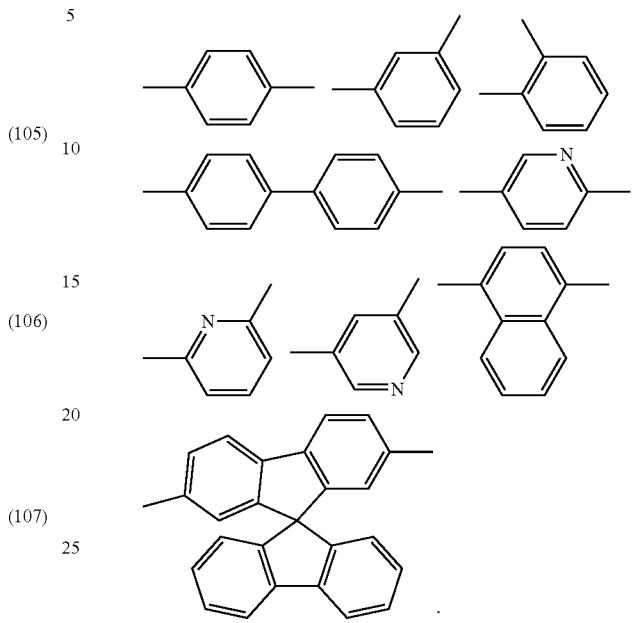

$Ar^e$ represented by formula (103) is preferably a condensed ring group represented by any of the following formulae (111) to (125):

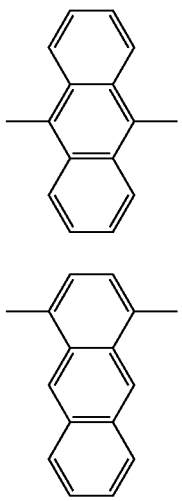

(111)

(112)

(113)

-continued
(114) 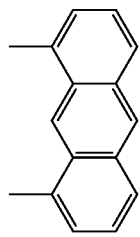
(115) 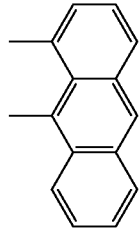
(116) 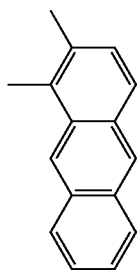
(117) 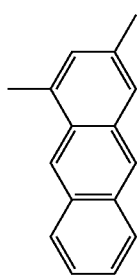
(118) 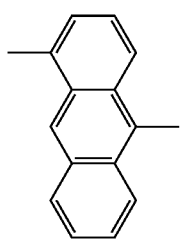
(119) 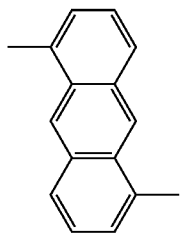
-continued
(120) 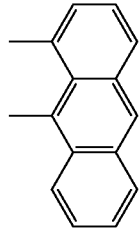
(121) 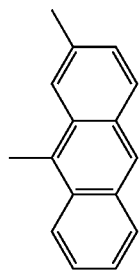
(122) 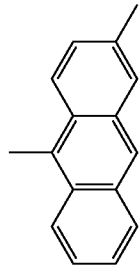
(123) 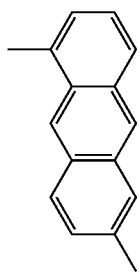
(124) 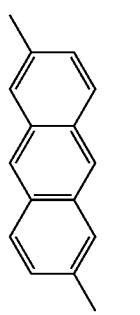

(125)

In formulae (111) to (125), each condensed ring may be substituted by a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms, or a substituted or unsubstituted heteroaryl group having 3 to 40 carbon atoms. If substituted by two or more substituents, the substituents may be the same or different. Examples of the substituent are the same as those described above.

In formula (201), $Ar^f$ is a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms.

Examples of each group, preferred carbon numbers, and examples of substituent are the same as those described with respect to $R^{56}$.

In formulae (202) and (203), $Ar^g$ is a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, a substituted or unsubstituted alkoxy group having 1 to 20 carbon atoms, or a group represented by —$Ar^e$—$Ar^f$ wherein $Ar^e$ and $Ar^f$ are as defined above.

Examples of each group, preferred carbon numbers, and examples of substituent are the same as those described with respect to $R^{56}$.

$Ar^g$ is preferably a condensed ring group represented by any of the following formulae (126) to (135):

(126)

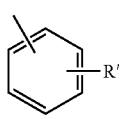

(127)

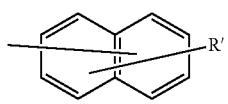

(128)

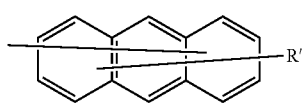

(129)

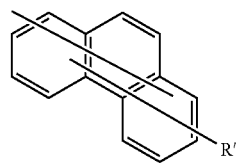

(130)

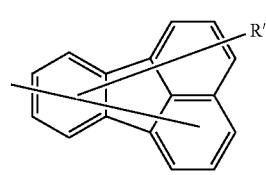

(131)

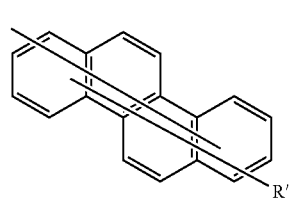

(132)

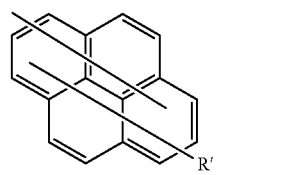

(133)

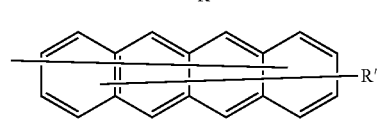

(134)

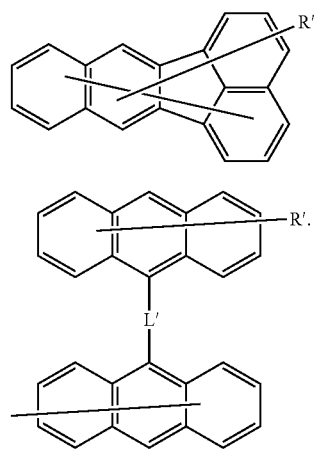

(135)

In formulae (126) to (135), each condensed ring may be substituted by a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms, or a substituted or unsubstituted heteroaryl group having 3 to 40 carbon atoms. If substituted by two or more substituents, the substituents may be the same or different. Examples of the substituent are the same as those described above.

In formula (135), L' is as defined above.

In formulae (126) to (135), R' is a hydrogen atom, a substituted or unsubstituted alkyl group having 1 to 20 carbon atoms, a substituted or unsubstituted aryl group having 6 to 40 carbon atoms, or a substituted or unsubstituted heteroaryl group having 3 to 40 carbon atoms. Examples thereof are the same as those described above.
Ar$^g$ represented by formula (128) is preferably a condensed ring group represented by the following formulae (136) to (158):
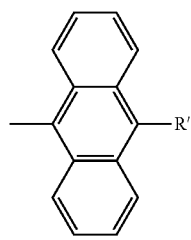
(136)
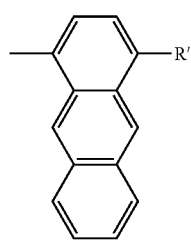
(137)
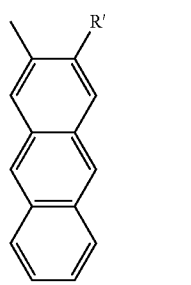
(138)
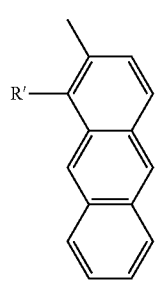
(139)
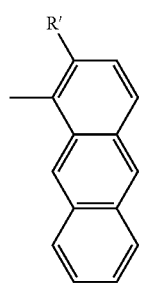
(140)
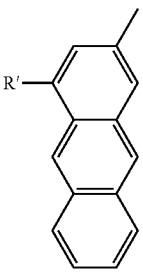
(141)
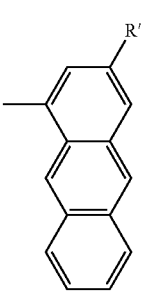
(142)
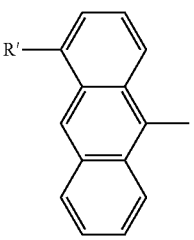
(143)
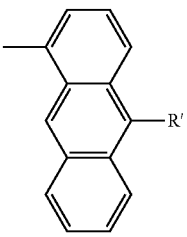
(144)
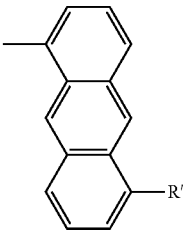
(145)
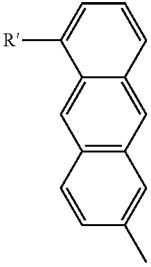
(146)

(147) 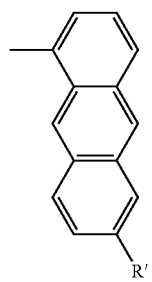
(148) 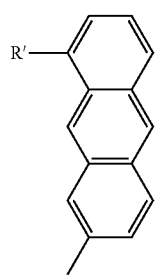
(149) 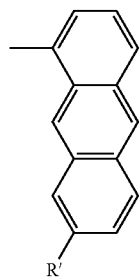
(150) 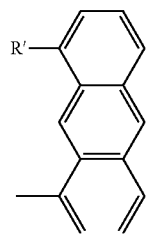
(151) 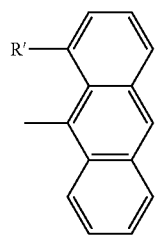
(152) 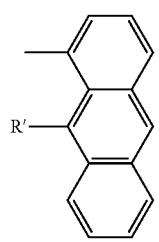
(153) 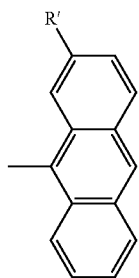
(154) 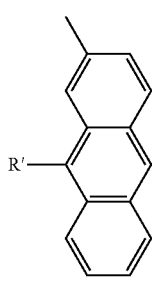
(155) 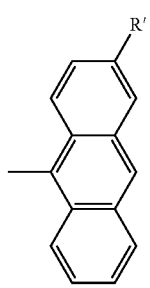
(156) 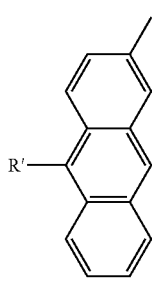
(157) 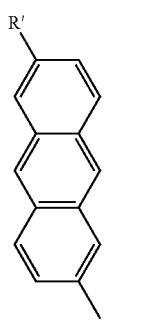

-continued (158)

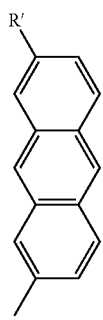

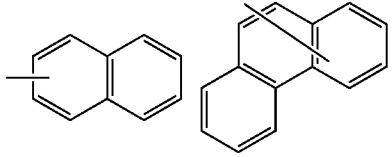

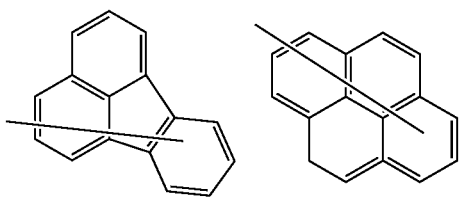

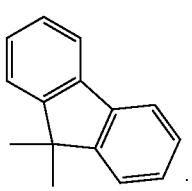

In formulae (136) to (158), each condensed ring may be substituted by a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms, or a substituted or unsubstituted heteroaryl group having 3 to 40 carbon atoms. If substituted by two or more substituents, the substituents may be the same or different. Examples of the substituent are the same as those described above. R' is as defined above.

Each of $Ar^f$ and $Ar^g$ is preferably selected from the following groups:

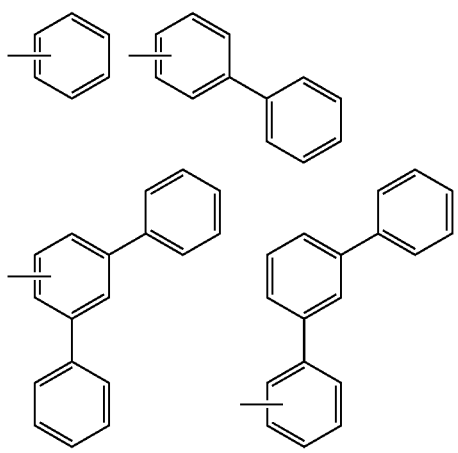

Examples of the nitrogen-containing heterocyclic derivative represented by formulae (201) to (203) are shown below, although not limited to the following exemplary compounds.

In the following table, HAr is the following structure in formulae (201) to (203).

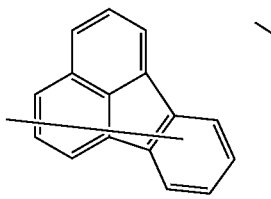

| HAr—$L^7$—$Ar^e$—$Ar^f$ | | | |
|---|---|---|---|
| HAr | $L^7$ | $Ar^e$ | $Ar^f$ |
| 1 | 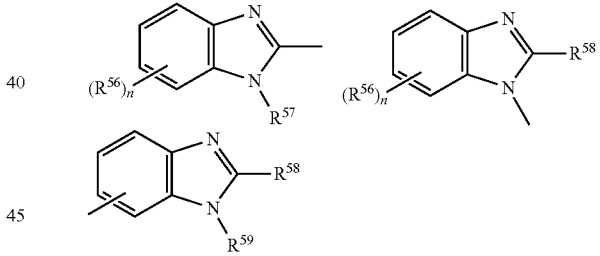 | | |

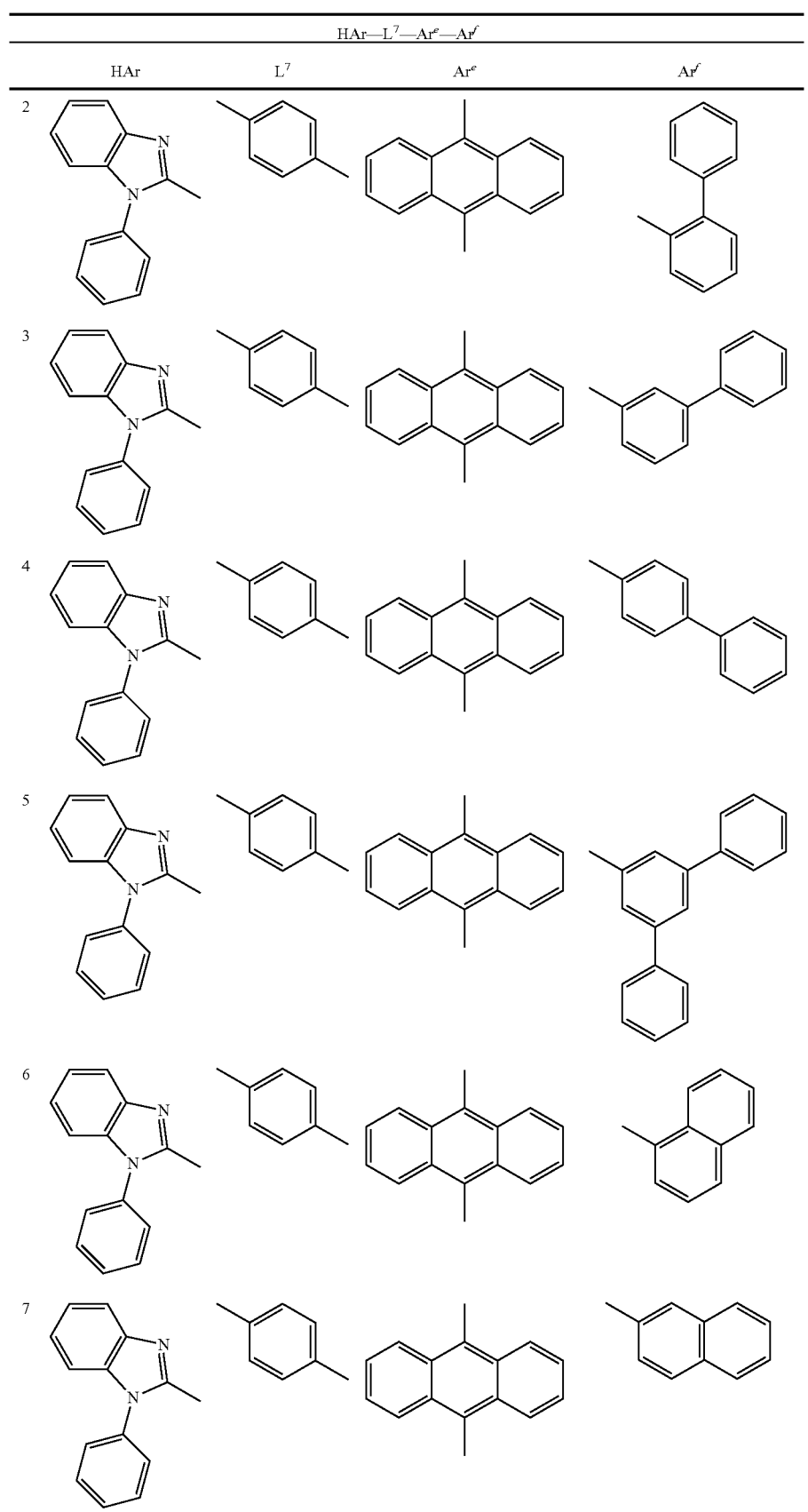

| HAr—L⁷—Arᵉ—Ar^f | | | |
|---|---|---|---|
| HAr | L⁷ | Arᵉ | Ar^f |

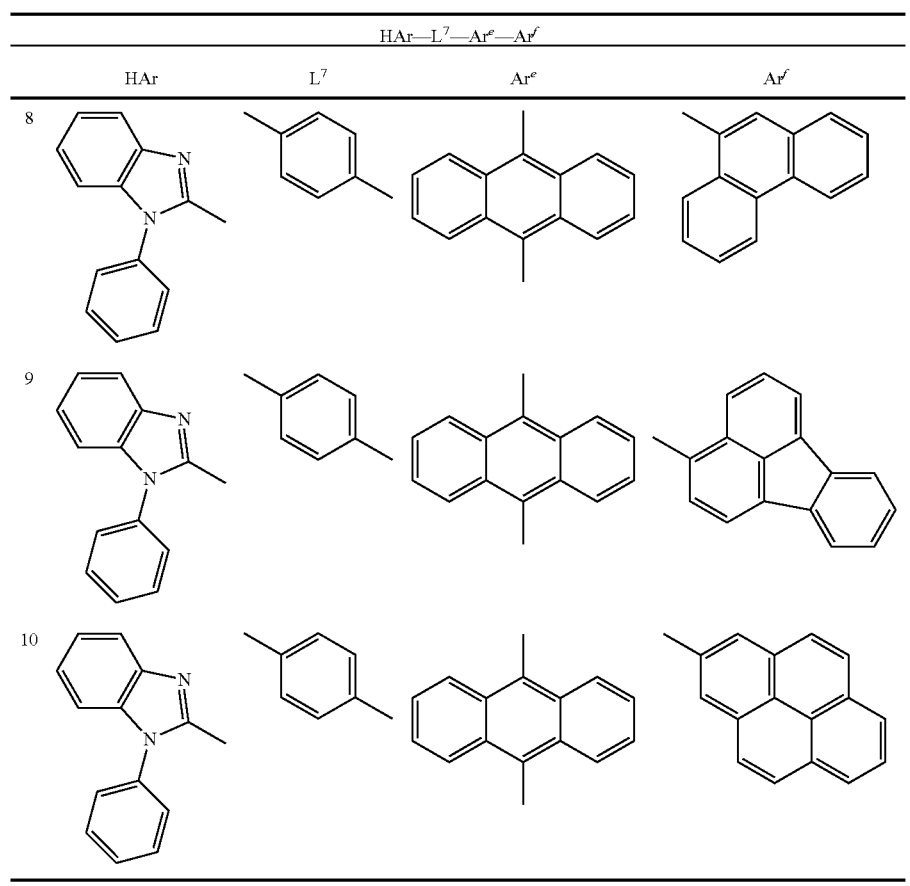

Another preferred example of the nitrogen-containing heterocyclic derivative includes a nitrogen-containing, five-membered ring derivative. The nitrogen-containing, five-membered ring may include, for example, imidazole ring, triazole ring, tetrazole ring, oxadiazole ring, thiadiazole ring, oxatriazole ring, and thiatriazole ring. The nitrogen-containing, five-membered ring derivative may be, for example, benzimidazole ring, benzotriazole ring, pyridinoimidazole ring, pyrimidinoimidazole ring, and pyridazinoimidazole ring, and is particularly preferably represented by formula (B):

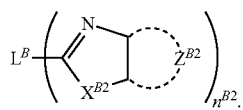

(B)

In the formula B, $L^B$ is a two- or more-valent linker such as carbon atom, silicon atom, nitrogen atom, boron atom, oxygen atom, sulfur atom, metal atom (for example, barium atom and beryllium atom), aromatic hydrocarbon ring, and heteroaromatic ring, with carbon atom, nitrogen atom, silicon atom, boron atom, oxygen atom, sulfur atom, aromatic hydrocarbon ring and heteroaromatic group being preferred, and carbon atom, silicon atom, aromatic hydrocarbon ring and heteroaromatic group being more preferred.

The aromatic hydrocarbon ring and heteroaromatic group for $L^B$ may be substituted. The substituent group is preferably alkyl group, alkenyl group, alkynylgroup, aryl group, amino group, alkoxy group, aryloxy group, acyl group, alkoxycarbonyl group, aryloxycarbonyl group, acyloxy group, acylamino group, alkoxycarbonylamino group, aryloxycarbonylamino group, sulfonylamino group, sulfamoyl group, carbamoyl group, alkylthio group, arylthio group, sulfonyl group, halogen atom, cyano group, or heteroaromatic group; more preferably alkyl group, aryl group, alkoxy group, aryloxy group, halogen atom, cyano group, or heteroaromatic group; still more preferably alkyl group, aryl group, alkoxy group, aryloxy group, or heteroaromatic group; and particularly preferably alkyl group, aryl group, alkoxy group, or heteroaromatic group.

Specific examples of $L^B$ are shown below.

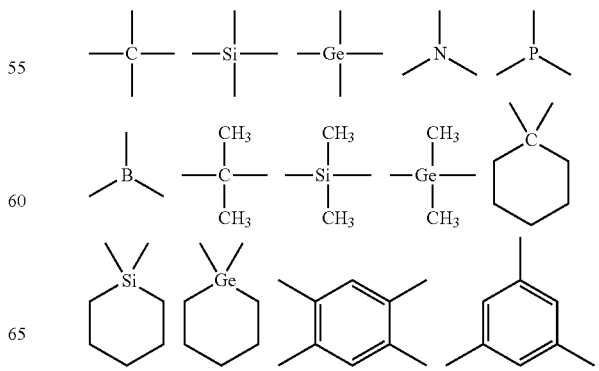

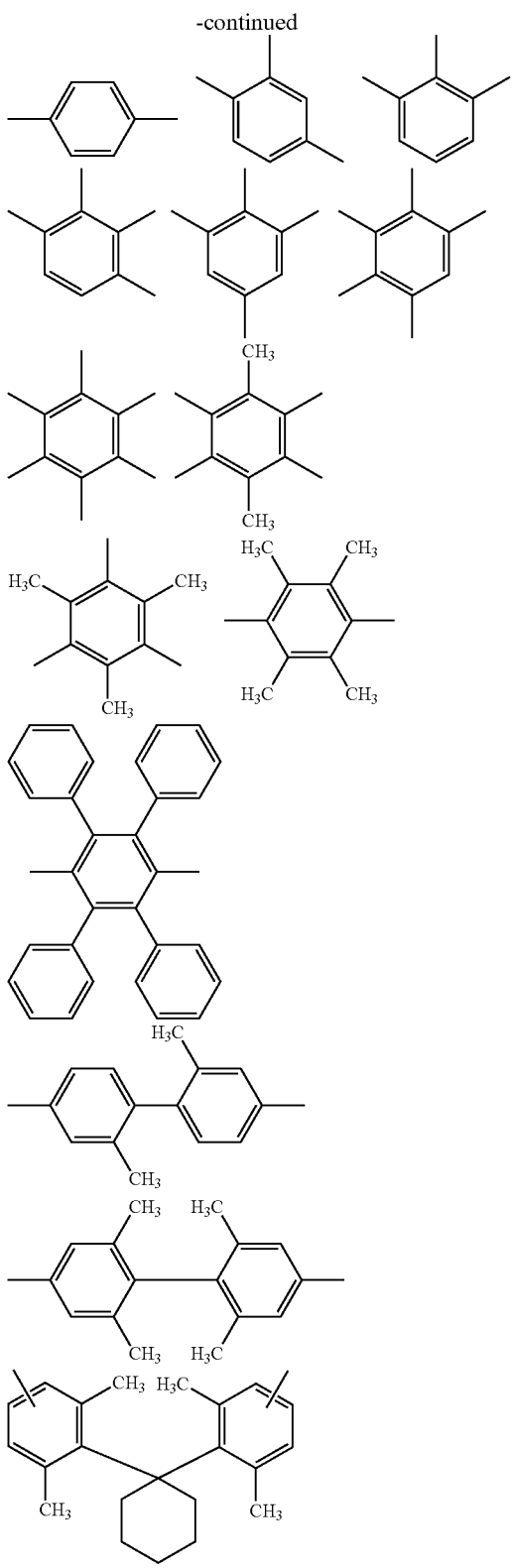

-continued $X^{B2}$ in formula (B) is —O—, —S— or —N($R^{B2}$)—. $R^{B2}$ is a hydrogen atom, an aliphatic hydrocarbon group, an aryl group or a heterocyclic group.

The aliphatic hydrocarbon group for $R^{B2}$ may be a linear or branched alkyl group preferably having 1 to 20 carbon atoms, more preferably 1 to 12 carbon atoms and particularly preferably 1 to 8 carbon atoms, such as methyl group, ethyl group, isopropyl group, t-butyl group, n-octyl group, n-decyl group, and n-hexadecyl group; a cycloalkyl group preferably having 3 to 10 ring carbon atoms, such as cyclopropyl group, cyclopentyl group, and cyclohexyl group; an alkenyl group preferably having 2 to 20 carbon atoms, more preferably 2 to 12 carbon atoms and particularly preferably 2 to 8 carbon atoms, such as vinyl group, allyl group, 2-butenyl group, and 3-pentenyl group; and an alkynyl group preferably having 2 to 20 carbon atoms, more preferably 2 to 12 carbon atoms and particularly preferably 2 to 8 carbon atoms, such as propargyl group and 3-pentynyl group, with alkyl group being preferred.

The aryl group for $R^{B2}$ is a monocyclic or condensed aryl group and has preferably 6 to 30 ring carbon atoms, more preferably 6 to 20 ring carbon atoms and still more preferably 6 to 12 ring carbon atoms. Examples thereof include phenyl group, 2-methylphenyl group, 3-methylphenyl group, 4-methylphenyl group, 2-methoxyphenyl group, 3-trifluoromethylphenyl group, pentafluorophenyl group, 1-naphthyl group, and 2-naphthyl group.

The heterocyclic group for $R^{B2}$ is a monocyclic or condensed heterocyclic group, preferably a heteroaromatic group having at least one heteroatom selected from nitrogen atom, oxygen atom, sulfur atom and selenium atom, and has preferably 1 to 20 ring carbon atoms, more preferably 1 to 12 ring carbon atoms and still more preferably 2 to 10 ring carbon atoms. Examples of the heterocyclic group include the residues of pyrrolidine, piperidine, piperazine, morpholine, thiophene, selenophene, furan, pyrrole, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzimidazole, benzoxazole, benzothiazole, benzotriazole, tetraazaindene, carbazole, and azepine, with the residues of furan, thiophene, pyridine, pyrazine, pyrimidine, pyridazine, triazine, quinoline, phthalazine, naphthyridine, quinoxaline, and quinazoline being preferred, the residues of furan, thiophene, pyridine, and quinoline being more preferred, and a quinolinyl group being still more preferred.

The aliphatic hydrocarbon group, aryl group and heterocyclic group for $R^{B2}$ may be substituted. The substituent is preferably an alkyl group, an alkenyl group, an alkynyl-group, an aryl group, an amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano group, or a heteroaromatic group; more preferably an alkyl group, an aryl group, an alkoxy group, an aryloxy group, a halogen atom, a cyano group, or a heteroaromatic group; still more preferably an alkyl group, an aryl group, an alkoxy group, an aryloxy group, or a heteroaromatic group; and particularly preferably an alkyl group, an aryl group, an alkoxy group, or a heteroaromatic group.

$R^{B2}$ is preferably an aliphatic hydrocarbon group, an aryl group or a heterocyclic group, more preferably an aliphatic hydrocarbon group (having preferably 6 to 30 carbon atoms, more preferably 6 to 20 carbon atoms, and still more preferably 6 to 12 carbon atoms) or an aryl group, and still more preferably an aliphatic hydrocarbon group (having preferably 1 to 20 carbon atoms, more preferably 1 to 12 carbon atoms, and still more preferably 2 to 10 carbon atoms).

$X^{B2}$ is preferably —O— or —N($R^{B2}$)—, more preferably —N($R^{B2}$)—.

$Z^{B2}$ is a group of atoms to complete an aromatic ring. The aromatic ring formed by $Z^{B2}$ is either of an aromatic hydrocarbon ring or a heteroaromatic ring. Examples there of include benzene ring, pyridine ring, pyrazine ring, pyrimidine ring, pyridazine ring, triazine ring, pyrrole ring, furan ring, thiophene ring, selenophene ring, tellurophene ring, imidazole ring, thiazole ring, selenazole ring, tellurazole ring, thiadiazole ring, oxadiazole ring, and pyrazole ring, with benzene ring, pyridine ring, pyrazine ring, pyrimidine ring, and pyridazine ring being preferred, benzene ring, pyridine ring, and pyrazine ring being more preferred, benzene ring and pyridine ring being still more preferred, and pyridine ring being particularly preferred.

The aromatic ring formed by $Z^{B2}$ may be fused with another ring to form a condensed ring and may be substituted. Examples of the substituent group are the same as the substituent groups for $L^B$ and preferably alkyl group, alkenyl group, alkynyl group, aryl group, amino group, alkoxy group, aryloxy group, acyl group, alkoxycarbonyl group, aryloxycarbonyl group, acyloxy group, acylamino group, alkoxycarbonylamino group, aryloxycarbonylamino group, sulfonylamino group, sulfamoyl group, carbamoyl group, alkylthio group, arylthio group, sulfonyl group, halogen atom, cyano group, and heterocyclic group; more preferably alkyl group, aryl group, alkoxy group, aryloxy group, halogen atom, cyano group, and heterocyclic group; still more preferably alkyl group, aryl group, alkoxy group, aryloxy group, and heteroaromatic group; and particularly preferably alkyl group, aryl group, alkoxy group, and heteroaromatic group.

$n^{B2}$ is an integer of 1 to 4, preferably 2 or 3.

The nitrogen-containing, five-membered ring derivative of formula (B) is preferably represented by the following formula (B'):

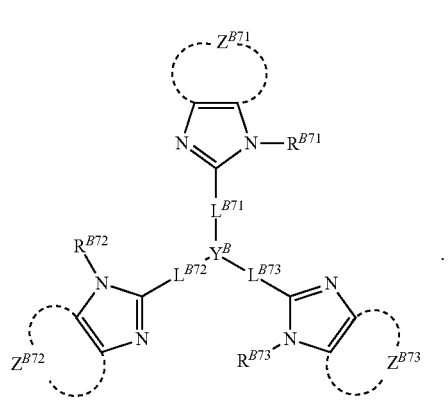

(B')

In formula (B'), $R^{B71}$, $R^{B72}$, $R^{B73}$ and their preferred examples are each respectively the same as defined in $R^{B2}$ of formula (B).

$Z^{B71}$, $Z^{B72}$, $Z^{B73}$ and their preferred examples are each respectively the same as defined in $Z^{B2}$ of formula (B).

$L^{B71}$, $L^{B72}$ and $L^{B73}$ are each independently a linking group which is selected from the divalent groups for $L^B$ of formula (B), preferably a single bond, a divalent aromatic hydrocarbon group, a divalent heteroaromatic group or a linking group composed of a combination thereof, with a single bond being preferred. $L^{B71}$, $L^{B72}$ and $L^{B73}$ may be substituted. The substituent and preferred substituent are the same as those for $L^B$ of formula (B).

$Y^B$ is a nitrogen atom, 1,3,5-benzenetriyl group or 2,4,6-triazinetriyl group. The 1,3,5-benzenetriyl group may be substituted at 2-, 4-, or 6-position, for example, by an alkyl group, an aromatic hydrocarbon group or a halogen atom.

Specific examples of the nitrogen-containing, five-membered ring derivative of the formulae (B) and (B') are shown below, although not limited thereto.

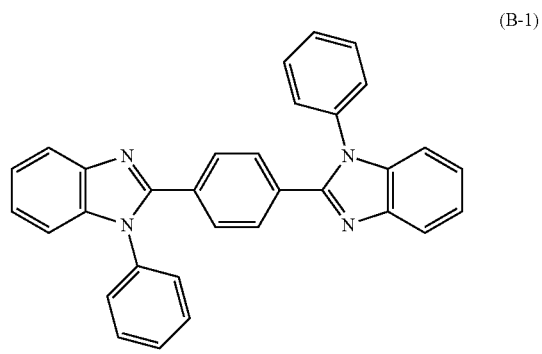

(B-1)

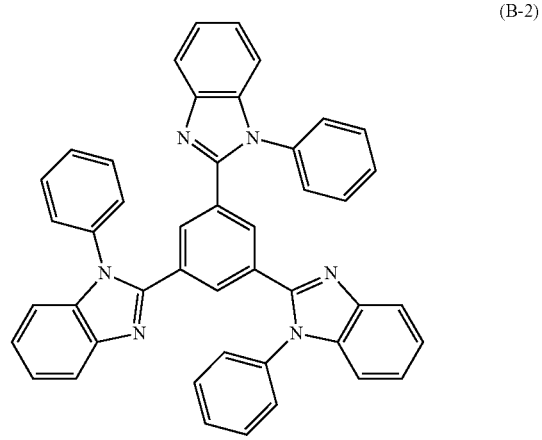

(B-2)

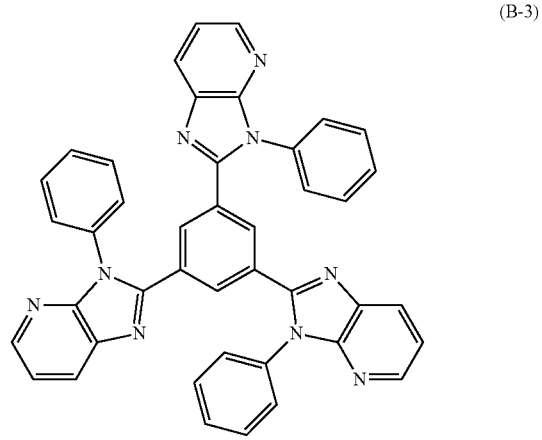

(B-3)

The compound for forming the electron injecting layer and electron transporting layer may further include a compound which has a structure wherein an electron-deficient, nitrogen-containing 5-membered ring or an electron-deficient, nitrogen-containing 6-membered ring is combined with a substituted or unsubstituted indole skeleton, a substituted or unsubstituted carbazole skeleton, or a substituted or unsubstituted azacarbazole skeleton. Preferred examples of the electron-deficient, nitrogen-containing 5-membered ring skeleton and the electron-deficient, nitrogen-containing 6-membered ring skeleton includes a pyridine, pyrimidine, pyrazine, triazine, triazole, oxadiazole, pyrazole, imidazole, quinoxaline, or pyrrole skeleton, and a condensed skeleton thereof, such as benzimidazole and imidazopyridine. The combination between the pyridine, pyrimidine, pyrazine or triazine skeleton with the carbazole, indole, azacarbazole or quinoxaline skeleton is preferred. Each skeleton may be either substituted or not substituted.

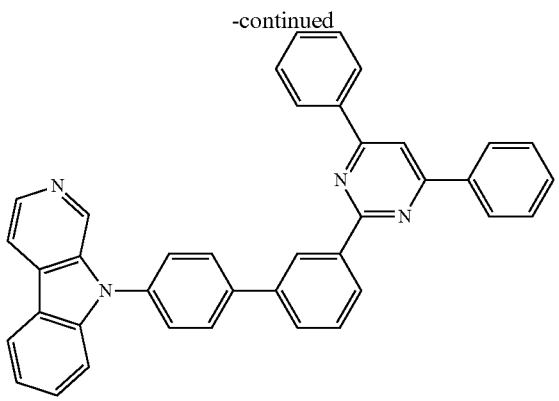

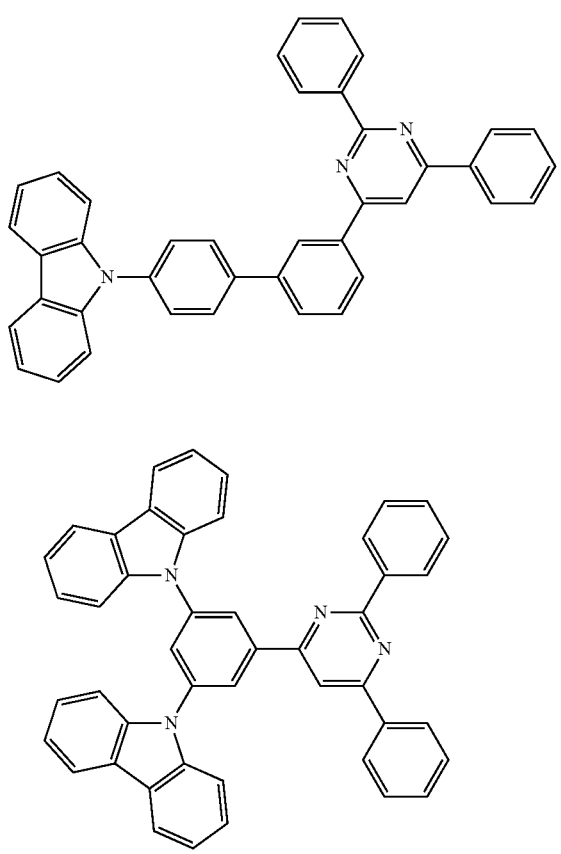

Examples of the electron transporting compound are shown below, although not limited thereto.

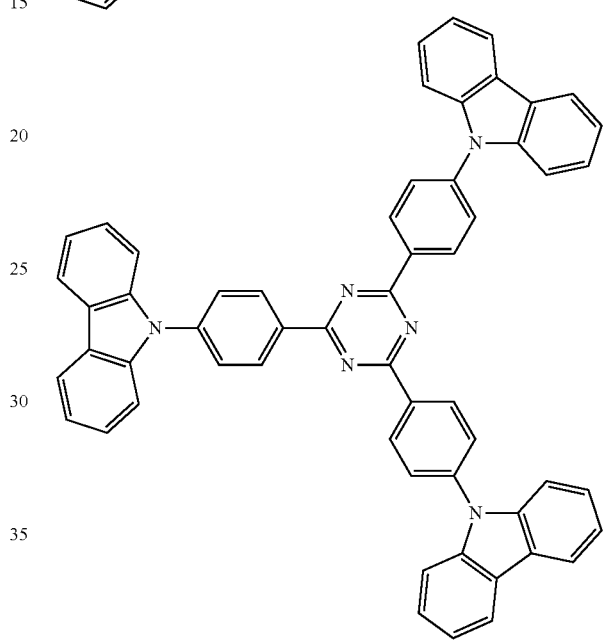

The electron injecting layer and electron transporting layer may be a single-layered structure made of one or more kinds of the materials mentioned above or a multi-layered structure of layers having the same composition or different compositions. The material for use in those layers preferably has a π-electron deficient, nitrogen-containing heterocyclic group.

The hole injecting layer or the hole transporting layer (inclusive of a hole injecting/transporting layer) is preferably formed from an aromatic amine compound, for example, an aromatic amine derivative represented by the following formula (1):

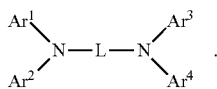

In formula (1), each of $Ar^1$ to $Ar^4$ is a substituted or unsubstituted aryl group having 6 to 50 ring carbon atoms or a substituted or unsubstituted heterocyclic group having 5 to 50 ring atoms.

Examples of the substituted or unsubstituted aryl group having 6 to 50 ring carbon atoms include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, fluoranthenyl group, and fluorenyl group.

Examples of the substituted or unsubstituted heterocyclic group having 5 to 50 ring atoms include 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1 isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group, with phenyl group, naphthyl group, biphenyl group, anthranyl group, phenanthryl group, pyrenyl group, chrysenyl group, fluoranthenyl group, and fluorenyl group being preferred.

L is a linking group, for example, a substituted or unsubstituted arylene group having 6 to 50 ring carbon atoms, a substituted or unsubstituted heteroarylene group having 5 to 50 ring atoms, or a divalent group derived from two or more arylene groups or heteroarylene groups by bonding these groups vis a single bond, an ether bond, a thioether bond, an alkylene group having 1 to 20 carbon atoms, an alkenylene group having 2 to 20 carbon atoms, or amino group. Examples of the arylene group having 6 to 50 ring carbon atoms include 1,4-phenylene group, 1,2-phenylene group, 1,3-phenylene group, 1,4-naphthylene group, 2,6-naphthylene group, 1,5-naphthylene group, 9,10-anthracenylene group, 9,10-phenanthrenylene group, 3,6-phenanthrenylene group, 1,6-pyrenylene group, 2,7-pyrenylene group, 6,12-chrysenylene group, 4,4'-biphenylene group, 3,3'-biphenylene group, 2,2'-biphenylene group, and 2,7-fluorenylene group. Examples of the heteroarylene group having 5 to 50 ring atoms include 2,5-thiophenylene group, 2,5-silolylene group, and 2,5-oxadiazolylene group. Of the above groups, preferred are 1,4-phenylene group, 1,2-phenylene group, 1,3-phenylene group, 1,4-naphthylene group, 9,10-anthracenylene group, 6,12-chrysenylene group, 4,4'-biphenylene group, 3,3'-biphenylene group, 2,2'-biphenylene group, and 2,7-fluorenylene group.

If L is a linking group having two or more arylene groups or heteroarylene groups, adjacent arylene groups or adjacent heteroarylene group may bond to each other via a divalent group to form a ring. Examples of the divalent group for completing such ring include tetramethylene group, pentamethylene group, hexamethylene group, diphenylmethane-2,2'-diyl group, diphenylethane-3,3'-diyl group, and diphenylpropane-4,4'-diyl group.

Examples of the substituent of $Ar^1$ to $Ar^4$ and L include a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted heteroaryloxy group having 5 to 50 ring atoms, a substituted or unsubstituted arylthio group having 6 to 50 ring carbon atoms, a substituted or unsubstituted heteroarylthio group having 5 to 50 ring atoms, a substituted or unsubstituted alkoxycarbonyl group having 2 to 50 carbon atoms, an amino group substituted by a substituted or unsubstituted aryl group having 6 to 50 ring carbon atoms or a substituted or unsubstituted heterocyclic group having 5 to 50 ring atoms, a halogen atom, a cyano group, a nitro group, and a hydroxyl group.

Examples of the substituted or unsubstituted aryl group having 6 to 50 ring carbon atoms include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, fluoranthenyl group, and fluorenyl group.

Examples of the substituted or unsubstituted heterocyclic group having 5 to 50 ring atoms include 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1 isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthrolin-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group.

Examples of the substituted or unsubstituted alkyl group having 1 to 50 carbon atoms include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichlorot-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, and 1,2,3-trinitropropyl group.

Examples of the substituted or unsubstituted cycloalkyl group having 3 to 50 carbon atoms include cyclopropyl group, cyclobutyl group, cyclopentyl group, cyclohexyl group, 4-methylcyclohexyl group, 1-adamantyl group, 2-adamantyl group, 1-norbornyl group, and 2-norbornyl group.

The substituted or unsubstituted alkoxy group having 1 to 50 carbon atoms is represented by —OY. Examples of Y include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, and 1,2,3-trinitropropyl group.

Examples of the substituted or unsubstituted aralkyl group having 7 to 50 carbon atoms include benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrol)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro-2-phenylisopropyl group.

The substituted or unsubstituted aryloxy group having 6 to 50 ring carbon atoms is represented by —OY'. Examples of Y' include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, and 4''-t-butyl-p-terphenyl-4-yl group.

The substituted or unsubstituted heteroaryloxy group having 5 to 50 ring atoms is represented by —OZ'. Examples of Z' include 2-pyrrolyl group, 3-pyrrolyl group, pyrazinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1 isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group.

The substituted or unsubstituted arylthio group having 6 to 50 ring carbon atoms is represented by —SY". Examples of Y" include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, and 4"-t-butyl-p-terphenyl-4-yl group.

The substituted or unsubstituted heteroarylthio group having 5 to 50 ring atoms is represented by —SZ". Examples of Z" include 2-pyrrolyl group, 3-pyrrolyl group, pyrazinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl 1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group.

The substituted or unsubstituted alkoxycarbonyl group having 2 to 50 carbon atoms is represented by —COOZ. Examples of Z include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, and 1,2,3-trinitropropyl group.

The amino group substituted by a substituted or unsubstituted aryl group having 6 to 50 ring carbon atoms or a substituted or unsubstituted heteroaryl group having 5 to 50 ring atoms is represented by —NPQ. Examples of P and Q include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl) phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, 2-pyrrolyl group, 3-pyrrolyl group, pyrazinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group.

Examples of the compound represented by formula (1) are shown below, although not limited thereto.

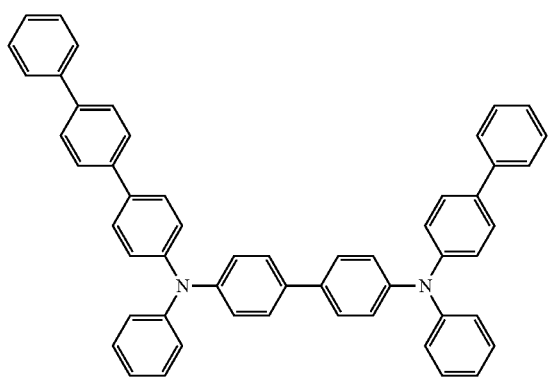

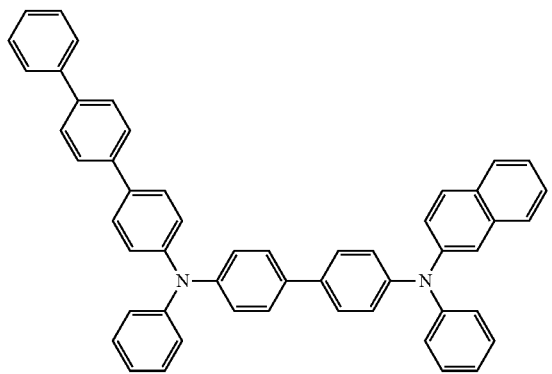

An aromatic amine represented by the following formula (II) is also preferably used to form the hole injecting layer or the hole transporting layer.

In formula (II), An to Ara are the same as defined in $Ar^1$ to $Ar^4$ of formula (I). Examples of the compound represented by formula (II) are shown below, although not limited thereto.

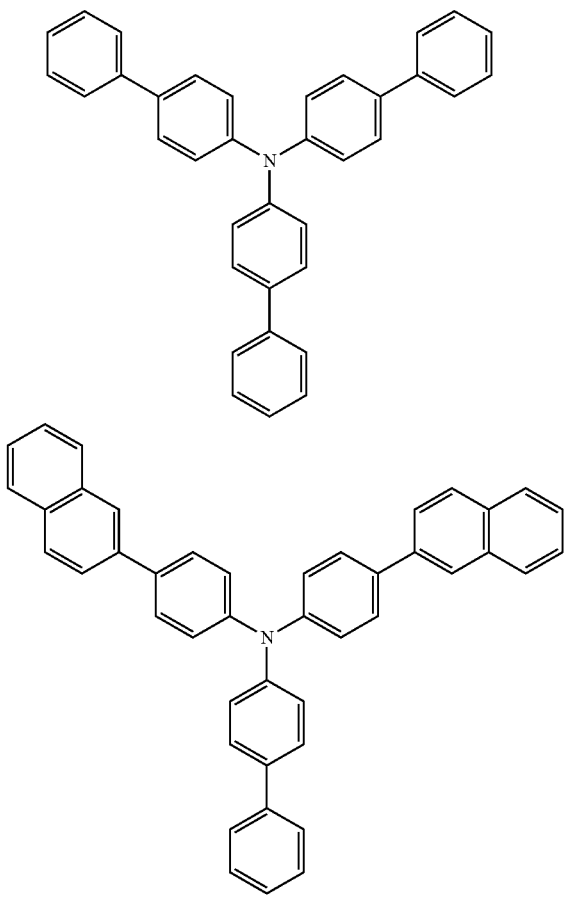

The anode of the organic EL device injects holes to the hole transporting layer or the light emitting layer, and an anode having a work function of 4.5 eV or more is effective. Examples of material for anode usable in the invention include indium tin oxide alloy (ITO), tin oxide (NESA), gold, silver, platinum, and cupper. The cathode is preferably formed from a material having a small work function because electrons are easily injected to the electron injecting layer or the light emitting layer. Examples of the material for cathode include, but not limited to, indium, aluminum, magnesium, magnesium-indium alloy, magnesium-aluminum alloy, aluminum-lithium alloy, aluminum-scandium-lithium alloy, and magnesium-silver alloy.

The method of forming each layer of the organic EL device of the invention is not particularly limited, and each layer can be formed by a known method, such as a vacuum vapor deposition method and a spin coating method. The organic thin film layer comprising the compound represented by formula (1) in the organic EL device of the invention may be formed by a known method, for example, by a vacuum vapor deposition method, a molecular beam evaporation method (MBE method), and a coating method using a solvent solution, such as a dipping method, a spin coating method, a casting method, a bar coating method and a roll coating method.

The film thickness of each organic layer in the organic EL device of the invention is not particularly limited. The defects, such as pinholes, are likely to be caused if the film thickness is excessively small. If the film thickness is excessively large, a high applied voltage is required to reduce the efficiency. Therefore, the film thickness is preferably selected from several nanometers to 1 μm.

EXAMPLES

The present invention will be described in more detail with reference to synthesis examples and examples. However, it should be noted that the scope of the invention is not limited to the following synthesis examples and examples.

Each organic EL device was evaluated by the following methods.

(1) External Quantum Efficiency (%)

The external quantum efficiency at a luminance of 1000 cd/m$^2$ was measured by a spectroradiometer (CS-1000 manufactured by Minolta) at 23° C. in a dry nitrogen gas atmosphere.

(2) Half Lifetime (h)

The time taken until the initial luminance (1000 cd/m$^2$) was reduced by half was measured while continuously passing direct current.

(3) Voltage (V)

Using Keithly 236 Source Measure Unit, a voltage was applied to a device which was electrically wired to cause light emission at 23° C. in a dry nitrogen gas atmosphere. The voltage applied to the device was determined by subtracting the voltage applied to the wiring resistance other than the device. The voltage at a luminance of 100 cd/m$^2$ was also read, while measuring the luminance using a luminance meter (spectroradiometer CS-1000 manufactured by Minolta) simultaneously with the measurement of the applied voltage.

(4) Triplet Energy

A sample was dissolved in EPA solvent (diethyl ether: isopentane ethanol=5:5:2 (by volume)) in a concentration of 10 mmol/L to prepare a specimen for phosphorescence measurement. The specimen for phosphorescence measurement was placed in a quartz cell and irradiated with excitation ray at 77 K, and the emitted phosphorescence was measured. Using the measured result, the triplet energy was determined as the value calculated from the following conversion formula:

$$E^T(eV) = 1239.85/\lambda_{edge}.$$

On the phosphorescence spectrum with a vertical axis of phosphorescent intensity and a horizontal axis of wavelength, a line tangent to the rising portion at the short-wavelength side of the phosphorescent spectrum was drawn, and the wavelength (nm) at the intersection of the tangent line and the horizontal axis was expressed by "$\lambda_{edge}$."

(5) Glass Transition Point

A sample of about 3 mg was heated and cooled according to the following 2-cycle heating/cooling process (1) to (6) using DSC 8500 manufactured by Perkin Elmer Inc.:

(1) keeping the sample at 30° C. for one minute;
(2) heating the sample from 30° C. to a given temperature lower than the thermal decomposition temperature of the sample at a temperature rising speed of 10° C./min;
(3) keeping the sample at the given temperature for 3 min;
(4) cooling the sample from the given temperature to 0° C. at a cooling speed of 200° C./min;
(5) keeping the sample at 0° C. for 10 min; and
(6) heating the sample from 0° C. to 200° C. at a temperature rising speed of 10° C./min.

The temperature of the inflection point where the base line of DSC curve in the temperature-rising step (6) changed stepwise was employed as the glass transition point.

Syntheses Example 1

Synthesis of Compound (1)

(1) Synthesis of Compound (1-a)

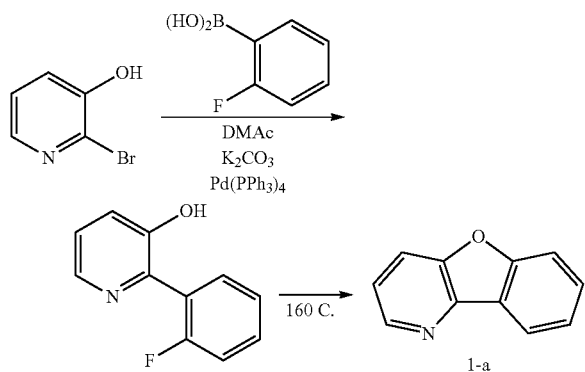

Into a three-necked flask, 100.1 g (575 mmol) of 2-bromo-3-hydroxypyridine, 88.5 g (632.5 mmol) of 2-fluorophenylboronic acid, 88.5 g (2300 mmol) of potassium carbonate, 1150 ml of N,N-dimethylacetamide, and 13.3 g (11.5 mmol) of Pd(PPh$_3$)$_4$ were charged. In nitrogen atmosphere, the mixture was stirred under heating at 90° C. for 12 h and further stirred under heating at 160° C. for 8 h.

After the reaction, the reaction solution was cooled to room temperature and then added with 1 L of toluene and 1 L of water. The resultant liquid was vigorously shaken in a separating funnel. After separating the toluene phase, the water phase was extracted by several portions of toluene. The obtained toluene solution was washed with water several times, dried over anhydrous magnesium sulfate, passed through a short column of silica gel, and then, concentrated. The obtained product was recrystallized from 200 ml of hexane, to obtain a pale yellow solid.

The identification of the compound was made by $^1$H-NMR. The yield was 54.4 g and the percentage yield was 56%.

(2) Synthesis of Compound (1-b)

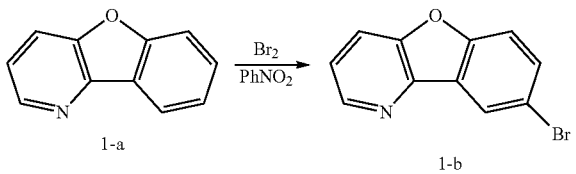

Into a three-necked flask, 52.6 g (310 mmol) of the compound 1-a, 155 ml of nitrobenzene, and 19.1 ml (372 mmol) of boron were charged. The mixture was stirred under heating at 140° C. for 12 h in the atmosphere.

After the reaction, the reaction solution was added with an aqueous solution of sodium thiosulfate under cooling in an iced water bath to deactivate the remaining boron, and then, added with an aqueous solution of sodium hydroxide to adjust the pH level of the aqueous phase to pH 10. The resultant solution was extracted with several portions of toluene in a separating funnel. The extract was dried over anhydrous magnesium sulfate, filtered, concentrated, and purified by silica gel chromatography (CH$_2$Cl$_2$:AcOEt=8:2). The purified product was dispersed in hexane for washing, collected by filtration, and vacuum-dried (40° C., 6 h) to obtain a pale yellow solid.

The identification of the compound was made by $^1$H-NMR. The yield was 32.1 g and the percentage yield was 42%.

(3) Synthesis of Compound (1)

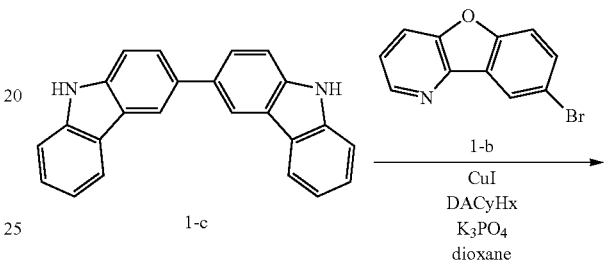

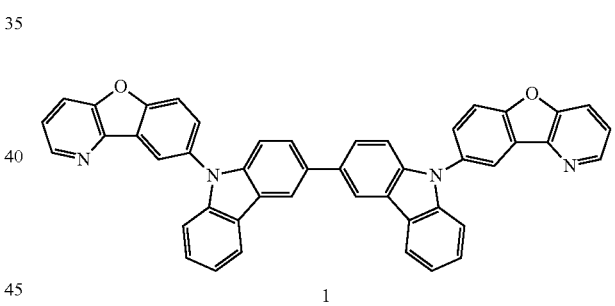

Into a three-necked flask, 6.65 g (20 mmol) of the compound 1-c, 10.92 g (44 mmol) of the compound 1-b, 16.98 g (80 mmol) of K$_3$PO$_4$, 3.81 g (20 mmol) of CuI, 7.2 ml (60 mmol) of trans-1,2-diaminocyclohexane, and 80 ml of 1,4-dioxane were charged. The mixture was refluxed for 24 h in nitrogen atmosphere.

After the reaction, the reaction solution was added with 80 ml of methanol and 80 ml of water, and then, ultrasonically washed for 10 min. The precipitate was collected by filtration, washed with methanol and water, and dried. The dried product was resolved in 1 of o-xylene under heating. Immediately after cooling to room temperature, the solution was passed through a silica gel short column to remove impurities and the eluted solution was concentrated. The concentrate was recrystallized three times from a mixed solvent of o-xylene:ethyl acetate=1:1 to obtain a white solid.

The identification of the compound was made by $^1$H-NMR and FD/MS molecular weight measurement. The yield was 4.5 g and the percentage yield was 34%. The measured triplet energy and glass transition point are shown in Table 2.

Syntheses Example 2

Synthesis of Compound (2)

(1) Synthesis of Compound (2-a)

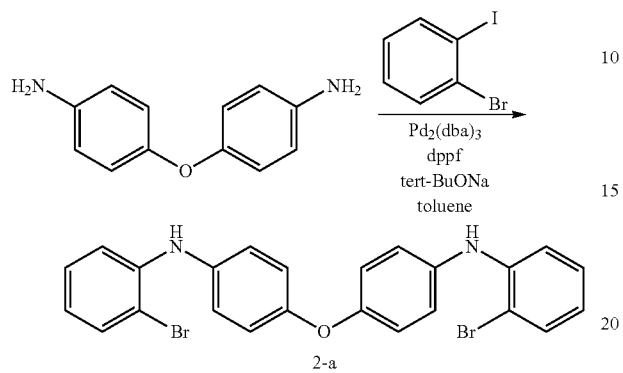

Into a three-necked flask, 48.1 g (240 mmol) of 4,4'-diaminodiphenyl ether, 149.4 g (528 mmol) of 2-bromoiodobenzene, 92.3 g (960 mmol) of tert-BuONa, 2.2 g (2.4 mmol) of $Pd_2(dba)_3$, 2.66 g (4.8 mmol) of 1,1'-bis(diphenylphosphino)ferrocene, and 960 ml of toluene were charged. The mixture was refluxed for 8 h in nitrogen atmosphere.

After the reaction, the reaction liquid was added with 500 ml of water and then extracted with several portions of ethyl acetate in a separating funnel. The extract was dried over anhydrous magnesium sulfate, filtered, and concentrated. The concentrate was purified by silica gel chromatography (toluene:hexane=3:7) to obtain a colorless viscous matter.

The identification of the compound was made by $^1$H-NMR and FD/MS molecular weight measurement. The yield was 109.68 g and the percentage yield was 90%.

(2) Synthesis of Compound (2-b)

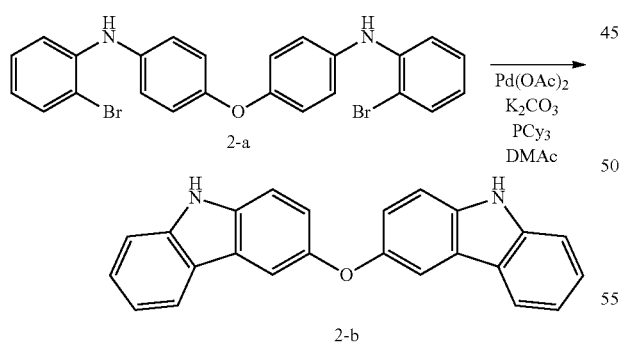

Into a three-necked flask, 28.01 g (54.9 mmol) of the compound 2-a, 2.47 g (10.98 mmol) of palladium acetate, 30.35 g (mmol) of potassium carbonate, 274 ml of N,N-dimethylacetamide, and 30.8 ml (21.96 mmol) of tricyclohexylphosphine (20 wt % toluene solution) were charged. The mixture was stirred under heating at 150° C. for 8 h in nitrogen atmosphere.

After the reaction, the inorganic salts were removed from the reaction liquid by filtration through Celite. The filtrate was poured into 1 L of water and the precipitated matter was collected by filtration. The collected matter was dispersed in a mixed solvent of methanol:ethyl acetate=200 ml:200 ml for washing, collected by filtration, and vacuum-dried (60° C., 4 h) to obtain a white solid.

The identification of the compound was made by $^1$H-NMR and FD/MS molecular weight measurement. The yield was 13.63 g and the percentage yield was 71%.

(3) Synthesis of Compound (2)

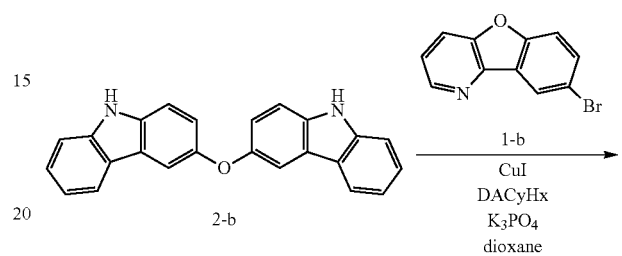

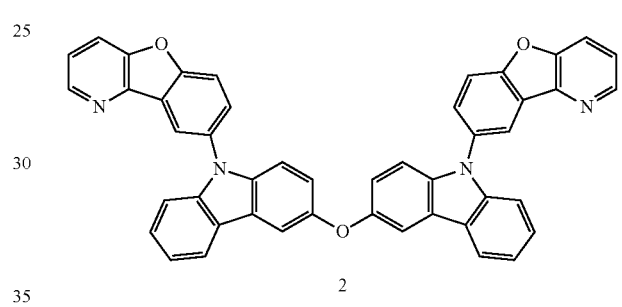

The compound (2) was synthesized in the same manner as in Synthesis Example 1-(3) (Synthesis of Compound (1)) except for using the compound 2-b in place of the compound 1-c. The measured triplet energy is shown in Table 2.

Synthesis Example 3

Synthesis of Compound (3)

(1) Synthesis of Compound (3-a)

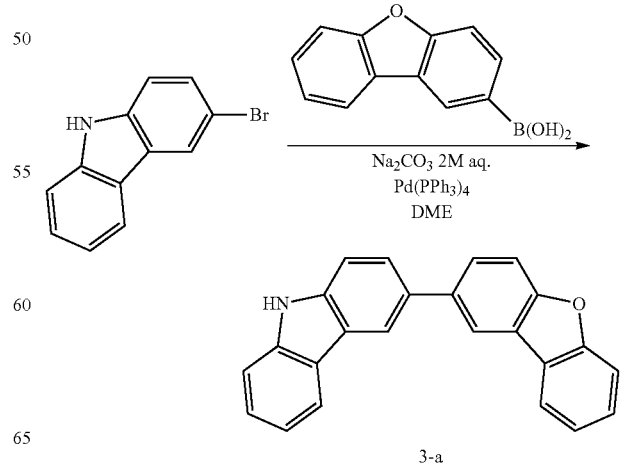

Into a three-necked flask, 12.31 g (50 mmol) of 3-bromocarbazole, 11.66 g (55 mmol) of 2-dibenzofuranboronic acid, 50 ml of a 2 M aqueous solution of sodium carbonate, 50 ml of 1,2-dimethoxyethane, and 1.16 g (1.0 mmol) of Pd(PPh$_3$)$_4$ were charged. The mixture was refluxed for 12 h in nitrogen atmosphere.

After the reaction, the reaction liquid was extracted with several portions of dichloromethane in a separating funnel. The extract was dried over anhydrous magnesium sulfate, filtered, and concentrated. The concentrate was dispersed in a mixed solvent of ethyl acetate:methanol=1:2 for washing to obtain a white solid.

The yield was 16.27 g and the percentage yield was 65%.

(2) Synthesis of Compound (3)

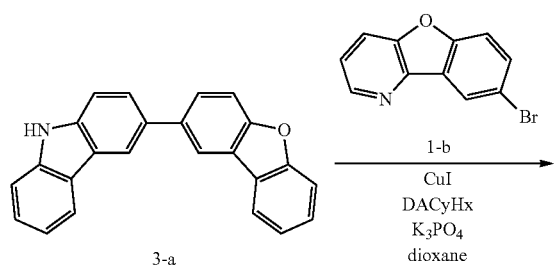

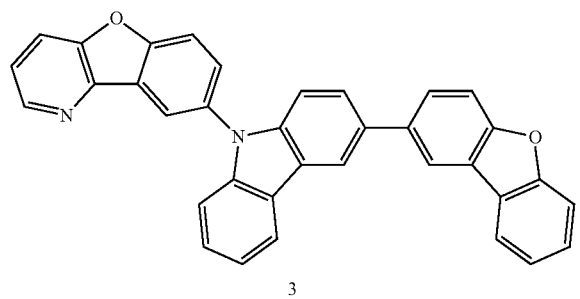

The compound (3) was synthesized in the same manner as in Synthesis Example 1-(3) (Synthesis of Compound (1)) except for using the compound 3-a in place of the compound 1-c. The measured triplet energy is shown in Table 2.

Synthesis Example 4

Synthesis of Compound (4)

(1) Synthesis of Compound (4-a)

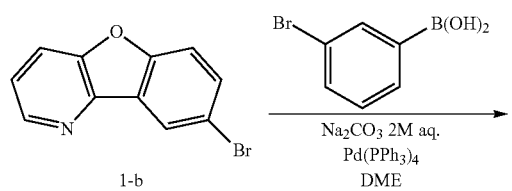

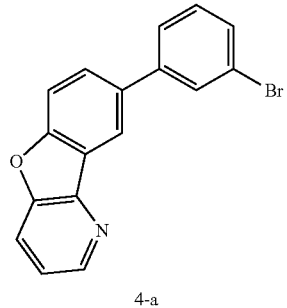

Into a three-necked flask, 12.40 g (50 mmol) of the compound 1-b, 12.04 g (60 mmol) of 3-bromophenylboronic acid, 50 ml of a 2 M aqueous solution of sodium carbonate, 50 ml of 1,2-dimethoxyethane, and 1.16 g (1.0 mmol) of Pd(PPh$_3$)$_4$ were charged. The mixture was refluxed for 12 h in nitrogen atmosphere.

After the reaction, the reaction liquid was extracted with several portions of dichloromethane in a separating funnel. The extract was dried over anhydrous magnesium sulfate, filtered, and concentrated. The concentrate was purified by silica gel chromatography (dichloromethane:ethyl acetate=9:1) to obtain a colorless viscous matter.

The yield was 5.02 g and the percentage yield was 31%.

(2) Synthesis of Compound (4)

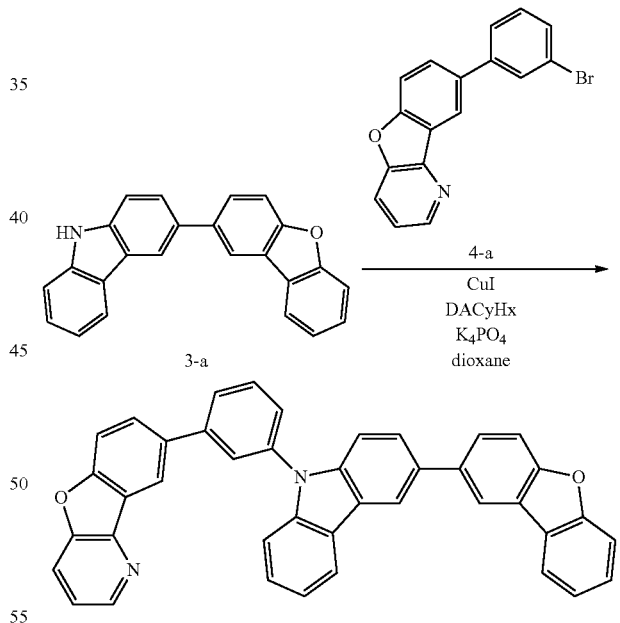

The compound (4) was synthesized in the same manner as in Synthesis Example 1-(3) (Synthesis of Compound (1)) except for using the compound 3-a in place of the compound 1-c and using the compound 4-a in place of the compound 1-b. The measured triplet energy is shown in Table 2.

Synthesis example 5 to 10

In the same manner as in Synthesis Examples 1 to 4, the compounds (5) to (10) mentioned below were synthesized by a coupling reaction or a cyclization reaction each using a palladium catalyst or a copper catalyst, or by an organic synthesizing reaction known in the art.

Example 1

A glass substrate having an ITO transparent electrode line with a thickness of 130 nm (manufactured by Geomatec Company) was cleaned by ultrasonic cleaning in isopropyl alcohol for 5 min and then UV ozone cleaning for 30 min.

The cleaned glass substrate having an ITO electrode line was mounted to a substrate holder of a vacuum vapor deposition apparatus. The compound (HI1) was vapor-deposited by resistance heating into a thickness of 20 nm so as to cover the ITO electrode line, and then, the compound (HT1) was vapor-deposited by resistance heating into a thickness of 60 nm, thereby successively forming thin film layers. The film-forming rate was 1 Å/s. These thin films work as a hole injecting layer and a hole transporting layer, respectively.

On the hole injecting/transporting layer, the compound (H1) and the compound (BD1) were co-deposited by resistance heating to form a thin film with a thickness of 50 nm. The deposited amount of the compound (BD1) was 20% by mass of the total mass of the compound (H1) and the compound (BD1). The film-forming rates were 1.2 Å/s and 0.3 Å/s, respectively. The obtained thin film works as a phosphorescent emitting layer. The triplet energy of the compound (BD1) is shown in Table 2.

Next, on the phosphorescent emitting layer, the compound (1) was vapor-deposited by resistance heating to form a thin film with a thickness of 10 nm. The film-forming rate was 1.2 Å/s. The obtained thin film works as a blocking layer.

Next, on the blocking layer, the compound (ET1) was vapor-deposited by resistance heating to form a thin film with a thickness of 10 nm. The film-forming rate was 1 Å/s. The obtained thin film works as an electron injecting layer.

Next, LiF was vapor-deposited on the electron injecting layer to form a LiF film with a thickness of 1.0 nm at a film-forming rate of 0.1 Å/s.

Then, metallic Al was vapor-deposited on the LiF film at a film-forming rate of 8.0 Å/s to form a metallic cathode with a thickness of 80 nm, thereby obtaining an organic EL device.

Examples 2 To 4 and Comparative Example 1

Each organic EL device was produced in the same manner as in Example 1 except for using the compound listed in Table 1 in place of the compound (1).

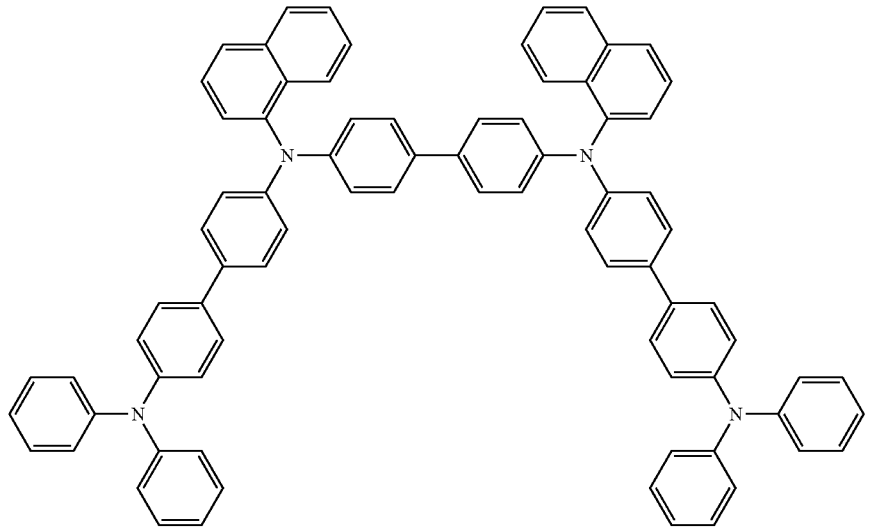

Compound (H11)

-continued
Compound (HT1)
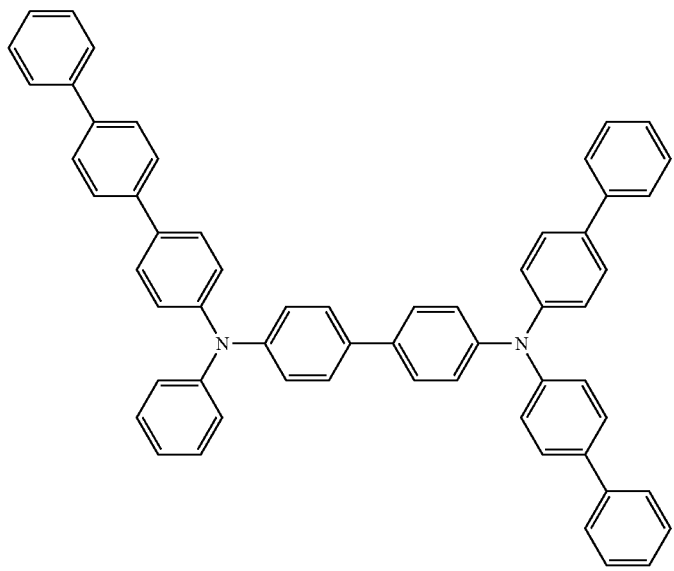
Compound (H1)
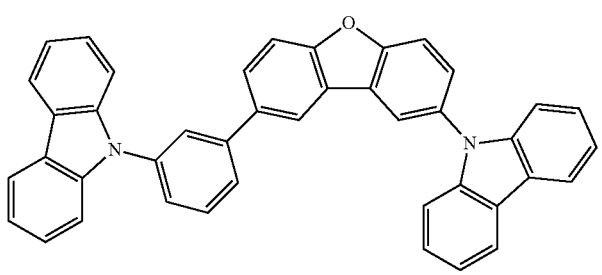
Compound (BD1)
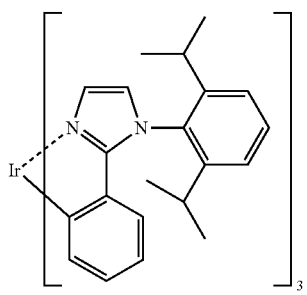
Compound (ET1)
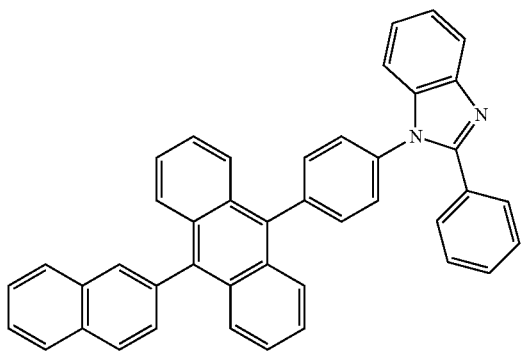

-continued
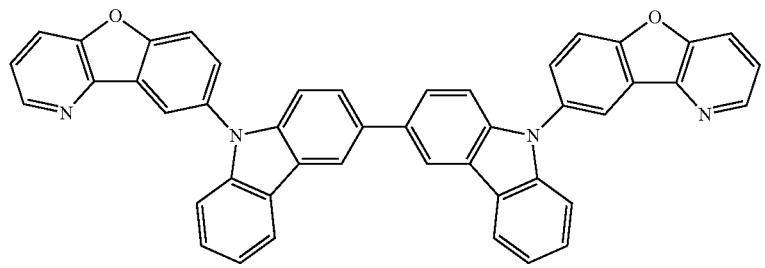
Compound (1)
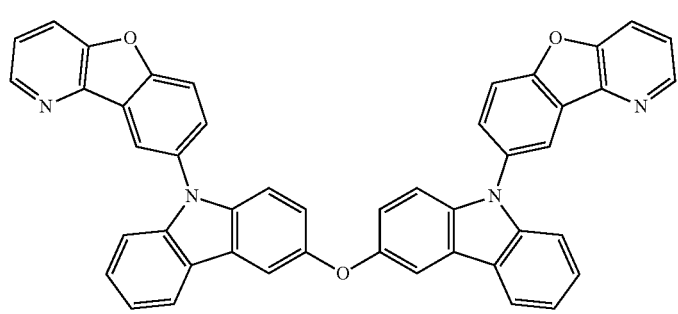
Compound (2)
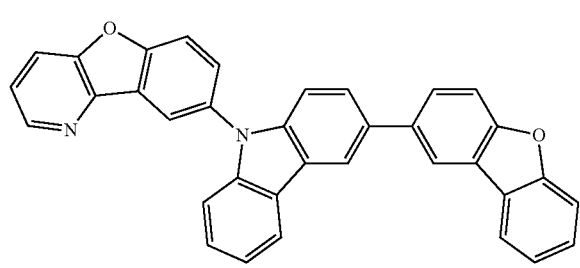
Compound (3)
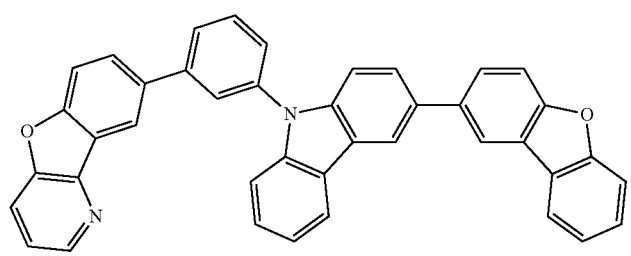
Compound (4)

TABLE 1

| | Blocking layer | Voltage (V) | External quantum efficiency (%) | Half lifetime (h) |
|---|---|---|---|---|
| Examples | | | | |
| 1 | Compound (1) | 3.2 | 18.5 | 4800 |
| 2 | Compound (2) | 3.4 | 18.0 | 4200 |
| 3 | Compound (3) | 3.3 | 18.3 | 5300 |
| 4 | Compound (4) | 3.5 | 17.5 | 5200 |
| Comparative Example | | | | |
| 1 | Compound (H1) | 5.7 | 14.3 | 5000 |

TABLE 2

| Compounds | Triplet energy (eV) | Glass transition point (° C.) |
|---|---|---|
| Compound (1) | 2.94 | 162 |
| Compound (2) | 2.97 | 149 |
| Compound (3) | 2.95 | 111 |
| Compound (4) | 2.95 | 118 |
| Compound (H1) | 3.03 | 126 |
| Compound (BD1) | 2.64 | — |

As seen from Table 1, the compounds (1) to (4) of the invention provided organic EL devices with long lifetimes, which could be driven at lower voltage in higher efficiency, as compared with the organic EL device employing the comparative compound.

In addition, the organic EL devices of the invention exhibited high efficiencies, because the triplet energy of the compound (1) to (4) forming the blocking layer and the triplet energy of the compound (BD 1) used as the phosphorescent dopant satisfied the following relationship:

$$0.2 eV < \Delta E^T = E^T_{TB} - E^T_d.$$

Examples 5 to 10 and Comparative Examples 2 to 3

Each organic EL device was produced in the same manner as in Example 1 except for using the compound listed in Table 3 in place of the compound (1).

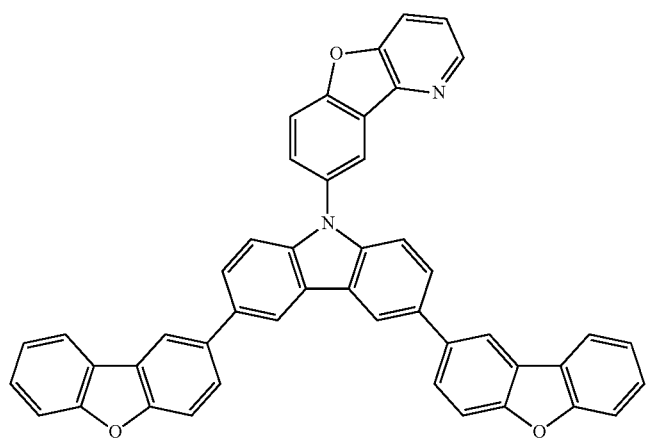

Compound (5)

-continued
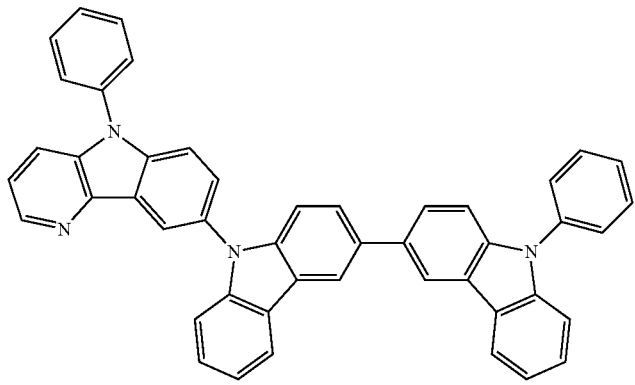
Compound (6)
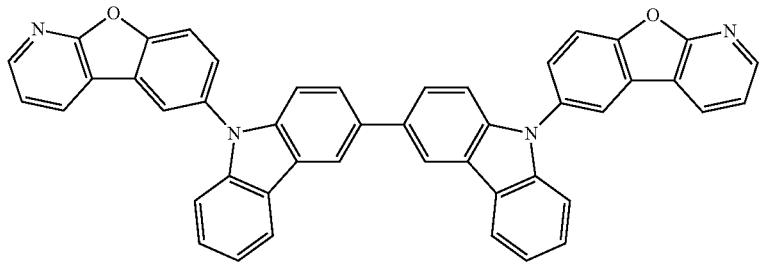
Compound (7)
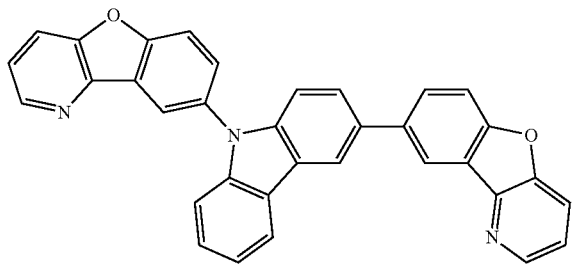
Compound (8)
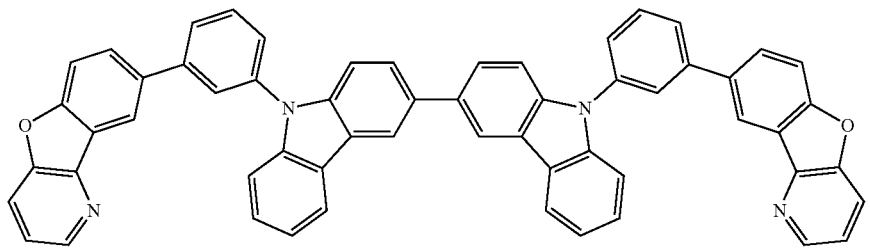
Compound (9)
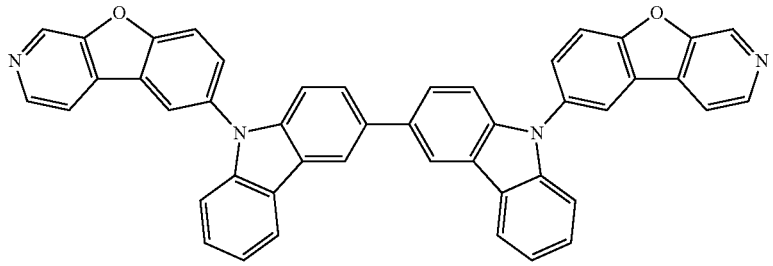
Compound (10)
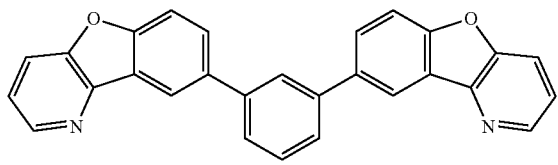
Compound (H2)

-continued

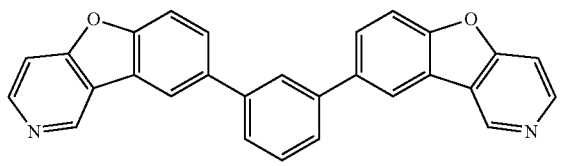

Compound (H3)

TABLE 3

| | Blocking layer | Voltage (V) | External quantum efficiency (%) | Half lifetime (h) |
| --- | --- | --- | --- | --- |
| Examples | | | | |
| 5 | Compound (5) | 4.1 | 16.7 | 4700 |
| 6 | Compound (6) | 4.6 | 16.4 | 5000 |
| 7 | Compound (7) | 5.3 | 16.2 | 4800 |
| 8 | Compound (8) | 4.2 | 15.8 | 4000 |
| 9 | Compound (9) | 4.1 | 18.9 | 4900 |
| 10 | Compound (10) | 4.8 | 15.8 | 3400 |
| Comparative Examples | | | | |
| 2 | Compound (H2) | 4.4 | 18.0 | 2500 |
| 3 | Compound (H3) | 5.0 | 15.3 | 200 |

TABLE 4

| Compounds | Triplet energy (eV) | Glass transition point (° C.) |
| --- | --- | --- |
| Compound (5) | 2.97 | 149 |
| Compound (6) | 2.92 | 150 |
| Compound (7) | 2.88 | — |
| Compound (8) | 2.95 | 121 |
| Compound (9) | 2.92 | 159 |
| Compound (10) | 2.91 | 171 |
| Compound (H2) | 3.03 | 71 |
| Compound (H3) | 3.04 | not detected |

As seen from Tables 2 and 4, the compound of formula (1) wherein G14 among G11 to G14 represents a nitrogen atom has the highest triplet energy and is effective for improving the efficiency.

As seen from Tables 1 and 2, the compound of formula (1) wherein G14 among G11 to G14 represents a nitrogen atom is most effective for reducing the driving voltage and improving the lifetime.

As seen from Table 2, the compound (2) wherein $L_2$ represents an oxygen-containing divalent linking group has a triplet energy higher than that of the compound (1) wherein $L_2$ represents a single bond.

INDUSTRIAL APPLICABILITY

As described above in detail, the material for organic EL device of the invention provides an organic EL device having a high emission efficiency and a long lifetime. Therefore the organic EL device is extremely useful as displays and light sources of various types of electronic equipments.

What is claimed is:

1. A compound represented by formula (1):

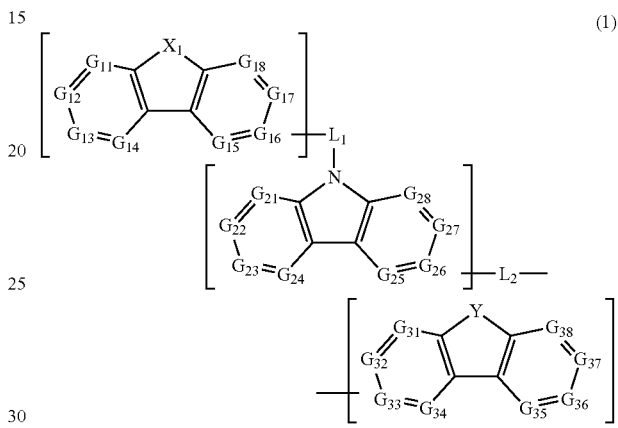

wherein:
at least one of $G_{11}$ to $G_{18}$ represents a nitrogen atom, another of $G_{11}$ to $G_{18}$ represents a carbon atom bonded to $L_1$, and the other or others of $G_{11}$ to $G_{18}$ represent $C(R_1)$;
one of $G_{21}$ to $G_{28}$ represents a carbon atom bonded to $L_2$ and the others represent $C(R_2)$ or a nitrogen atom;
one of $G_{31}$ to $G_{38}$ represents a carbon atom bonded to $L_2$ and the others represent $C(R_3)$ or a nitrogen atom;
each $R_1$ independently represents a hydrogen atom, a substituted or unsubstituted alkyl group comprising 1 to 20 carbon atoms, a substituted or unsubstituted cycloalkyl group comprising 3 to 20 ring carbon atoms, a substituted or unsubstituted cycloalkoxy group comprising 3 to 20 ring carbon atoms, a substituted or unsubstituted alkoxy group comprising 1 to 20 carbon atoms, a substituted or unsubstituted aryl group comprising 6 to 18 ring carbon atoms, a substituted or unsubstituted heteroaryl group comprising 5 to 18 ring atoms, a substituted or unsubstituted aryloxy group comprising 6 to 18 ring carbon atoms, a substituted or unsubstituted amino group comprising 0 to 20 carbon atoms, a substituted or unsubstituted silyl group comprising 0 to 30 carbon atoms, a fluorine atom, or a cyano group;
each $R_2$ independently represents a hydrogen atom, a substituted or unsubstituted alkyl group comprising 1 to 20 carbon atoms, a substituted or unsubstituted cycloalkyl group comprising 3 to 20 ring carbon atoms, a substituted or unsubstituted cycloalkoxy group comprising 3 to 20 ring carbon atoms, a substituted or unsubstituted alkoxy group comprising 1 to 20 carbon atoms, a substituted or unsubstituted aryl group comprising 6 to 18 ring carbon atoms, a substituted or unsubstituted heteroaryl group, wherein the heteroaryl group is selected from the group consisting of a carbolinyl group, a dibenzofuranyl group, a dibenzothiophenyl group, a pyrrolyl group, a furyl group, a thienyl group, a silolyl group, a pyridyl group, a quinolyl group, an isoquinolyl group, an indolyl group, a benzofuryl group, a benzothiophenyl group, an imidazolyl group, a benzimidazolyl group, a pyrimidyl group, a selenophenyl group, an oxadiazolyl group, a triazolyl group, an azaphenanthryl group, and a phenanthrolinyl group, a substituted or unsubstituted aryloxy group comprising 6 to 18 ring carbon atoms, a substituted or unsubstituted amino group comprising 0 to 20 carbon atoms, a substituted or unsubstituted silyl group comprising 0 to 30 carbon atoms, a fluorine atom, or a cyano group;

$R_1$ groups and $R_2$ groups may be the same or different;

each $R_3$ represents a hydrogen atom;

each optional substituent of $R_1$ and $R_2$ is independently an alkyl group comprising 1 to 20 carbon atoms, a cycloalkyl group comprising 3 to 20 ring carbon atoms, an alkoxy group comprising 1 to 20 carbon atoms, a cycloalkoxy group comprising 3 to 20 ring carbon atoms, an aryl group comprising 6 to 18 ring carbon atoms, a heteroaryl group comprising 5 to 18 ring atoms, an aryloxy group comprising 6 to 18 ring carbon atoms, an amino group comprising 0 to 20 carbon atoms, a silyl group comprising 0 to 30 carbon atoms, a fluorine atom, or a cyano group;

$X_1$ represents an oxygen atom, a sulfur atom, or —N($R_4$)—;

$R_4$ represents a hydrogen atom, an alkyl group comprising 1 to 20 carbon atoms, a cycloalkyl group comprising 3 to 20 ring carbon atoms, an aryl group comprising 6 to 18 ring carbon atoms, or a heteroaryl group comprising 5 to 18 ring atoms;

$L_1$ represents a single bond, an alkylene group comprising 1 to 20 carbon atoms, a cycloalkylene group comprising 3 to 20 ring carbon atoms, an arylene group comprising 6 to 18 ring carbon atoms, or a heteroarylene group comprising 5 to 18 ring atoms, provided that divalent residues of dibenzofuran and dibenzothiophene are excluded;

$L_2$ represents a single bond, an alkylene group comprising 1 to 20 carbon atoms, a cycloalkylene group comprising 3 to 20 ring carbon atoms, an arylene group comprising 6 to 18 ring carbon atoms, a heteroarylene group selected from the group consisting of residues obtained by removing one hydrogen atom from a carbolinyl group, a dibenzofuranyl group, a dibenzothiophenyl group, a pyrrolyl group, a furyl group, a thienyl group, a silolyl group, a pyridyl group, a quinolyl group, an isoquinolyl group, an indolyl group, a benzofuryl group, a benzothiophenyl group, an imidazolyl group, a benzimidazolyl group, a pyrimidyl group, a selenophenyl group, an oxadiazolyl group, a triazolyl group, an azaphenanthryl group, and a phenanthrolinyl group, an oxygen-comprising divalent linking group, a silicon-comprising divalent linking group, a phosphorous-comprising divalent linking group, or a sulfur-comprising divalent linking group;

Y represents an oxygen atom, a sulfur atom, or —N(-$L_3$-$R_5$)—, wherein Y represents an oxygen atom or a sulfur atom when $L_2$ represents a single bond;

$L_3$ represents a single bond, an alkylene group comprising 1 to 20 carbon atoms, a cycloalkylene group comprising 3 to 20 ring carbon atoms, an arylene group comprising 6 to 18 ring carbon atoms, or a heteroarylene group comprising 5 to 18 ring atoms; and $R_5$ represents a hydrogen atom, an alkyl group comprising 1 to 20 carbon atoms, a cycloalkyl group comprising 3 to 20 ring carbon atoms, an aryl group comprising 6 to 18 ring carbon atoms, or a heteroaryl group comprising 5 to 18 ring atoms;

provided that when $X_1$ represents an oxygen atom or a sulfur atom, only one of $G_{11}$ to $G_{18}$ represents a nitrogen atom, and when $X_1$ represents —N($R_4$)—, Y represents —N(-$L_3$-$R_5$)— and simultaneously each of $R_2$ and $R_3$ represents a hydrogen atom.

2. The compound of claim 1, wherein $G_{14}$ of formula (1) represents a nitrogen atom.

3. The compound of claim 1, wherein $X_1$ of formula (1) represents an oxygen atom or a sulfur atom.

4. The compound of claim 1, wherein:

Y of formula (1) represents —N(-$L_3$-$R_5$)—; and $R_5$ represents a heteroaryl group represented by formula (A):

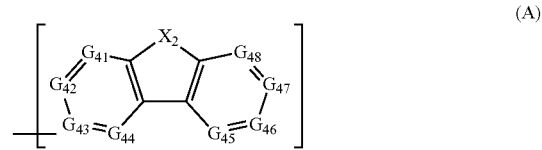

wherein:

one of $G_{41}$ to $G_{48}$ represents a carbon adorn bonded to $L_3$ and the others represent a nitrogen atom or C($R_6$);

$R_6$ represents a hydrogen atom, a substituted or unsubstituted alkyl group comprising 1 to 20 carbon atoms, a substituted or unsubstituted cycloalkyl group comprising 3 to 20 ring carbon atoms, a substituted or unsubstituted alkoxy group comprising 1 to 20 carbon atoms, a substituted or unsubstituted cycloalkoxy group comprising 3 to 20 ring carbon atoms, a substituted or unsubstituted aryl group comprising 6 to 18 ring carbon atoms, a substituted or unsubstituted heteroaryl group comprising 5 to 18 ring atoms, a substituted or unsubstituted aryloxy group comprising 6 to 18 ring carbon atoms, a substituted or unsubstituted amino group comprising 0 to 20 carbon atoms, a substituted or unsubstituted silyl group comprising 0 to 30 carbon atoms, a fluorine atom, or a cyano group, provided that $R_6$ groups may be the same or different;

each optional substituent of $R_6$ is independently an alkyl group comprising 1 to 20 carbon atoms, a cycloalkyl group comprising 3 to 20 ring carbon atoms, an alkoxy group comprising 1 to 20 carbon atoms, a cycloalkoxy group comprising 3 to 20 ring carbon atoms, an aryl group comprising 6 to 18 ring carbon atoms, a heteroaryl group comprising 5 to 18 ring atoms, an aryloxy group comprising 6 to 18 ring carbon atoms, an amino group comprising 0 to 20 carbon atoms, a silyl group comprising 0 to 30 carbon atoms, a fluorine atom, or a cyano group;

$X_2$ represents an oxygen atom, a sulfur atom, or —N($R_7$)—; and $R_7$ represents a hydrogen atom, an alkyl group comprising 1 to 20 carbon atoms, a cycloalkyl group comprising 3 to 20 ring carbon atoms, an aryl group comprising 6 to 18 ring carbon atoms, or a heteroaryl group comprising 5 to 18 ring atoms.

5. The compound of claim 1, wherein Y of formula (1) represents an oxygen atom or a sulfur atom.

6. The compound of claim 1, wherein $G_{16}$ of formula (1) represents a carbon atom bonded to $L_1$.

7. The compound of claim 1, wherein $L_1$ of formula (1) represents a single bond, an arylene group comprising 6 to 18 ring carbon atoms, or a heteroarylene group comprising 5 to 18 ring atoms, provided that divalent residues of dibenzofuran and dibenzothiophene are excluded.

8. The compound of claim 7, wherein $L_1$ represents an arylene group comprising 6 to 18 ring carbon atoms or a heteroarylene group comprising 5 to 18 ring atoms, provided that divalent residues of dibenzofuran and dibenzothiophene are excluded.

9. The compound of claim 8, wherein $L_1$ represents a phenylene group.

10. The compound of claim 1, wherein $L_2$ of formula (1) represents an alkylene group comprising 1 to 20 carbon atoms, a cycloalkylene group comprising 3 to 20 ring carbon atoms, an oxygen-comprising divalent linking group, a silicon-comprising divalent linking group, a phosphorous-comprising divalent linking group, or a sulfur-comprising divalent linking group.

11. The compound of claim 1, wherein $X_1$ of formula (1) represents —N($R_4$)—.

12. The compound of claim 1, wherein each of $G_{26}$ and $G_{33}$ of formula (1) represents a carbon atom bonded to $L_2$.

13. The compound of claim 4, wherein at least one of $G_{31}$ to $G_{38}$ and $G_{41}$ to $G_{48}$ of formula (1) represents a nitrogen atom.

14. The compound of claim 1, which is represented by formula (2):

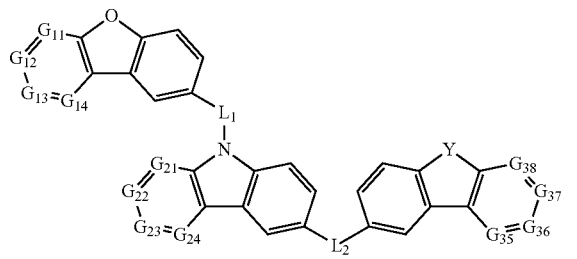

(2)

wherein:
one of $G_{11}$ to $G_{14}$ represents a nitrogen atom and the others represent $C(R_1)$;
each of $G_{21}$ to $G_{24}$ represents $C(R_2)$ or a nitrogen atom;
each of $G_{35}$ to $G_{38}$ represents $C(R_3)$ or a nitrogen atom;
each $R_1$ independently represents a hydrogen atom, an alkyl group comprising 1 to 20 carbon atoms, a cycloalkyl group comprising 3 to 20 ring carbon atoms, an aryl group comprising 6 to 18 ring carbon atoms, or a heteroaryl group comprising 5 to 18 ring atoms;
each $R_2$ independently represents a hydrogen atom, an alkyl group comprising 1 to 20 carbon atoms, a cycloalkyl group comprising 3 to 20 ring carbon atoms, an aryl group comprising 6 to 18 ring carbon atoms, or a heteroaryl group selected from the group consisting of a carbolinyl group, a dibenzofuranyl, group, a dibenzothiophenyl group, a pyrrolyl group, a furyl group, a thienyl group, a silolyl group, a pyridyl group, a quinolyl group, an isoquinolyl group, an indolyl group, a benzofuryl group, a benzothiophenyl group, an imidazolyl group, a benzimidazolyl group, a pyrimidyl group, a selenophenyl group, an oxadiazolyl group, a triazolyl group, an azaphenanthryl group, and a phenanthrolinyl group;
each $R_3$ represents a hydrogen atom;
$L_1$ represents a single bond, an arylene group comprising 6 to 18 ring carbon atoms, or a heteroarylene group comprising 5 to 18 ring atoms, provided that divalent residues of dibenzofuran and dibenzothiophene are excluded;
$L_2$ represents a single bond, an arylene group comprising 6 to 18 ring carbon atoms, a heteroarylene group selected from the group consisting of residues obtained by removing one hydrogen atom from a carbolinyl group, a dibenzofuranyl group, a dibenzothiophenyl group, a pyrrolyl group, a furyl group, a thienyl group, a silolyl group, a pyridyl group, a quinolyl group, an isoquinolyl group, an indolyl group, a benzofuryl group, a benzothiophenyl group, an imidazolyl group, a benzimidazolyl group, a pyrimidyl group, a selenophenyl group, an oxadiazolyl group, a triazolyl group, an azaphenanthryl group, and a phenanthrolinyl group, an oxygen-comprising divalent linking group, a silicon-comprising divalent linking group, a phosphorous-comprising divalent linking group, or a sulfur-comprising divalent linking group;
Y represents an oxygen atom, a sulfur atom, or —N(-$L_3$-$R_5$)—, wherein Y represents an oxygen atom or a sulfur atom when $L_2$ represents a single bond;
$L_3$ represents a single bond, an arylene group comprising 6 to 18 ring carbon atoms, or a heteroarylene group comprising 5 to 18 ring atoms; and
$R_5$ represents a hydrogen atom, an alkyl group comprising 1 to 20 carbon atoms, a cycloalkyl group comprising 3 to 20 ring carbon atoms, an aryl group comprising 6 to 18 ring carbon atoms, or a heteroaryl group comprising 5 to 18 ring atoms.

15. An organic electroluminescence device, comprising:
a cathode;
an anode; and
an organic thin film layer comprising one or more layers between the cathode and the anode;
wherein:
the organic thin film layer comprises a light emitting layer comprising a phosphorescent emitting material; and
at least one layer of the organic thin film layer comprises the compound of claim 1.

16. The compound of claim 1, wherein at least one of $G_{11}$ to $G_{14}$ represents a nitrogen atom, one of $G_{15}$ to $G_{18}$ represents a carbon atom bonded to $L_1$, and the others of $G_{11}$ to $G_{18}$ represent $C(R_1)$.

17. A compound represented by formula (1):

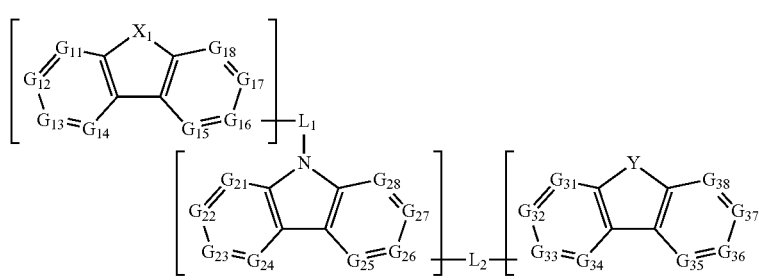

wherein:
at least one of $G_{11}$ to $G_{18}$ represents a nitrogen atom, another of $G_{11}$ to $G_{18}$ represents a carbon atom bonded to $L_1$, and the other or others of $G_{11}$ to $G_{18}$ represent $C(R_1)$;
one of $G_{21}$ to $G_{28}$ represents a carbon atom bonded to $L_2$ and the others represent $C(R_2)$ or a nitrogen atom;
one of $G_{31}$ to $G_{38}$ represents a carbon atom bonded to $L_2$ and the others represent $C(R_3)$ or a nitrogen atom;
each of $R_1$ and $R_3$ independently represents a hydrogen atom, a substituted or unsubstituted alkyl group comprising 1 to 20 carbon atoms, a substituted or unsubstituted cycloalkyl group comprising 3 to 20 ring carbon atoms, a substituted or unsubstituted cycloalkoxy group comprising 3 to 20 ring carbon atoms, a substituted or unsubstituted alkoxy group comprising 1 to 20 carbon atoms, a substituted or unsubstituted aryl group comprising 6 to 18 ring carbon atoms, a substituted or unsubstituted heteroaryl group comprising 5 to 18 ring atoms, a substituted or unsubstituted aryloxy group comprising 6 to 18 ring carbon atoms, a substituted or unsubstituted amino group comprising 0 to 20 carbon atoms, a substituted or unsubstituted silyl group comprising 0 to 30 carbon atoms, a fluorine atom, or a cyano group;
each $R_2$ independently represents a hydrogen atom, a substituted or unsubstituted alkyl group comprising 1 to 20 carbon atoms, a substituted or unsubstituted cycloalkyl group comprising 3 to 20 ring carbon atoms, a substituted or unsubstituted cycloalkoxy group comprising 3 to 20 ring carbon atoms, a substituted or unsubstituted alkoxy group comprising 1 to 20 carbon atoms, a substituted or unsubstituted aryl group comprising 6 to 18 ring carbon atoms, a substituted or unsubstituted heteroaryl group, wherein the heteroaryl group is selected from the group consisting of a carbolinyl group, a dibenzofuranyl group, a dibenzothiophenyl group, a pyrrolyl group, a furyl group, a thienyl group, a silolyl group, a pyridyl group, a quinolyl group, an isoquinolyl group, an indolyl group, a benzofuryl group, a benzothiophenyl group, an imidazolyl group, a benzimidazolyl group, a pyrimidyl group, a selenophenyl group, an oxadiazolyl group, a triazolyl group, an azaphenanthryl group, and a phenanthrolinyl group, a substituted or unsubstituted aryloxy group comprising 6 to 18 ring carbon atoms, a substituted or unsubstituted amino group comprising 0 to 20 carbon atoms, a substituted or unsubstituted silyl group comprising 0 to 30 carbon atoms, a fluorine atom, or a cyano group;

$R_1$ groups, $R_2$ groups, and $R_3$ groups may be the same or different;
at least one $R_2$ represents a substituted or unsubstituted dibenzofuranyl group, or a substituted or unsubstituted dibenzothiophenyl group;
each optional substituent of $R_1$ to $R_3$ is independently an alkyl group comprising 1 to 20 carbon atoms, a cycloalkyl group comprising 3 to 20 ring carbon atoms, an alkoxy group comprising 1 to 20 carbon atoms, a cycloalkoxy group comprising 3 to 20 ring carbon atoms, an aryl group comprising 6 to 18 ring carbon atoms, a heteroaryl group comprising 5 to 18 ring atoms, an aryloxy group comprising 6 to 18 ring carbon atoms, an amino group comprising 0 to 20 carbon atoms, a silyl group comprising 0 to 30 carbon atoms, a fluorine atom, or a cyano group;
$X_1$ represents an oxygen atom, a sulfur atom, or —$N(R_4)$—;
$R_4$ represents a hydrogen atom, an alkyl group comprising 1 to 20 carbon atoms, a cycloalkyl group comprising 3 to 20 ring carbon atoms, an aryl group comprising 6 to 18 ring carbon atoms, or a heteroaryl group comprising 5 to 18 ring atoms;
$L_1$ represents a single bond, an alkylene group comprising 1 to 20 carbon atoms, a cycloalkylene group comprising 3 to 20 ring carbon atoms, an arylene group comprising 6 to 18 ring carbon atoms, or a heteroarylene group comprising 5 to 18 ring atoms, provided that divalent residues of dibenzofuran and dibenzothiophene are excluded;
$L_2$ represents a single bond, an alkylene group comprising 1 to 20 carbon atoms, a cycloalkylene group comprising 3 to 20 ring carbon atoms, an arylene group comprising 6 to 18 ring carbon atoms, a heteroarylene group selected from the group consisting of residues obtained by removing one hydrogen atom from a carbolinyl group, a dibenzofuranyl group, a dibenzothiophenyl group, a pyrrolyl group, a furyl group, a thienyl group, a silolyl group, a pyridyl group, a quinolyl group, an isoquinolyl group, an indolyl group, a benzofuryl group, a benzothiophenyl group, an imidazolyl group, a benzimidazolyl group, a pyrimidyl group, a selenophenyl group, an oxadiazolyl group, a triazolyl group, an azaphenanthryl group, and a phenanthrolinyl group, an oxygen-comprising divalent linking group, a silicon-comprising divalent linking group, a phosphorus-comprising divalent linking group, or a sulfur-comprising divalent linking group;
Y represents an oxygen atom, a sulfur atom, or —$N(-L_3-R_5)$—, wherein Y represents an oxygen atom or a sulfur atom when $L_2$ represents a single bond;

$L_3$ represents a single bond, an alkylene group comprising 1 to 20 carbon atoms, a cycloalkylene group comprising 3 to 20 ring carbon atoms, an arylene group comprising 6 to 18 ring carbon atoms, or a heteroarylene group comprising 5 to 18 ring atoms; and $R_5$ represents a hydrogen atom, an alkyl group comprising 1 to 20 carbon atoms, a cycloalkyl group comprising 3 to 20 ring carbon atoms, an aryl group comprising 6 to 18 ring carbon atoms, or a heteroaryl group comprising 5 to 18 ring atoms;

provided that when $X_1$ represents an oxygen atom or a sulfur atom, only one of $G_{11}$ to $G_{18}$ represents a nitrogen atom, and when $X_1$ represents —N($R_4$)—, Y represents —N(-$L_3$-$R_5$)—and simultaneously each of $R_2$ and $R_3$ represents a hydrogen atom.

18. The compound of claim 17, wherein $G_{14}$ of formula (1) represents a nitrogen atom.

19. The compound of claim 17, wherein $X_1$ of formula (1) represents an oxygen atom or a sulfur atom.

20. The compound of claim 17, wherein Y of formula (1) represents an oxygen atom or a sulfur atom.

21. The compound of claim 17, wherein $G_{16}$ of formula (1) represents a carbon atom bonded to $L_1$.

22. The compound of claim 17, wherein each of $G_{26}$ and $G_{33}$ of formula (1) represents a carbon atom bonded to $L_2$.

23. The compound of claim 17, which is represented by formula (2):

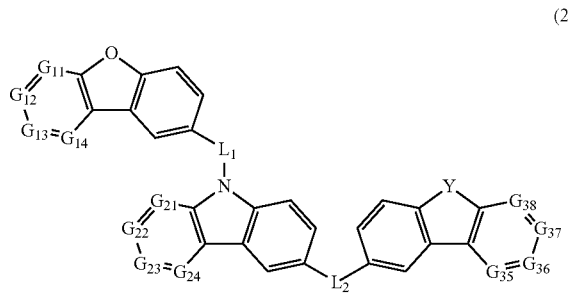

(2)

wherein:

one of $G_{11}$ to $G_{14}$ represents a nitrogen atom and the others represent C($R_1$);

each of $G_{21}$ to $G_{24}$ represents C($R_2$) or a nitrogen atom;

each of $G_{35}$ to $G_{38}$ represents C($R_3$) or a nitrogen atom;

each of $R_1$ and $R_3$ independently represents a hydrogen atom, an alkyl group comprising 1 to 20 carbon atoms, a cycloalkyl group comprising 3 to 20 ring carbon atoms, an aryl group comprising 6 to 18 ring carbon atoms, or a heteroaryl group comprising 5 to 18 ring atoms;

each $R_2$ independently represents a hydrogen atom, an alkyl group comprising 1 to 20 carbon atoms, a cycloalkyl group comprising 3 to 20 ring carbon atoms, an aryl group comprising 6 to 18 ring carbon atoms, or a heteroaryl group selected from the group consisting of a carbolinyl group, a dibenzofuranyl group, a dibenzothiophenyl group, a pyrrolyl group, a furyl group, a thienyl group, a silolyl group, a pyridyl group, a quinolyl group, an isoquinolyl group, an indolyl group, a benzofuryl group, a benzothiophenyl group, an imidazolyl group, a benzimidazolyl group, a pyrimidyl group, a selenophenyl group, an oxadiazolyl group, a triazolyl group, an azaphenanthryl group, and a phenanthrolinyl group;

at least one $R_2$ represents a substituted or unsubstituted dibenzofuranyl group, or a substituted or unsubstituted dihenzothiophenyl group;

$L_1$ represents a single bond, an arylene group comprising 6 to 18 ring carbon atoms, or a heteroarylene group comprising 5 to 18 ring atoms, provided that divalent residues of dibenzofuran and dibenzothiophene are excluded;

$L_2$ represents a single bond, an arylene group comprising 6 to 18 ring carbon atoms, a heteroarylene group selected from the group consisting of residues obtained by removing one hydrogen atom from a carbolinyl group, a dibenzofuranyl group, a dibenzothiophenyl group, a pyrrolyl group, a furyl group, a thienyl group, a silolyl group, a pyridyl group, a quinolyl group, an isoquinolyl group, an indolyl group, a benzofuryl group, a benzothiophenyl group, an imidazolyl group, a benzimidazolyl group, a pyrimidyl group, a selenophenyl group, an oxadiazolyl group, a triazolyl group, an azaphenanthryl group, and a phenanthrolinyl group, an oxygen-comprising divalent linking group, a silicon-comprising divalent linking group, a phosphorus-comprising divalent linking group, or a sulfur-comprising divalent linking group;

Y represents an oxygen atom, a sulfur atom, or —N(-$L_3$-$R_5$)—;

$L_3$ represents a single bond, an arylene group comprising 6 to 18 ring carbon atoms or a heteroarylene group comprising 5 to 18 ring atoms; and $R_5$ represents a hydrogen atom, an alkyl group comprising 1 to 20 carbon atoms, a cycloalkyl group comprising 3 to 20 ring carbon atoms, an aryl group comprising 6 to 18 ring carbon atoms, or a heteroaryl group comprising 5 to 18 ring atoms.

24. An organic electroluminescence device, comprising:

a cathode;

an anode; and an organic thin film layer comprising one or more layers between the cathode and the anode;

wherein:

the organic thin film layer comprises a light emitting layer comprising a phosphorescent emitting material and an electron transporting zone between the light emitting layer and the cathode; and the electron transporting zone comprises a compound represented by formula (1):

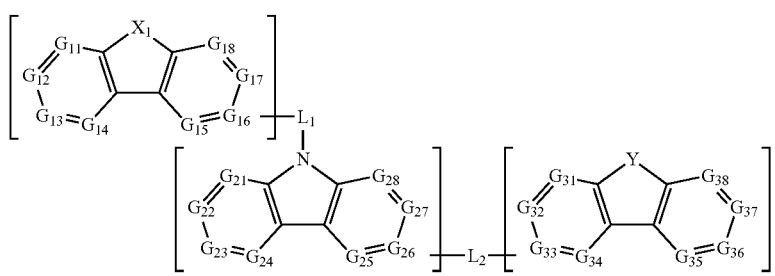

(1)

wherein:
- at least one of $G_{11}$ to $G_{18}$ represents a nitrogen atom, another of $G_{11}$ to $G_{18}$ represents a carbon atom bonded to $L_1$, and the other or others of $G_{11}$ to $G_{18}$ represent $C(R_1)$;
- one of $G_{21}$ to $G_{28}$ represents a carbon atom bonded to $L_2$ and the others represent $C(R_2)$ or a nitrogen atom;
- one of $G_{31}$ to $G_{38}$ represents a carbon atom bonded to $L_2$ and the others represent $C(R_3)$ or a nitrogen atom;
- each of $R_1$ to $R_3$ independently represents a hydrogen atom, a substituted or unsubstituted alkyl group comprising 1 to 20 carbon atoms, a substituted or unsubstituted cycloalkyl group comprising 3 to 20 ring carbon atoms, a substituted or unsubstituted cycloalkoxy group comprising 3 to 20 ring carbon atoms, a substituted or unsubstituted alkoxy group comprising 1 to 20 carbon atoms, a substituted or unsubstituted aryl group comprising 6 to 18 ring carbon atoms, a substituted or unsubstituted heteroaryl group comprising 5 to 18 ring atoms, a substituted or unsubstituted aryloxy group comprising 6 to 18 ring carbon atoms, a substituted or unsubstituted amino group comprising 0 to 20 carbon atoms, a substituted or unsubstituted silyl group comprising 0 to 30 carbon atoms, a fluorine atom, or a cyano group, provided that $R_1$ groups, $R_2$ groups, and $R_3$ groups may be the same or different;
- each optional substituent of $R_1$ to $R_3$ is independently an alkyl group comprising 1 to 20 carbon atoms, a cycloalkyl group comprising 3 to 20 ring carbon atoms, an alkoxy group comprising 1 to 20 carbon atoms, a cycloalkoxy group comprising 3 to 20 ring carbon atoms, an aryl group comprising 6 to 18 ring carbon atoms, a heteroaryl group comprising 5 to 18 ring atoms, an aryloxy group comprising 6 to 18 ring carbon atoms, an amino group comprising 0 to 20 carbon atoms, a sityl group comprising 0 to 30 carbon atoms, a fluorine atom, or a cyano group;
- $X_1$ represents an oxygen atom, a sulfur atom, or —N($R_4$)—;
- $R_4$ represents a hydrogen atom, an alkyl group comprising 1 to 20 carbon atoms, a cycloalkyl group comprising 3 to 20 ring carbon atoms, an aryl group comprising 6 to 18 ring carbon atoms, or a heteroary l group comprising 5 to 18 ring atoms;
- $L_1$ represents a single bond, an alkylene group comprising 1 to 20 carbon atoms, a cycloalkylele group comprising 3 to 20 ring carbon atoms, an arylene group comprising 6 to 18 ring carbon atoms, or a heteroarylene group comprising 5 to 18 ring atoms, provided that divalent residues of dibenzofuran and dibenzothiophene are excluded;
- $L_2$ represents a single bond, an alkylene group comprising 1 to 20 carbon atoms, a cycloalkylene group comprising 3 to 20 ring carbon atoms, an arylene group comprising 6 to 18 ring carbon atoms, a heteroarylene group comprising 5 to 18 ring atoms, a nitrogen-comprising divalent linking group, an oxygen-comprising divalent linking group, a silicon-comprising divalent linking group, a phosphorus-comprising divalent linking group, or a sulfur-comprising divalent linking group;
- Y represents an oxygen atom, a sulfur atom, or —N(-$L_3$-$R_5$)—;
- $L_3$ represents a single bond, an alkylene group comprising 1 to 20 carbon atoms, a cycloalkylene group comprising 3 to 20 ring carbon atoms, an arylene group comprising 6 to 18 ring carbon atoms, or a heteroarylene group comprising 5 to 18 ring atoms; and
- $R_5$ represents a hydrogen atom, an alkyl group comprising 1 to 20 carbon atoms, a cycloalkyl group comprising 3 to 20 ring carbon atoms, an aryl group comprising 6 to 18 ring carbon atoms, or a heteroaryl group comprising 5 to 18 ring atoms;
- provided that when $X_1$ represents an oxygen atom or a sulfur atom, only one of $G_{11}$ to $G_{18}$ represents a nitrogen atom, and when $X_1$ represents —N($R_4$)—, Y represents —N(-$L_3$-$R_5$)—and simultaneously each of $R_2$ and $R_3$ represents a hydrogen atom.

25. The organic electroluminescence device of claim 24, wherein at least one of $G_{11}$ to $C_{14}$ represents a nitrogen atom, one of $G_{15}$ to $C_{18}$ represents a carbon atom bonded to $L_1$, and the other or others of $G_{11}$ to $C_{18}$ represent $C(R_1)$.

26. The organic electroluminescence device of claim 24, wherein $G_{14}$ of formula (1) represents a nitrogen atom.

27. The organic electroluminescence device of claim 24, wherein $G_{16}$ of formula (1) represents a carbon atom bonded to $L_1$.

28. The organic electroluminescence device of claim 24, wherein at least one $R_2$ represents a substituted or unsubstituted carbazolyl group, a substituted or unsubstituted dibenzofuranyl group, or a substituted or unsubstituted dibenzothiophenyl group.

29. The organic electroluminescence device of claim 24, wherein:
- Y of formula (1) represents —N(-$L_3$-$R_5$)—; and
- $R_5$ represents a heteroaryl group represented by formula (A):

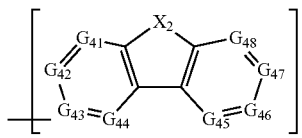

(A)

wherein:

one of $G_{41}$ to $G_{48}$ represents a carbon atom bonded to $L_3$ and the others represent a nitrogen atom or $C(R_6)$;

$R_6$ represents a hydrogen atom, a substituted or unsubstituted alkyl group comprising 1 to 20 carbon atoms, a substituted or unsubstituted cycloalkyl group comprising 3 to 20 ring carbon atoms, a substituted or unsubstituted alkoxy group comprising 1 to 20 carbon atoms, a substituted or unsubstituted cycloalkoxy group comprising 3 to 20 ring carbon atoms, a substituted or unsubstituted aryl group comprising 6 to 18 ring carbon atoms, a substituted or unsubstituted heteroaryl group comprising 5 to 18 ring atoms, a substituted or unsubstituted aryloxy group comprising 6 to 18 ring carbon atoms, a substituted or unsubstituted amino group comprising 0 to 20 carbon atoms, a substituted or unsubstituted silyl group comprising 0 to 30 carbon atoms, a fluorine atom, or a cyano group, provided that $R_6$ groups may be the same or different;

each optional substituent of $R_6$ is independently an alkyl group comprising 1 to 20 carbon atoms, a cycloalkyl group comprising 3 to 20 ring carbon atoms, an alkoxy group comprising 1 to 20 carbon atoms, a cycloalkoxy group comprising 3 to 20 ring carbon atoms, an aryl group comprising 6 to 18 ring carbon atoms, a heteroars group comprising 5 to 18 ring atoms, an aryloxy group comprising 6 to 18 ring carbon atoms, an amino group comprising 0 to 20 carbon atoms, a silyl group comprising 0 to 30 carbon atoms, a fluorine atom, or a cyano group;

$X_2$ represents an oxygen atom, a sulfur atom, or —$N(R_7)$—; and $R_7$ represents a hydrogen atom, an alkyl group comprising 1 to 20 carbon atoms, a cycloalkyl group comprising 3 to 20 ring carbon atoms, an aryl group comprising 6 to 18 ring carbon atoms, or a heteroaryl group comprising 5 to 18 ring atoms.

30. The compound according to claim 1, wherein Y represents an oxygen atom or a sulfur atom.

31. The compound according to claim 17, wherein Y represents an oxygen atom or a sulfur atom.

\* \* \* \* \*